US008105575B2

(12) United States Patent
Kim et al.

(10) Patent No.: US 8,105,575 B2
(45) Date of Patent: Jan. 31, 2012

(54) EXPRESSION VECTORS WITH IMPROVED SAFETY

(75) Inventors: Sunyoung Kim, Gyunggi-do (KR); Sujeong Kim, Seoul (KR); Jun-Tae Lee, Seoul (KR)

(73) Assignee: Viromed Co., Ltd., Seoul (KR)

( * ) Notice: Subject to any disclaimer, the term of this patent is extended or adjusted under 35 U.S.C. 154(b) by 885 days.

(21) Appl. No.: 11/870,361

(22) Filed: Oct. 10, 2007

(65) Prior Publication Data

US 2008/0153770 A1 Jun. 26, 2008

Related U.S. Application Data

(60) Provisional application No. 60/850,269, filed on Oct. 10, 2006.

(51) Int. Cl.
*C12N 15/867* (2006.01)
*C12N 15/09* (2006.01)
*C12N 15/00* (2006.01)

(52) U.S. Cl. .................. 424/93.2; 536/24.1; 435/320.1; 435/325; 435/366; 435/455

(58) Field of Classification Search ........................ None
See application file for complete search history.

(56) References Cited

U.S. PATENT DOCUMENTS

| | | | |
|---|---|---|---|
| 6,451,595 B1 | 9/2002 | Kim et al. | |
| 6,521,457 B2 | 2/2003 | Olsen | |
| 7,049,143 B2 * | 5/2006 | Kim et al. | 435/456 |
| 7,575,924 B2 * | 8/2009 | Trono et al. | 435/366 |
| 2007/0161031 A1 * | 7/2007 | Trinklein et al. | 435/6 |

FOREIGN PATENT DOCUMENTS

| | | |
|---|---|---|
| WO | 0000629 A1 | 1/2000 |
| WO | WO 00/40737 A1 | 7/2000 |
| WO | 2006078880 A2 | 7/2006 |
| WO | 2006089001 A2 | 8/2006 |

OTHER PUBLICATIONS

Strausberg et al, GI 21284401-*Homo sapiens* ribosomal protein L10, mRNA (cDNA clone Image:4499390), with apparent retained intron, 2003.*
Lesk et al, Prediction of Protein Function from Protein Sequence and Structure, p. 27 and 28, downloaded Sep. 16, 2007.*
Sirven, A., et al., "Enhanced Transgene Expression in Cord Blood CD34+—Derived Hematopoietic Cells, Including Developing T Cells and NOD/SCID Mouse Repopulating Cells, Following Transduction with Modified TRIP Lentiviral Vectors," Molecular Therapy, 3:4, Apr. 2001, 438-448.
Farmer, A.A., et al., "Isolation and characterization of the QM promoter," Nucleic Acids Research, 24:11, 1996, 2158-2165.
Kung, A.K., "A Murine Leukemia Virus (MuLV) Long Terminal Repeat Derived from Rhesus Macaques in the Context of a Lentivirus Vector and MuLV *gag* Sequence Results in High-Level Gene Expression in Human T Lymphocytes," J. Virology, 74:8, Apr. 2000, 3668-3681.

Kim, S.H., et al., "Construction of Retroviral Vectors with Improved Safety, Gene Expression, and Versatility," J. of Virology, 72:2, Feb. 1998, 994-1004.
Lotti, F., et al., "Transcriptional Targeting of Lentiviral Vectors by Long Terminal Repeat Enhancer Replacement," J. of Virology, 76:8, Apr. 2002, 3996-4007.
Albert, T.K., et al., "Isolation and characterization of human orthologs of yeast CCR4-Not complex subunits," *Nucleic Acids Res.* 28:809-817, Oxford University Press (2000).
Bignon, C., et al., "cDNA Cloning and Genomic Analysis of a New Multigene Family Sharing Common Phylogenetic and Expression Profiles with the Laminin Receptor Gene," *Biochem. Biophys. Res. Commun.* 184:1165-1172, Elsevier Science Ltd. (1992).
Coffin, JM, "Importance of Norwalk Virus Group in Outbreaks of Epidemic Gastroenteritis," in *Fundamental Virology*, 3rd Ed, Fields, B.N., et al., Eds., Lippincott Williams & Wilkins, Philadelphia, PA, pp. 798-800 (1996).
Cooper, S.J., et al., "Comprehensive analysis of transcriptional promoter structure and function in 1% of the human genome," *Genome Res.* 16:1-10, Cold Spring Harbor Laboratory Press (2006).
Creutz, C.E., et al., "The Copines, a Novel Class of C2 Domain-containing, Calcium-dependent, Phospholipid-binding Proteins Conserved from *Paramecium* to Humans," *J Biol. Chem.* 273:1393-1402, American Society for Biochemistry and Molecular Biology (1998).
Curran M.A.. and Nolan G.P., "Nonprimate Lentiviral Vectors," *Curr. Top. Microbiol. Immunol.* 261:75-105, Springer Verlag (2002).
deWet, J.R., et al., "Firefly Luciferase Gene: Structure and Expression in Mammalian Cells," *Mol. Cell. Biol.* 7:725-737, American Society for Microbiology (1987).
Ercolani, L., et al., "Isolation and Complete Sequence of a Functional Human Glyceraldehyde-3—phosphate Dehydrogenase gene," *J. Biol. Chem.* 263:15335-15341, American Society for Biochemistry and Molecular Biology (1988).
Gilbert, J.R. and Wong-Staal, F., "HIV-2 and SIV Vector Systems," *Somat. Cell Mol. Genet.* 26:83-98, Springer Netherlands (2001).
Gill, D.R., et al., "Increased persistence of lung gene expression using plasmids containing the ubiquitin C or elongation factor 1α promoter," *Gene Ther.* 8:1539-1546, Nature Publishing Group (2001). Hacein-Bey-Abina, S., et al.,"*LMO2*-Associated Clonal T Cell Proliferation in Two Patients after Gene Therapy for SCID-X1," *Science* 302:415-419, American Assn. for the Advancement of Science (2003).
Haft, C.R., et al., "Identification of a Family of Sorting Nexin Molecules and Characterization of Their Association with Receptors," *Mol. Cell. Biol.* 18:7278-7287, American Society for Microbiology (1998).
Haller, A.A. and Semler, B.L., "Linker Scanning Mutagenesis of the Internal Ribosome Entry Site of Poliovirus RNA," *J. Virol.* 66:5075-5086, American Society for Microbiology (1992).
Hawley, R.G., et al., Handicapped retroviral vectors efficiently transduce foreign genes into hematopoietic stem cells, *Proc. Natl. Acad. Sci.* USA 84:2406-2410, National Academy of Sciences (1987).
Herweijer, H., et al., "Time course of gene expression after plasmid DNA gene transfer to the liver," *J. Gene Med.* 3:280-291, John Wiley & Sons (2001).
Hong, Y., et al., "Factors affecting retrovirus-mediated gene transfer to human CD34+ cells," *J. Gene Med.* 6: 724-733, John Wiley & Sons (2004).

(Continued)

Primary Examiner — Maria Marvich
(74) Attorney, Agent, or Firm — Sughrue Mion, PLLC

(57) ABSTRACT

The present invention relates to the use of internal promoters in mammalian expression vectors including plasmid vectors and enhancer-deleted retroviral vectors. The retroviral vectors have improved safety and optimal levels of transgene expression and vector titers.

27 Claims, 10 Drawing Sheets

OTHER PUBLICATIONS

Horikawa, I., et al., "Molecular Cloning of a Novel Human cDNA on Chromosome 1q21 and Its Mouse Homolog Encoding a Nuclear Protein with DNA-Binding Ability," *Biochem. Biophys. Res. Commun.* 208:999-1007, Academic Press (1995).

Jaalouk, D.E., et al., "Inhibition of histone deacetylation in 293GPG packaging cell line improves the production of self-inactivating MLV-derived retroviral vectors," *Virol. J.* 3:27, 12 pages (2006).

Jang, S.K., et al., "A segment of the 5' Nontranslated Region of Encephalomyocarditis Virus RNA Directs Internal Entry of Ribosomes during In Vitro Translation," *J. Virol.* 62:2636-2643, American Society for Microbiology (1988).

Kim, D.W., et al., "Use of the human elongation factor 1α promoter as a versatile and efficient expression system," *Gene* 91:217-223, Elsevier Science Ltd. (1990).

Kim, S., et al., "Factors affecting the performance of different long terminal repeats in the retroviral vector," *Biochem. Biophys. Res. Commun.* 343:1017-1022, Elsevier Science Ltd. (2006).

Lee, Y., et al., "Improved Expression of Vascular Endothelial Growth Factor by Naked DNA in Mouse Skeletal Muscles: Implication for Gene Therapy of Ischemic Diseases," *Biochem. Biophys. Res. Commun.* 272: 230-235, Academic Press (2000).

Logan, A.C., et al., "Integrated Self-Inactivating Lentiviral Vectors Produce Full-Length Genomic Transcripts Competent for Encapsidation and Integration," *J. Virol.* 78:8421-8436, American Society for Microbiology (2004).

Meyer, K., et al., "Interaction of Eukaryotic Initiation Factor eIF-4B with a Picornavirus Internal Translation Initiation Site," *J. Virol.* 69:2819-2824, American Society for Microbiology (1995).

Miller, A.D. and Buttimore, C., "Redesign of Retrovirus Packaging Cell Lines To Avoid Recombination Leading to Helper Virus Production," *Mol. Cell. Biol.* 6: 2895-2902, American Society for Microbiology (1986).

Mitrophanous, K.A., et al., "Stable gene transfer to the nervous system using a non-primate lentiviral vector," *Gene Ther.* 6:1808-1818, Nature Publishing Group (1999).

Miyamoto, N.G., "Nucleotide sequence of the human β-actin promoter 5' flanking region," *Nucleic Acids Res.* 15:9095, Oxford University Press (1987).

Nakajima-Iijima, S., et al., "Molecular structure of the human cytoplasmic β—actin gene: Interspecies homology of sequences in the introns," *Proc. Natl. Acad. Sci.* USA 82: 6133-6137, National Academy of Sciences (1985).

Naldini, L., et al., "In Vivo Gene Delivery and Stable Transduction of Nondividing Cells by a Lentiviral Vector," *Science* 272:263-267, American Assn. for the Advancement of Science (1996).

Olson, P., et al., "Improved Self-Inactivating Retroviral Vectors Derived from Spleen Necrosis Virus," *J. Virol.* 68:7060-7066, American Society for Microbiology (1994).

Ramezani, A., et al., "Stable Gammaretroviral Vector Expression during Embryonic Stem Cell-Derived In Vitro Hematopoietic Development," *Mol. Ther.* 14:245-254, The American Society of Gene Therapy (2006).

Sauter, S.L. and Gasmi, M., "FIV Vector Systems," *Somat. Cell Mol. Genet.* 26:99-129, Springer Netherlands (2001).

Scheper, G.C., et al., Binding of eukaryotic initiation factor-2 and trans-acting factors to the 5' untranslated region of encephalomyocarditis virus RNA, *Biochimie.* 76:801-809, Société franeise de biochimie et biologie moléoulaire (1994).

Strausberg, R.L., et al., "Generation and initial analysis of more than 15,000 full-length human and mouse cDNA sequences," *Proc. Natl. Acad. Sci.* USA 99:16899-16903, National Academy of Sciences (2002).

Sun, W., et al., "Transactivation of the Moloney Murine Leukemia Virus and T-Cell Receptor β-Chain Enhancers by *cbf* and *ets* Requires Intact Binding Sites for Both Proteins," *J. Virol.* 69:4941-4949, American Society for Microbiology (1996).

Wahlers, A., et al., "Upstream Conserved Sequences of Mouse Leukemia Viruses Are Important for High Transgene Expression in Lymphoid and Hematopoietic Cells," *Mol. Ther.* 6:313-320, Academic Press (2002).

Yee, J.-K., et al., "Gene Expression from transcriptionally disabled retroviral vectors," *Proc. Natl. Acad. Sci.* USA 84:5197-5201, National Academy of Sciences (1987).

Yu, S.-F., et al., "Self-inactivating retroviral vectors designed for transfer of whole genes into mammalian cells," *Proc. Natl. Acad. Sci.* USA 83:3194-3198, National Academy of Sciences (1986).

Yu, S.S., et al., "Construction of a retroviral vector production system with the minimum possibility of a homologous recombination," *Gene Ther.* 10:706-711, Nature Publishing Group (2003).

Flamant, F., et al., "Importance of 3' non-coding sequences for efficient retrovirus-mediated gene transfer in avian cells revealed by self-inactivating vectors," J. General Virology, 74, 1993, 39-46.

Yu, S.S., et al., "High efficiency retroviral vectors that contain no viral coding sequences," Gene Therapy, 7, 797-804, 2000.

Flasshove, M., et al., "Type and position of promoter elements in retroviral vectors have substantial effects on the expression level of an enhanced green fluorescent protein reported gene," J. Cancer Res Clin Oncol, 126: 391-399, 2000.

Ramezani, A., et al., "Stable Gammaretroviral Vector Expression during Embryonic Stem Cell-Derived In Vitro hematopoietic Development," Molecular Therapy, 14:2, 245-254, 2006.

Cooper, S., et al., "Cpmprehensive analysis of transcriptional promoter structure and function in 1% of the human genome," Genome Res. 16, 1-10, 2006.

\* cited by examiner

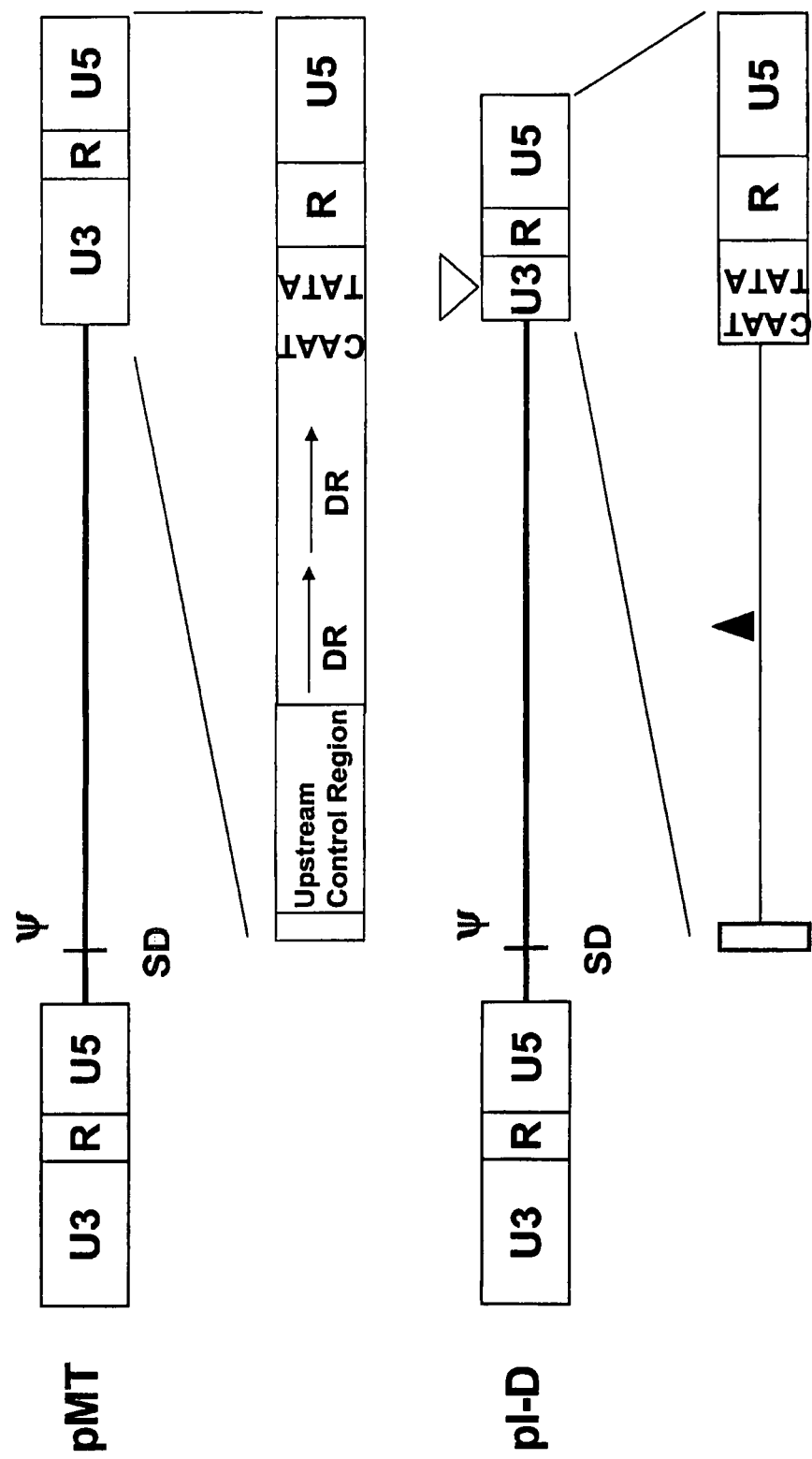
Fig 1. U3-inactivated retroviral vector

Fig 2. pI-ND
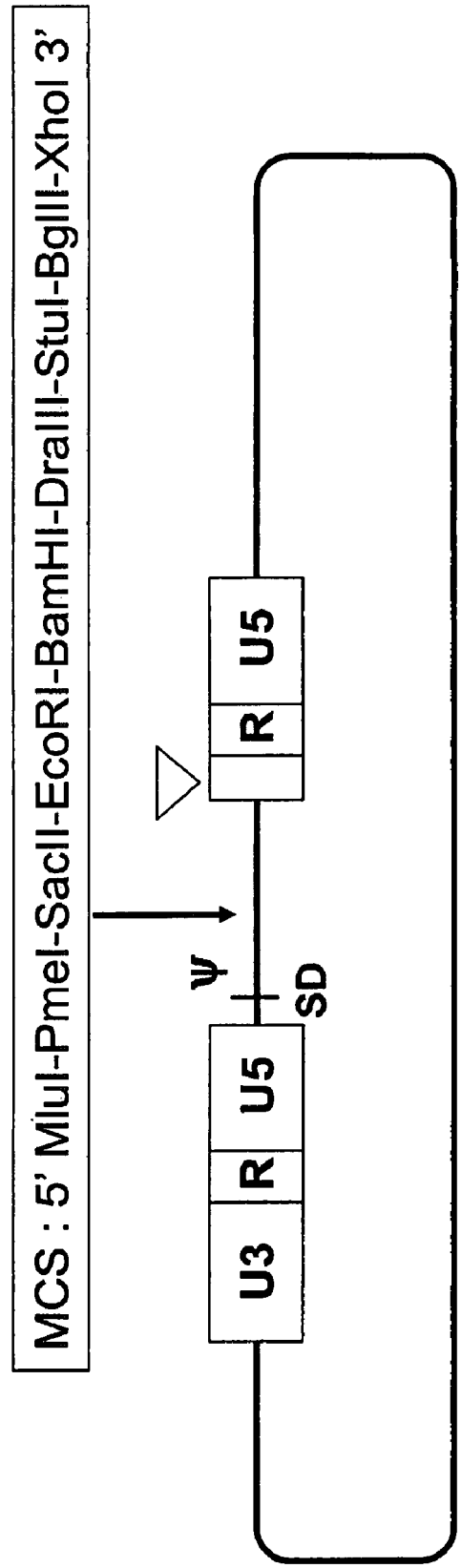

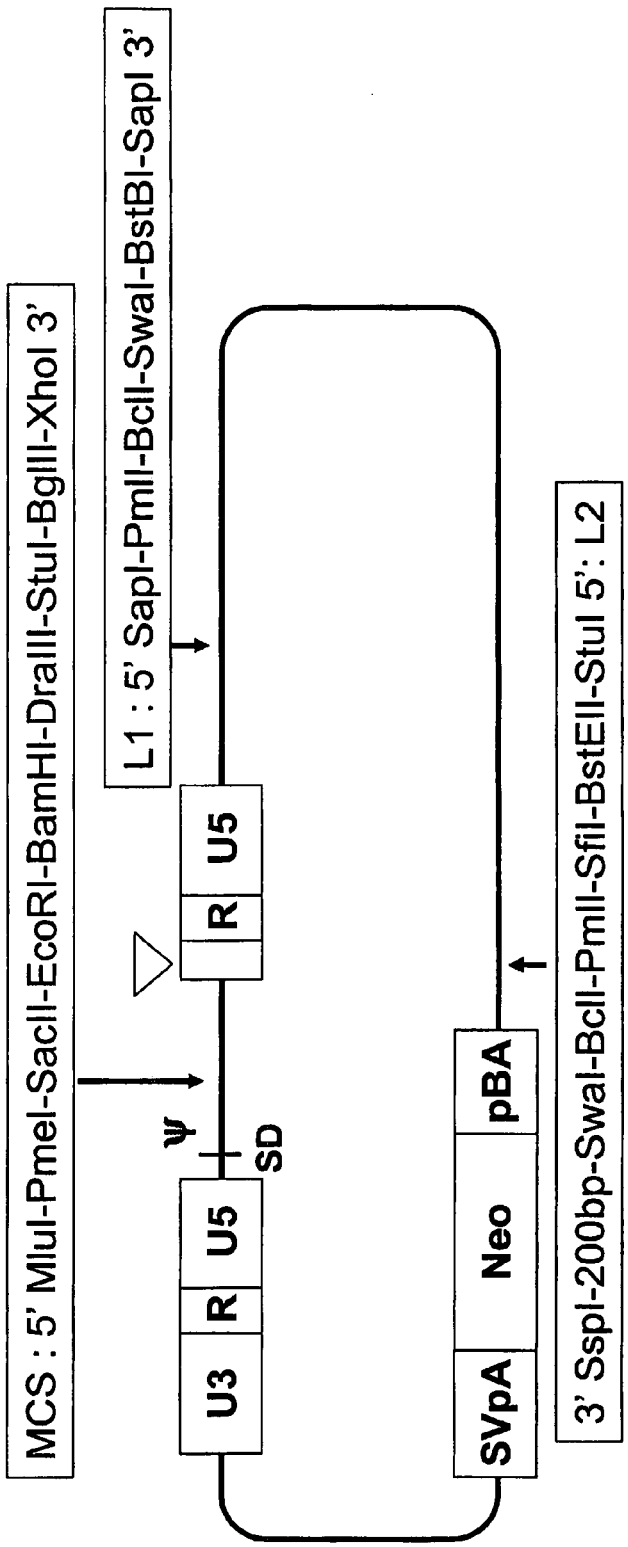
Fig 3. pI-LND-n

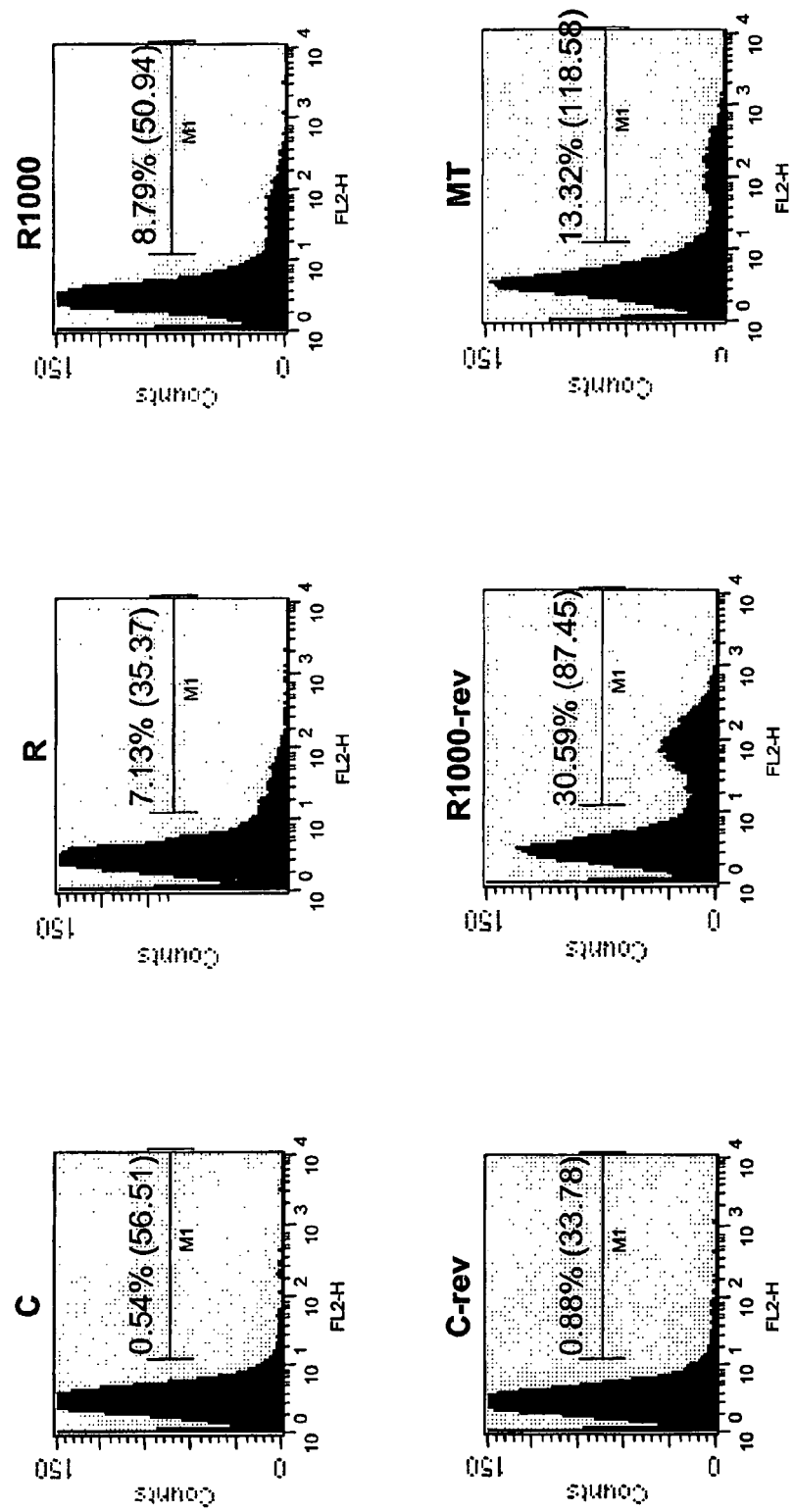
Fig 4. gp91 expression

Fig 5. GAPDH promoter

TTCATCCAAGCGTGTAAGGGTCCCCGTCCTTGACTCCCTAGTGTCCTGCTGCCCACAGTC
CAGTCCTGGGAACCAGCACCGATCACCTCCCATCGGGCCAATCTCAGTCCCTTCCCCCCT
ACGTCGGGGCCCACACGCTCGGTGCGTGCCCAGTTGAACCAGGCGGCTGCGGAAAAAA
AAAAGCGGGGAGAAAGTAGGGCCCGGCTACTAGCGGTTTTACGGGCGCACGTAGCTCA
GGCCTCAAGACCTTGGGCTGGGACTGGCTGAGCCTGGCGGGAGGCGGGGTCCGAGTCA
CCGCCTGCCG<u>CCGCGCCC</u>CCGGTTTC<u>TATAAA</u>TTGAGCCCGCAGCCTCCCGCTTCG<u>C</u>TCT
             BRE               TATA box                           +1
CTGCTCCTCCTGTTCGACAGTCAGCCGCATCTTCTTTTGCGTCGCCAGGTGAAGACGGGC
GGAGAGAAACCCGGGAGGCTAGGGACGGCCTGAAGGCGGCAGGGGCGGGCGCAGGC
CGGATGTGTTCGCGCCGCTGCGGGGTGGGCCCGGGCGGCCTCCGCATTGCAGGGGCGG
GCGGAGGACGTGATGCGGCGCGGGCTGGGCATGGAGGCCTGGTGGGGAGGGGAGGG
GAGGCGTGTGTGTCGGCCGGGGCCACTAGGCGCTCACTGTTCTCTCCCTCCGCGCAGCC
GAGCCACATCGCTCAGACACC Fig 6. RPL 10 promoter GTGCGCTCGAGCAGGATTTCCTCCCGTCCTTCCTGTCAAAGGACGGGAAGACTTTGTTA
CCCCACCGCGCCCCACCTGCAGAATGGTGGACAGATACCTCCAGATGCCACTTCCCCC
AGGACGCCCGCCTGCTCTGCGCACCTCTCCCCGGATGCTGCCCCGTGGGCGGGTGGGGG
CGGCCCTGCTTCCCCACGACCCCCAGACGCACCCGGAGGGACTC
TTGAGCACAGTGGAGTGGGAAGGGCGAGGTGGGGCGGTGCCCAGGCGAGAGCGGCTC
ATGGGAGGCGGCGCCCGAGACGCAGCTGGTCGGGACGGTGCGGGTCAGGGTGGGCGG
AGCGGGGCTAGAGATGCCCCGGGGTTTCCCAGGCCATGAGTCTCCGTGGAGATTTCTCC
TCGACCTCTTCCCCGCGGCAATGTGCGAACCCTGGGTCTCCAGGAAACGGGGATACGG
GGCATGGCTCCCAGCAAGGCCTGGTCCAGCCTCTCCGGTAGGGGAATGGGTCTCCCCCT
CCGGCCTCCCGGGTTGACAAAGGAACGCGGGCCCAGATCCCCGTATGGCGCTTCACCG
CCGGGGCCTCTAGCCTAGAAGGAGGCACGGAGCGCGTGTCCGAGACCCGTGCAAGCTC
AGGGACACTCTCGCGGTCGCCGGGAGGCCCACCTAGGGTACTTTCCTTTTTTCCACTCTC
AGAAATATACGTCTGTCACAGTTAACGGCAAAGCCTAGGGCAAGAGTTCTACGCCCAAG
ATGGCCAGCCGGAAGCGGGCTTCTCGCGACCATGTGGCGAAGCCCCATTCGTCAGCTGG
CCGCCCGCGGCCCTGGTACCCGGTCACCTCTCTGATCTGCGCATGTGCTGGGCTACGCCC
GGGCGCAAGCGCCAAGAGCGGCTGCGTCTATGGTCATGACGTCTGACAGAGCGTCCAC
CCGTCTTCGACAGGACTCTATGGTTCTTACGCGCGCAGACAGACCGCC<u>TATATAA</u>GCCAT
                                                                                                       TATA box
GCGCAGGCGGAGGAGCGC<u>C</u>TCTTTCCCTTCGGTGTGGTGAGTAAGCGCAGTTGTCGTCT
                   +1
CTTGCGGTGCCGTTGCTGGTTCTCACACCTTTTAGGTCTGTTCTCGTCTTCCGTTCCGACT
CTCTCTTTTTCGTTGCAGCCACTGAAGATCCTGGTGTCGCC Fig 7. LENG8 promoter TTGTATCAGAGTCCTGGACGGAAACAGATGGCACTCAAAAGGTGGCGCGCAGTTCAGA
GAAATGCCTATGTACGGATTTGGTCCAATGCCTCAGCCTGACCTCAGGGACCTTCGGGG
GTCTGCTCCGCGCCCACCCTTACACATCTGTGACCCCACACACTTCCACCCCAGCGCCA
CTGCCAACAGCTACACCCATCCCCCTCCAACCGCGTCAGCTTCCAGCCTCGGTCCATCT
GAACTCGCCGTGCCCCCTCCCCTGCGCCCTTCCAGATTCATTTGCTAGGGAAGCCCGCT
CTTCCGGGTGGAGCTGTTCCTCATCCCCTTTCTTTATCATTCTCTCCCCAGGGCTTCCACA
TCACCGTGCTGTGGACAATCCCGGAACTCCTGTCACGCCAGTTTACATTTAGGAACAGT
AATGGCTCCCACTGACTCAGTCAAAACAAGGCTGCGGCCGGGCACGGTGGCTCACGCC
CGTAATCCCAGCACTTTGGGAAGCCGAGACGGAGGGATCACGAGGTCAGGAGTTCGAG
AACAGCCTGGCCGACATGGTGAAACCCCGTCTTTACAAAAACACAAAAATTAGCCGGG
CATAGTGGCGCGCGCCTGTAATCCCAGCTACTCCGGAGGCTGAGGCAGAATTGTTTGAA
CCCAGGAGGCGGAGGTTGCAGTGAGCAGAGATCACGCCACTGTACTCTATCGTGGGCG
ACGACAGAGCAAGAGCAAGACTCCGTCTCCGAGAACAACAACAACAGCAACAAGAA
AACAACAATAAAAAAAATAAGGCTGCGTGGGAGGCAGAAAGAGCTAATGCGGCCACG
CTTGTCCCCTCGGGGCCACCGTCCCCACCCAGACTTCCGGTCTGCCTTAAAATGTTCATG
CGTAAGTGCGTGGGCAGGAAGGCGGGCTCAAGCGCAGCTCGTGGCGTTCATTGGCTGTG
CAGGGCCGAGGGAGGCGGTGCAAGGCCGCCGCGTGACGTCAGGACGCCGCGGTCAGG
ACGTCGAAGCCAAAGAAGAC<u>C</u>AGAG<u>C</u>CAGCCGGGTGGCACAGCGGTGTCGTGGCCGT
                  (+1)    +1
GTTGCTGATCGCCTGGGTGGTTGTTGGCGTGTCCCTGCAGCGAAGGATCCTGGTTGGTAA
GGGGAGCGGCGGGCGAGCAGGCGGGCGGGATAGCATCTCCTTTTGGTCTTGCGCCCC
GCGAGCCCCGAGGCCTTCTCGGCCGTCGCAGCAGCAGACGCCGCGCGCGAGCGTCGAC
AGGGTGTGGCGGCGCAGGGGCAGCCACTGCGCCTGCGCACCGGGCCTGGGGCCGCGCG
TTCGGGCACTAGCGCGCGTGCGCCGTCGTCTTCTACTTTCCACACCCAGAACTCTTCAGA
TCCTTGACCCCAGTGGCTTTTCAGTCAGCCTCCCCTTTTCTGCCCAGCTTCTCTTGAGTCC
ATCTACTTTTCTTCCCCACTTTGTGACGTGTTTTTAGCTCCCCCTTAAGTCTCCCTAACTCA
TTCTTTTTCTCATAGGCAGTGAAAAAGCAGTCTGGCTCCCGAGGTCCACCCCTTATACCC
CAAGGTCCAG Fig 8. SNX3 promoter AATCCAGACGCGTGTCTGGTGCAACGCTCGGGTTTATGGCAAAATCATCTCAGGCATTT
GCTTAACCTTCTCCAGAAAGGCATTTTCAGGGGTTCACAGTGAGACGGTGCACAGGTTG
GCACAGAGTTAGTAGGGGCAGTTTTGTTTCGATTTGCGGGCAAATCTCTAAGATCTCTCC
GTTTAACTTTCGCCCGCAATTCCCAAAGCCGCTAAAGCCGTTTCCGGCGCTCTACCCCG
CCGCAGGCCGAGGCTGGCGCAGAGAGACAGGAAGCGCCAGCTCTGGGCGTCTGGGTC
CTCGCCTCCTCGGCCGCAGCCCCGCGGCGGCGCGCTCGCGGTGCATTGTGGGCGCTGTA
GTCCGGCCGGAACCTGTTTGCGACCCCGAGTCCCATGACACCGCTTCTCCTCACACCCC
+1
AGTCCGCAGTGCCCCTCCCCAGCCTCGGCCGGGCCTCCCGGGAGCCGGGCGTGGCGTTC
CAGCTAGTGAGCCGTTTCTCCCCTGGGCTCGGAGGCGGAAGCTTGAGGGGCGCGGGGA
GGAGCTTCGCGTGCGGGGTGAACGCCCGCTCTACGTGCTCGTTCTCTTCGCGACCGCTG
CGCGCGAGCCCCGTGTCCCCACGGCGGGCAGCAGCGGCGGCGGCGGCTGAACGC
GGAGGGGGCGGAGGGAGCCCGCGGCGGCGGCAGCAGCTACAGCGAA Fig 9. ITGB4BP promoter TCTGTCCCTCAAGGCACAGCTGGACTCATCCCTTTCCCCAAACCTGCCCTTCCTCCGGCT
TCATTTCCATCAATACCTCCATCATCAACCCTTCCGCGAGACACTCCTGGCCCCTCCTCTC
CCTCATGCCTCACAACCGACCAGCCGGAGGTCTAGGTCGATGACAGCTCCTAAAAAGCT
CCTGAATGAATAATGAATGAATGAACGCGAGCAGGCTAGGCGTGGGGCCAGGCGGGGT
CGCGCCCAGACCGCTCGCGACCATAGAGTCCGCCGGAGGCCGGAGGTAGAGGGGCTGG
ATGCGTGGCGGGGAGCGCCGGGCTCTCCCGGAAGTCTCCCTGGACGGAAGTGGA<u>A</u>ACG
                                                                                                    +1

GAAACCTTTTTAGGGAGTCC<u>A</u>AGGTACAGTCGCCGCGTGCGGAGCTTGTTACTGGTTACT
                    (+1)

TGGTAAGCTGGTGTGAGGGGAACCTGGGAGGGTCAGCTCCGGTCCTGGGTCGGGAGGG
GTGGGGGCCAGAGGATTCAGGGCCGGAGGTTCTGGTGGGGGCCCAGTGGGCGGGACCC
GAGGACGGAGGGGCCGGGAGGCCGAGAGGGGCGGGGTCGCGGCGGGGCCTGAGGGA
CGGAGGCCGGGATACTTGGGAAAGGATCCGCCGGCCTTGAACTCCCGCCTCCGCCGCCC
CTAGGCCTC

Fig 10. UQCRQ promoter

GTCACCTTTTTGTTCCCTCCCCCGCCTCCCGCATTCGGCCGCTTCCTGACTGGGATTCCAC
AGAAAAGCCGAGGGCTGAGGAGAAGTGTGAGCGCCTCCGCCTGTCCACTGTCCCCCAA
AGTCAGTTCAATCCCCGACGTCCTCCGCTAGGCTCCACCCCACCGGCCCGGGCAGGGCC
TCCAAGGCACCTCCCACCTACGGGTCACCCAGTCAGCCCACTTCTTTCTGGGACAAAGG
CGTCATCCCTTAGAGACAGTAGGAAAATGGTATCTCCCGGAAGTTACCTCACGACCTCC
AAGAGCGGCTTCCAACCTTGCCGGAAATGACGAACGAGTCAACCGGATCGGTGACTGT
                                                                         (+1)                    +1
GGAGGGCGAGCTGAGCCCTGTGCGTGAGTGGGGTCTGGTTGTGCAGTGTTCGTGGACCC
TGGGAGGCTAGGGGCGCCCCGCTGGGCTGGGAAAGGATAAGGAGTGCAGGGGCAGGA
GTCTGGGGTTGGGGATGGACCCCCGCGGGGACTGCGGCGCTTCGCGAAAGCGAGCCAA
GCGCCTGTCCACCCTCGG TCCTGCAGGGCCGCCGCCACA

SEQUENCE LISTING

```
<160> NUMBER OF SEQ ID NOS: 87

<210> SEQ ID NO 1
<211> LENGTH: 1567
<212> TYPE: DNA
<213> ORGANISM: Artificial Sequence
<220> FEATURE:
<223> OTHER INFORMATION: Virus HCMV IE promoter

<400> SEQUENCE: 1
tgacattgat tattgactag ttattaatag taatcaatta cggggtcatt agttcatagc      60
ccatatatgg agttccgcgt tacataactt acggtaaatg gcccgcctgg ctgaccgccc     120
```

```
aacgaccccc gcccattgac gtcaataatg acgtatgttc ccatagtaac gccaataggg    180
actttccatt gacgtcaatg ggtggagtat ttacggtaaa ctgcccactt ggcagtacat    240
caagtgtatc atatgccaag tacgccccct attgacgtca atgacggtaa atggcccgcc    300
tggcattatg cccagtacat gaccttatgg gactttccta cttggcagta catctacgta    360
ttagtcatcg ctattaccat ggtgatgcgg ttttggcagt acatcaatgg gcgtggatag    420
cggtttgact cacggggatt tccaagtctc cacccccattg acgtcaatgg gagtttgttt    480
tggcaccaaa atcaacggga ctttccaaaa tgtcgtaaca actccgcccc attgacgcaa    540
atgggcggta ggcgtgtacg gtgggaggtc tatataagca gagctcgttt agtgaaccgt    600
cagatcgcct ggagacgcca tccacgctgt tttgacctcc atagaagaca ccgggaccga    660
tccagcctcc gcggccggga acggtgcatt ggaacgcgga ttccccgtgc caagagtgac    720
gtaagtaccg cctatagagt ctataggccc accccttgg cttcttatgc atgctatact    780 gttttggct tggggtctat acaccccgc ttcctcatgt tataggtgat ggtatagctt    840
agcctatagg tgtgggttat tgaccattat tgaccactcc cctattggtg acgatacttt    900
ccattactaa tccataacat ggctctttgc cacaactctc tttattggct atatgccaat    960
acactgtcct tcagagactg acacggactc tgtattttta caggatgggg tctcatttat   1020
tatttacaaa ttcacatata caacaccacc gtccccagtg cccgcagttt ttattaaaca   1080
taacgtggga tctccacgcg aatctcgggt acgtgttccg gacatgggct cttctccggt   1140
agcggcggag cttctacatc cgagccctgc tcccatgcct ccagcgactc atggtcgctc   1200
ggcagctcct tgctcctaac agtggaggcc agacttaggc acagcacgat gcccaccacc   1260
accagtgtgc cgcacaaggc cgtggcggta gggtatgtgt ctgaaaatga gctcggggag   1320
cgggcttgca ccgctgacgc atttggaaga cttaaggcag cggcagaaga agatgcaggc   1380
agctgagttg ttgtgttctg ataagagtca gaggtaactc ccgttgcggt gctgttaacg   1440
gtggagggca gtgtagtctg agcagtactc gttgctgccg cgcgcgccac cagacataat   1500
agctgacaga ctaacagact gttcctttcc atgggtcttt tctgcagtca ccgtccttga   1560
cacgatg                                                             1567

<210> SEQ ID NO 2
<211> LENGTH: 431
<212> TYPE: DNA
<213> ORGANISM: Artificial Sequence
<220> FEATURE:
<223> OTHER INFORMATION: Virus MLV U3 region

<400> SEQUENCE: 2
gcaaggcatg gaaaaataca taactgagaa tagaaaagtt cagatcaagg tcaggaacag     60
atggaacagc tgaatatggg ccaaacagga tatctgtggt aagcagttcc tgccccggct    120
cagggccaag aacagatgga acagctgaat atgggccaaa caggatatct gtggtaagca    180
gttcctgccc cggctcaggg ccaagaacag atggtcccca gatgcggtcc agccctcagc    240
agtttctaga gaaccatcag atgtttccag ggtgccccaa ggacctgaaa tgaccctgtg    300
ccttatttga actaaccaat cagttcgctt ctcgcttctg ttcgcgcgct tctgctcccc    360
gagctcaata aaagagccca caaccccctca ctcggcgcgc cagtcttccg atagactgcg    420
tcgcccgggt a                                                         431

<210> SEQ ID NO 3
<211> LENGTH: 1703
<212> TYPE: DNA
```

<213> ORGANISM: Artificial Sequence
<220> FEATURE:
<223> OTHER INFORMATION: Synthetic CMV enhancer/ubiquitin promoter

<400> SEQUENCE: 3

| | | | | | |
|---|---|---|---|---|---|
| ttgacattga | ttattgacta | gttattaata | gtaatcaatt | acggggtcat | tagttcatag | 60 |
| cccatatatg | gagttccgcg | ttacataact | tacggtaaat | ggcccgcctg | gctgaccgcc | 120 |
| caacgacccc | cgcccattga | cgtcaataat | gacgtatgtt | cccatagtaa | cgccaatagg | 180 |
| gactttccat | tgacgtcaat | gggtggacta | tttacggtaa | actgcccact | tggcagtaca | 240 |
| tcaagtgtat | catatgccaa | gtacgccccc | tattgacgtc | aatgacggta | aatggcccgc | 300 |
| ctggcattat | gcccagtaca | tgaccttatg | ggactttcct | acttggcagt | acatctacgt | 360 |
| attagtcatc | gctattacca | tggtgatgcg | gttttggcag | tacatcaatg | ggcgtggata | 420 |
| gcggtttgac | tcacggggat | ttccaagtct | ccaccccatt | gacgtcaatg | ggagtttgtt | 480 |
| ttggctctag | cggcctccgc | gccgggtttt | ggcgcctccc | gcgggcgccc | cctcctcac | 540 |
| ggcgagcgct | gccacgtcag | acgaagggcg | cagcgagcgt | cctgatcctt | ccgcccggac | 600 |
| gctcaggaca | gcggcccgct | gctcataaga | ctcggcctta | gaaccccagt | atcagcagaa | 660 |
| ggacatttta | ggacgggact | tgggtgactc | tagggcactg | gttttctttc | cagagagcgg | 720 |
| aacaggcgag | gaaaagtagt | cccttctcgg | cgattctgcg | gagggatctc | cgtgggcgg | 780 |
| tgaacgccga | tgattatata | aggacgcgcc | gggtgtggca | cagctagttc | cgtcgcagcc | 840 |
| gggatttggg | tcgcggttct | tgtttgtgga | tcgctgtgat | cgtcacttgg | tgagtagcgg | 900 |
| gctgctgggc | tggccggggc | tttcgtggcc | gccgggccgc | tcggtgggac | ggaagcgtgt | 960 |
| ggagagaccg | ccaagggctg | tagtctgggt | ccgcgagcaa | ggttgccctg | aactgggggt | 1020 |
| tggggggagc | gcagcaaaat | ggcggctgtt | cccgagtctt | gaatggaaga | cgcttgtgag | 1080 |
| gcggcctgtg | aggtcgttga | aacaaggtgg | ggggcatggt | gggcggcaag | aacccaaggt | 1140 |
| cttgaggcct | tcgctaatgc | gggaaagctc | ttattcgggt | gagatgggct | ggggcaccat | 1200 |
| ctggggaccc | tgacgtgaag | tttgtcactg | actggagaac | tcggtttgtc | gtctgttgcg | 1260 |
| ggggcggcag | ttatggcggt | gccgttgggc | agtgcacccg | tacctttggg | agcgcgcgcc | 1320 |
| ctcgtcgtgt | cgtgacgtca | cccgttctgt | tggcttataa | tgcagggtgg | ggccacctgc | 1380 |
| cggtaggtgt | gcggtaggct | tttctccgtc | gcaggacgca | gggttcgggc | ctagggtagg | 1440 |
| ctctcctgaa | tcgacaggcg | ccggacctct | ggtgagggga | gggataagtg | aggcgtcagt | 1500 |
| ttctttggtc | ggttttatgt | acctatcttc | ttaagtagct | gaagctccgg | ttttgaacta | 1560 |
| tgcgctcggg | gttggcgagt | gtgttttgtg | aagttttta | ggcaccttt | gaaatgtaat | 1620 |
| catttgggtc | aatatgtaat | tttcagtgtt | agactagtaa | attgtccgct | aaattctggc | 1680 |
| cgttttggc | ttttttgtta | gac | | | | 1703 |

<210> SEQ ID NO 4
<211> LENGTH: 1735
<212> TYPE: DNA
<213> ORGANISM: Artificial Sequence
<220> FEATURE:
<223> OTHER INFORMATION: Synthetic CAG promoter

<400> SEQUENCE: 4

| | | | | | |
|---|---|---|---|---|---|
| attgattatt | gactagttat | taatagtaat | caattacggg | gtcattagtt | catagcccat | 60 |
| atatggagtt | ccgcgttaca | taacttacgg | taaatggccc | gcctggctga | ccgcccaacg | 120 |
| acccccgccc | attgacgtca | ataatgacgt | atgttcccat | agtaacgcca | atagggactt | 180 |

-continued

```
tccattgacg tcaatgggtg gagtatttac ggtaaactgc ccacttggca gtacatcaag    240
tgtatcatat gccaagtacg cccctattg acgtcaatga cggtaaatgg cccgcctggc    300
attatgccca gtacatgacc ttatgggact ttcctacttg gcagtacatc tacgtattag    360
tcatcgctat taccatggtc gaggtgagcc ccacgttctg cttcactctc ccatctccc    420 cccctcccc acccccaatt ttgtatttat ttattttta attattttgt gcagcgatgg    480 gggcggggg ggggggggg cgcgcgccag gcggggcggg gcgggcgag gggcggggcg    540 gggcgaggcg gagaggtgcg gcggcagcca atcagagcgg cgcgctccga aagtttcctt    600
ttatggcgag gcggcggcgg cggcggccct ataaaaagcg aagcgcgcgg cgggcgggag    660
tcgctgcgcg ctgccttcgc cccgtgcccc gctccgccgc cgcctcgcgc cgcccgcccc    720
ggctctgact gaccgcgtta ctcccacagg tgagcgggcg ggacgccct tctcctccgg    780 gctgtaatta gcgcttggtt taatgacggc ttgtttcttt tctgtggctg cgtgaaagcc    840 ttgagggct ccgggaggc ctttgtgcg gggagcgg ctcggggggt gcgtgcgtgt    900
gtgtgtgcgt ggggagcgcc gcgtgcggct ccgcgctgcc cggcggctgt gagcgctgcg    960
ggcgcggcgc gggctttgt gcgctccgca gtgtgcgcga gggagcgcg gccgggggcg   1020 gtgccccgcg gtgcggggg ggctgcgagg ggaacaaagg ctgcgtgcgg ggtgtgtgcg   1080
tgggggggtg agcaggggt gtgggcgcgt cggtcgggct gcaaccccc ctgcacccc   1140 ctccccgagt tgctgagcac ggcccggctt cgggtgcggg gctccgtacg gggcgtggcg   1200
cggggctcgc cgtgccggc ggggggtggc ggcaggtggg ggtgccggc ggggcggggc   1260 cgcctcgggc cggggaggc tcgggggagg ggcgcggcgg cccccggagc gccggcggct   1320
gtcgaggcgc ggcgagccgc agccattgcc ttttatggta atcgtgcgag agggcgcagg   1380
gacttccttt gtcccaaatc tgtgcggagc cgaaatctgg gaggcgccgc cgcacccct   1440 ctagcgggcg cggggcgaag cggtgcggcg ccggcaggaa ggaaatgggc ggggagggcc   1500
ttcgtgcgtc gccgcgccgc cgtccccttc tccctctcca gcctcgggc tgtccgcggg   1560 gggacggctg ccttcggggg gacggggca gggcgggtt cggcttctgg cgtgtgaccg   1620
gcggctctag agcctctgct aaccatgttc atgccttctt cttttttccta cagctcctgg   1680 gcaacgtgct ggttattgtg ctgtctcatc attttggcaa agaattgatt tatcg         1735
```

<210> SEQ ID NO 5
<211> LENGTH: 1450
<212> TYPE: DNA
<213> ORGANISM: Artificial Sequence
<220> FEATURE:
<223> OTHER INFORMATION: Homo sapiens EF-1alpha promoter

<400> SEQUENCE: 5

```
gtaagccagc aatggtagag ggaagattct gcacgtccct tccaggcggc ctccccgtca     60
ccaccccccc caacccgccc cgaccggagc tgagagtaat tcatacaaaa ggactcgccc    120
ctgccttggg gaatcccagg gaccgtcgtt aaactcccac taacgtagaa cccagagatc    180
gctgcgttcc cgcccctca cccgcccgct tcgtcatca ctgaggtgga gaagagcatg    240
cgtgaggctc cggtgcccgt cagtgggcag agcgcacatc gcccacagtc cccgagaagt    300 tgggggagg ggtcggcaat tgaaccggtg cctagaaag gtggcgcggg gtaaactggg    360
aaagtgatgt cgtgtactgg ctccgccttt ttcccgaggg tggggagaa ccgtatataa    420 gtgcagtagt cgccgtgaac gttcttttc gcaacgggtt tgccgccaga acacaggtaa    480
gtgccgtgtg tggttcccgc gggcctggcc tctttacggg ttatggccct tgcgtgcctt    540
```

```
gaattacttc cacgccctg gctgcagtac gtgattcttg atcccgagct tcgggttgga      600
agtgggtggg agagttcgag gccttgcgct taaggagccc cttcgcctcg tgcttgagtt      660
gaggcctggc ctgggcgctg ggccgccgc gtgcgaatct ggtggcacct tcgcgcctgt      720
ctcgctgctt tcgataagtc tctagccatt taaaatttt gatgacctgc tgcgacgctt       780
tttttctggc aagatagtct tgtaaatgcg ggccaagatc tgcacactgg tatttcggtt      840
tttggggccg cgggcggcga cggggcccgt gcgtcccagc gcacatgttc ggcgaggcgg      900
ggcctgcgag cgcggccacc gagaatcgga cgggggtagt ctcaagctgg ccggcctgct      960
ctggtgcctg gccctcgcgcc gccgtgtatc gccccgccct gggcggcaag gctgcccgg      1020 tcggcaccag ttgcgtgagc ggaaagatgg ccgcttcccg gccctgctgc agggagctca     1080
aaatggagga cgcggcgctc gggagagcgg gcgggtgagt cacccacaca aaggaaaagg     1140
gcctttccgt cctcagccgt cgcttcatgt gactccacgg agtaccgggc gccgtccagg     1200
cacctcgatt agttctcgag cttttggagt acgtcgtctt taggttgggg ggaggggttt      1260
tatgcgatgg agtttcccca cactgagtgg gtggagactg aagttaggcc agcttggcac     1320
ttgatgtaat tctccttgga atttgccctt tttgagtttg gatcttggtt cattctcaag      1380
cctcagacag tggttcaaag ttttttttctt ccatttcagg tgtcgtgaaa actacccta     1440 aaagccaaaa                                                            1450

<210> SEQ ID NO 6
<211> LENGTH: 1330
<212> TYPE: DNA
<213> ORGANISM: Artificial Sequence
<220> FEATURE:
<223> OTHER INFORMATION: Homo sapiens ACTB promoter

<400> SEQUENCE: 6
gagatgtcca cacctaggat gtcccgcggt gggtgggggg cccgagagac gggcaggccg       60
ggggcaggcc tggccatgcg gggccgaacc gggcactgcc cagcgtgggg cgcggggcc      120 acggcgcgcg cccccagccc ccgggcccag caccccaagg cggccaacgc caaaactctc     180
cctcctcctc ttcctcaatc tcgctctcgc tctttttttt tttcgcaaaa ggagggggaga     240 gggggtaaaa aaatgctgca ctgtgcggcg aagccggtga gtgagcggcg cggggccaat     300
cagcgtgcgc cgttccgaaa gttgcctttt atggctcgag cggccgcggc ggcgccctat     360
aaaacccagc ggcgcgacgc gccaccaccg ccgagaccgc gtccgccccg cgagcacaga     420
gcctcgcctt tgccgatccg ccgcccgtcc acacccgccg ccaggtaagc ccggccagcc     480
gaccggggca ggcggctcac ggcccggccg caggcggccg cggccccttc gccgtgcag    540 agccgccgtc tgggccgcag cggggggcgc atggggggg aaccgaccg ccgtgggggg      600 cgcgggagaa gcccctgggc ctccggagat gggggacacc ccacgccagt tcggaggcgc      660
gaggccgcgc tcgggaggcg cgctccgggg gtgccgctct cggggcgggg gcaaccggcg     720
gggtctttgt ctgagccggg ctcttgccaa tgggatcgc agggtgggcg cggcggagcc     780
cccgccaggc ccggtggggg ctgggcgcc attgcgcgtg cgcgctggtc ctttgggcgc     840
taactgcgtg cgcgctggga attggcgcta attgcgcgtg cgcgctggga ctcaaggcgc    900
taactgcgcg tgcgttctgg ggccggggt gccgcgcct gggctgggc gaaggcgggc     960 tcggccggaa ggggtgggg tcgccgcggct cccgggcgct tgcgcgcact tcctgcccga     1020
gccgctggcc gccgagggt gtggccgctg cgtgcgcgcg cgccgacccg cgctgtttg     1080 aaccgggcgg aggcggggct ggcgcccggt tgggaggggg ttggggcctg gcttcctgcc    1140
```

```
gcgcgccgcg gggacgcctc cgaccagtgt ttgcctttta tggtaataac gcggccggcc   1200
cggcttcctt tgtccccaat ctgggcgcgc gccggcgccc cctggcggcc taaggactcg   1260
gcgcgccgga agtggccagg gcggggggcga cctcggctca cagcgcgccc ggctattctc   1320
gcagctcacc                                                          1330

<210> SEQ ID NO 7
<211> LENGTH: 665
<212> TYPE: DNA
<213> ORGANISM: Artificial Sequence
<220> FEATURE:
<223> OTHER INFORMATION: Homo sapiens GAPDH promoter

<400> SEQUENCE: 7
ttcatccaag cgtgtaaggg tccccgtcct tgactcccta gtgtcctgct gcccacagtc     60
cagtcctggg aaccagcacc gatcacctcc catcgggcca atctcagtcc cttcccccct    120 acgtcgggc ccacacgctc ggtgcgtgcc cagttgaacc aggcggctgc ggaaaaaaaa    180
aagcggggag aaagtagggc ccggctacta gcggttttac gggcgcacgt agctcaggcc    240
tcaagacctt gggctgggac tggctgagcc tggcgggagg cggggtccga gtcaccgcct    300
gccgccgcgc ccccggtttc tataaattga gcccgcagcc tcccgcttcg ctctctgctc    360
ctcctgttcg acagtcagcc gcatcttctt ttgcgtcgcc aggtgaagac gggcggagag    420
aaacccggga ggctagggac ggcctgaagg cggcaggggc gggcgcaggc cggatgtgtt    480
cgcgccgctg cggggtgggc ccgggcggcc tccgcattgc aggggcgggc ggaggacgtg    540
atgcggcgcg ggctgggcat ggaggcctgg tggggagggg gaggggaggc gtgtgtgtcg    600
gccggggcca ctaggcgctc actgttctct ccctccgcgc agccgagcca catcgctcag    660
acacc                                                              665

<210> SEQ ID NO 8
<211> LENGTH: 1143
<212> TYPE: DNA
<213> ORGANISM: Artificial Sequence
<220> FEATURE:
<223> OTHER INFORMATION: Homo sapiens RPL10 promoter

<400> SEQUENCE: 8
gtgcgctcga gcaggattc ctcccgtcct tcctgtcaaa ggacgggaag actttgttac     60
cccaccgcgc cccacctgca gaatggtgga cagataccte cagatgccac ttcccccagg    120
acgcccgcct gctctgcgca cctctccccg gatgctgccc cgtgggcggg tgggggcggc    180
cctgcttccc cacgaccccc agacgcaccc ggagggactc ttgagcacag tggagtggga    240
agggcgaggt ggggcggtgc ccaggcgaga gcggctcatg ggaggcggcg cccgagacgc    300
agctggtcgg gacggtgcgg gtcagggtgg gcggagcggg gctagagatg ccccgggggtt    360 tcccaggcca tgagtctccg tggagatttc tcctcgacct cttccccgcg gcaatgtgcg    420
aaccctgggt ctccaggaaa cggggatacg gggcatggct cccagcaagg cctggtccag    480
cctctccggt agggaatgg gtctccccct ccggcctccc gggttgacaa aggaacgcgg    540
gcccagatcc ccgtatggcg cttcaccgcc ggggcctcta gctagaagg aggcacggag    600 cgcgtgtccg agaccgtgc aagctcaggg acactctcgc ggtcgccggg aggcccacct    660
agggtacttt ccttttttcc actctcagaa atatacgtct gtcacagtta acggcaaagc    720
ctagggcaag agttctacgc ccaagatggc cagccggaag cgggcttctc gcgaccatgt    780
ggcgaagccc cattcgtcag ctggccgccc gcggccctgg tacccggtca cctctctgat    840
```

| ctgcgcatgt gctgggctac gcccgggcgc aagcgccaag agcggctgcg tctatggtca | 900 |
| tgacgtctga cagagcgtcc acccgtcttc gacaggactc tatggttctt acgcgcgcag | 960 |
| acagaccgcc tatataagcc atgcgcaggc ggaggagcgc ctctttccct tcggtgtggt | 1020 |
| gagtaagcgc agttgtcgtc tcttgcgtg ccgttgctgg ttctcacacc ttttaggtct | 1080 |
| gttctcgtct tccgttccga ctctctcttt ttcgttgcag ccactgaaga tcctggtgtc | 1140 |
| gcc | 1143 |

<210> SEQ ID NO 9
<211> LENGTH: 1538
<212> TYPE: DNA
<213> ORGANISM: Artificial Sequence
<220> FEATURE:
<223> OTHER INFORMATION: Homo sapiens LENG8 promoter

<400> SEQUENCE: 9

| ttgtatcaga gtcctggacg gaaacagatg gcactcaaaa ggtggcgcgc agttcagaga | 60 |
| aatgcctatg tacggatttg gtccaatgcc tcagcctgac ctcagggacc ttcgggggtc | 120 |
| tgctccgcgc ccaccttac acatctgtga ccccacacac ttccacccca gcgccactgc | 180 |
| caacagctac acccatcccc ctccaaccgc gtcagcttcc agcctcggtc catctgaact | 240 |
| cgccgtgccc cctcccctgc gcccttccag attcatttgc tagggaagcc cgtctcttccg | 300 |
| ggtggagctg ttcctcatcc cctttctta tcattctctc cccagggctt ccacatcacc | 360 |
| gtgctgtgga caatcccgga actcctgtca cgccagttta catttaggaa cagtaatggc | 420 |
| tcccactgac tcagtcaaaa caaggctgcg gccgggcacg gtggctcacg cccgtaatcc | 480 |
| cagcactttg ggaagccgag acggaggat cacgaggtca ggagttcgag aacagcctgg | 540 |
| ccgacatggt gaaaccccgt ctttacaaaa acacaaaaat tagccgggca tagtggcgcg | 600 |
| cgcctgtaat cccagctact ccggaggctg aggcagaatt gtttgaaccc aggaggcgga | 660 |
| ggttgcagtg agcagagatc acgccactgt actctatcgt gggcgacgac agagcaagag | 720 |
| caagactccg tctccgagaa caacaacaac agcaacaaga aaacaacaat aaaaaaaata | 780 |
| aggctgcgtg ggaggcagaa agagctaatg cggccacgct tgtccctcg gggccaccgt | 840 |
| ccccacccag acttccggtc tgccttaaaa tgttcatgcg taagtgcgtg ggcaggaagg | 900 |
| cgggctcaag cgcagctcgt ggcgttcatt ggctgtgcag ggcgaggga ggcggtgcaa | 960 |
| ggccgccgcg tgacgtcagg acgccgcggt caggacgtcg aagccaaaga agaccagagc | 1020 |
| cagccgggtg gcacagcggt gtcgtggccg tgttgctgat cgcctgggtg gttgttggcg | 1080 |
| tgtccctgca gcgaaggatc ctggttggta aggggagcgg cgggcgagca ggcgggcggg | 1140 |
| gatagcatct cctttggtc ttgcgccccg cgagccccga ggccttctcg gccgtcgcag | 1200 |
| cagcagacgc cgcgcgcgag cgtcgacagg gtgtggcggc gcaggggcag ccactgcgcc | 1260 |
| tgcgcaccgg gcctggggcc gcgcgttcgg gcactagcgc gcgtgcgccg tcgtcttcta | 1320 |
| ctttccacac ccagaactct tcagatcctt gacccccagtg gcttttcagt cagcctcccc | 1380 |
| tttttctgccc agcttctctt gagtccatct acttttcttc cccactttgt gacgtgtttt | 1440 |
| tagctccccc ttaagtctcc ctaactcatt ctttttctca taggcagtga aaaagcagtc | 1500 |
| tggctcccga ggtccacccc ttataccca aggtccag | 1538 |

<210> SEQ ID NO 10
<211> LENGTH: 691
<212> TYPE: DNA
<213> ORGANISM: Artificial Sequence
<220> FEATURE:

<223> OTHER INFORMATION: Homo sapiens SNX3 promoter

<400> SEQUENCE: 10

| aatccagacg | cgtgtctggt | gcaacgctcg | ggtttatggc | aaaatcatct | caggcatttg | 60 |
| cttaaccttc | tccagaaagg | cattttcagg | ggttcacagt | gagacggtgc | acaggttggc | 120 |
| acagagttag | taggggcagt | tttgtttcga | tttgcgggca | aatctctaag | atctctccgt | 180 |
| ttaactttcg | cccgcaattc | ccaaagccgc | taaagccgtt | tccggcgctc | taccccgccg | 240 |
| caggccgagg | ctggcgcaga | gagacaggaa | gcgccagctc | tgggcgtctg | gtcctcgcc | 300 |
| tcctcggccg | cagccccgcg | gcggcgcgct | cgcggtgcat | tgtgggcgct | gtagtccggc | 360 |
| cggaacctgt | ttgcgacccc | gagtcccatg | acaccgcttc | tcctcacacc | ccagtccgca | 420 |
| gtgcccctcc | ccagcctcgg | ccgggcctcc | cgggagccgg | gcgtggcgtt | ccagctagtg | 480 |
| agccgtttct | cccctgggct | cggaggcgga | agcttgaggg | gcgcggggag | gagcttcgcg | 540 |
| tgcggggtga | acgcccgctc | tacgtgctcg | ttctcttcgc | gaccgctgcg | cgcgagcccc | 600 |
| gtgtccccac | ggcgggcagc | agcggcggcg | gcggcggctg | aacgcggagg | gggcggaggg | 660 |
| agcccgcggc | ggcggcagca | gctacagcga | a | | | 691 |

<210> SEQ ID NO 11
<211> LENGTH: 1022
<212> TYPE: DNA
<213> ORGANISM: Artificial Sequence
<220> FEATURE:
<223> OTHER INFORMATION: Homo sapiens CNOT3 promoter

<400> SEQUENCE: 11

| gtagctcctc | ccccagacca | attgttttaa | gagaggggggg | cggatacatc | caatcagcac | 60 |
| gacacaggtc | tcttgattga | cgttcgggtc | ctcgcgctgg | cgtgttgtgc | cctgaggcgg | 120 |
| gaggaggagg | aggagcgggg | aggaaaaacct | gagccaatcc | tagcagcctg | cgcgggaggc | 180 |
| caatcgaacg | ccgcgccttg | gagcgatcac | ccaatccgcg | aaaggggggca | gggcgcatcc | 240 |
| ctgccaggaa | ccaatagaaa | gcctccaagg | gtcaggagcg | acgttcagca | ggagcaatga | 300 |
| ctggcctata | ttcgggactc | gggggcgggt | cggcgccaga | gacgagaaga | gaggagggga | 360 |
| ggcctcctcc | gccgccgcca | tcttggaccg | ggcccggtca | gcttccgcgg | agccatcggc | 420 |
| agacgccgcg | gcctcccttg | agccccgacc | cccgtcgtca | gaacaacccc | gggcccactc | 480 |
| ccccaacccc | acttccgctt | cgcgccgcta | tcgcgatagc | gcccgggccc | ggggcgcgag | 540 |
| aaaaaggcgg | cgggcgctcg | cctccccgc | ctgtcgcgat | acgctcctca | gcggcggcgc | 600 |
| cagctcctgt | ggtgagagcg | tcaggctcga | ctgggccgga | cccttccct | tcctccccc | 660 |
| ggcgccatcg | gccgcccctcc | ccgccgcctc | ccgccctggc | gacaccgccg | tctgtcgcga | 720 |
| catggcctcc | cctcgcctgc | ccctgccgc | cgcctctgca | gcgcggggct | cccggcgggg | 780 |
| ggcggctccc | tccctctcgc | cctcccgttc | ctgcgcctct | ttcacgttcc | ttggggctgg | 840 |
| tctcttgtca | gatagcaaat | gcttcttctc | tttaccagtc | ccacctacct | cactatgctg | 900 |
| actaggtcca | tgtctctggg | ttttaccag | ccagggaata | cgtgttaatt | cctctccaat | 960 |
| ctctcctagc | agcgtccgtc | tccaagagag | tatgaagaga | gtgcgtctgt | agggcaggga | 1020 |
| ag | | | | | | 1022 |

<210> SEQ ID NO 12
<211> LENGTH: 1175
<212> TYPE: DNA
<213> ORGANISM: Artificial Sequence
<220> FEATURE:

<223> OTHER INFORMATION: Homo sapiens CPNE1 promoter

<400> SEQUENCE: 12

```
gtccatttaa tcctcaaaaa acttagaggt aagcacaatt cgctccttcc gcggaaactg      60
gaagacgtga agcaatttgc acagtcttgc agtgaagggc caagctagac actcatacccc    120
agcccacccg ccagggccac tagcccaagg tcggtcctgt gcgccaacag tcgcaagcag    180
ggactgaata tcccccctctt agcacaaaac ccagtaactt ccgggagatc gcccgagacc   240
gtcagcgcgc ttgcgcggcc ccttgacgtc aaccacgccg ttcctccccc ttctggaacg    300
cggagccgct gagcgggccg acggccattt tgtgaagcgg cgaaggaggt ggtggctgcg    360
ttgggctccg ggaagccgtt cgggctgggg ctgtcggccg cggggcggag gcactcgcgc    420
ggggggtaat tcggggtctg ggttctggtg ccgcgcagct ttccccggta agactcccgc    480
agcccctgaa cgggtggggc tgtgcgggc tcgtggtgcc ccttggtggc ccggggcggg    540
gccttcggag gccttcgagc ccgcggcaac tagcgcccca cacaaagggt cgaggcaggt    600
ctgcaggggg agtgggatgc cacttaggcc tctgagatct gagaggatgc aaggaggacg    660
caagaggatg agcctgcgta ccgaagtggg gacgaggcca tagcgaggac tccccgtgg    720
tctgagaggg ggcaggccag agctggctgg ctcagcggcc tgcgagctaa ccggggactg    780
cagtaaaaaa gctgtgaagc tgagctttat gactgttta attttcagtg gattcgttat    840
tgggctaagt taatgacact cttgtaaata tataattatt ttgagatact caaatttgaa    900
agcaatacca actaaaaagc atgtgtggga ttttgttacg gtgtctttct ttttttttt   960
tttttgata tgcattctaa tgaagtactc tggtggtttc agactcgcct tcgtaatgta    1020
cagtgtggcc tgtgcgtgtt gttttgtgtt tcctgcattg attttttgcct ccgtttattc   1080
tctattgcag tctaaaagtt ggttttaatt ggttgcccac aggattgact tggcctctac    1140
ttcttgttaa ggaaattcat ctcttgtttt atcag                              1175
```

<210> SEQ ID NO 13
<211> LENGTH: 416
<212> TYPE: DNA
<213> ORGANISM: Artificial Sequence
<220> FEATURE:
<223> OTHER INFORMATION: Homo sapiens HYPO promoter

<400> SEQUENCE: 13

```
tcttttacac gtttggtttt atggtccgtt ggaggttttt tcacgctgag ggtgaagatt      60
cttagtttcc tcaattagca taaaagctgc tccaaggctg ctgagtcttc agttccattc    120
cattcaaaat gttaattcct gagacacgca acctacgccc tactgtcctt tgtcccacgg    180
cttctcgaga ttatctctgt gttttaatag ataaaacgcc ttctctcccc acccgtgggg   240
tgcaaagcac agcgcatggg gctggtggcg cccgagagca acacacaacg catgcgccag    300
tccgcaggtg tgggcggagg agaaatcgcg tcggcggcag gggatgacgt aaaaaggccg   360
cgctgtactg cggcttgtgc cgcttccgca agaaggtttc ctggcctgtt gcagcc         416
```

<210> SEQ ID NO 14
<211> LENGTH: 564
<212> TYPE: DNA
<213> ORGANISM: Artificial Sequence
<220> FEATURE:
<223> OTHER INFORMATION: Homo sapiens DKC1 promoter

<400> SEQUENCE: 14

```
gcacactact cctattggcc atctgctcta gctggatggg aactgcaagc agcaaaggcc      60
```

```
tttcaacctc tccgagcttc aacatgttca cttatgcatc aggactgatc caacagcaac    120
ctgaaagggt cggtgtgaga aagcaaagaa agaggtactg tttacggagc gttcagccgt    180
gagcccaggc gcaggcgcgg agctaaaccc ggaggtgaag caactacagc tggggccacg    240
cccacagact ccgggctgtc ggggcgggcg gcactcgcgc ttccagcctg gccaaccag     300 gctgcttgag gctcgaagcg catgcgcggt ctcgccctcc gtactggccg agccagcaaa    360
tcgcattgcg cagacgacca gcgggcgcct cggattccgc cccgggatg gccccgcctc     420 ctcccgcccc gcggcaaggc acgcacaggg cagtgcgcgg gtgggtgggt cctagcagcg    480
cggcctgacg ggaccaaggc ggcgggagtc tgcggtcgtt ccctcggctg tggaccgggc    540
ggcacgcacg cggtgcaggg taac                                          564

<210> SEQ ID NO 15
<211> LENGTH: 509
<212> TYPE: DNA
<213> ORGANISM: Artificial Sequence
<220> FEATURE:
<223> OTHER INFORMATION: Homo sapiens VPS72 promoter

<400> SEQUENCE: 15
acaaaaatta gttgggcatg gtggcgggcg cctgtaatcc cagctactcg ggggactgag     60
gcaggagaat cgcttcagcc cggggacgg aggttgcagt gagccgagat cgtgccactg     120
cactccagtc tggcgacaga gcgaggcgag actccgtccc tacgaaaaaa aaaaaccata    180
tatatatata aaataaaaat aaataaaata aaatgtgttg acttagggtt atggggtgtct   240 tcgtaccacc aagtggactc attgagcaag ggagatcgct gggtactaga gcaagcggcc    300
tagagcatcc gcgcaggagt aggagaggct gaagagtaaa gagggtttag agggtgggac    360
tgggagtctc tcgacactct gttacttctg cctgtaaacg cccgacttcc gccgctggtg    420
gccacccgca ggtagtgatg tcgagcgtcg agctcccaaa accgagctgg tgagggctg     480 caggtggcgg cgcagtctcg gtaggcggt                                      509

<210> SEQ ID NO 16
<211> LENGTH: 654
<212> TYPE: DNA
<213> ORGANISM: Artificial Sequence
<220> FEATURE:
<223> OTHER INFORMATION: Homo sapiens IT6B4BP promoter

<400> SEQUENCE: 16
tctgtccctc aaggcacagc tgactcatcc ctttcccca aacctgccct tcctccggct      60
tcatttccat caatacctcc atcatcaacc cttccgcgag acactcctgg cccctcctct    120
ccctcatgcc tcacaaccga ccagccgag gtctaggtcg atgacagctc ctaaaaagct     180
cctgaatgaa taatgaatga atgaacgcga gcaggctagg cgtggggcca ggcggggtcg    240
cgcccagacc gctcgcgacc atagagtccg ccggaggccg gaggtagagg ggctggatgc    300
gtggcgggga gcgccgggct ctcccggaag tctccctgga cggaagtgga aacggaaacc    360 ttttttaggga gtccaaggta cagtcgccgc gtgcggagct tgttactggt tacttggtaa    420
gctggtgtga ggggaacctg ggagggtcag ctccggtcct gggtcgggag gggtgggggc    480
cagaggattc agggcggag gttctggtgg gggcccagtg ggcgggaccc gaggacggag     540
gggccgggag gccgagaggg gcggggtcgc ggcggggcct gagggacgga ggccgggata    600
cttgggaaag gatccgccgg ccttgaactc ccgcctccgc cgcccctagg cctc          654

<210> SEQ ID NO 17
```

<211> LENGTH: 567
<212> TYPE: DNA
<213> ORGANISM: Artificial Sequence
<220> FEATURE:
<223> OTHER INFORMATION: Homo sapiens UQCRQ promoter

<400> SEQUENCE: 17

```
gtcaccttttt tgttccctcc cccgcctccc gcattcggcc gcttcctgac tgggattcca      60
cagaaaagcc gagggctgag gagaagtgtg agcgcctccg cctgtccact gtccccaaa      120
gtcagttcaa tccccgacgt cctccgctag gctccacccc accggcccgg gcagggcctc     180
caaggcacct cccacctacg ggtcacccag tcagcccact tctttctggg acaaaggcgt     240
catcccttag agacagtagg aaaatggtat ctcccggaag ttacctcacg acctccaaga     300
gcggcttcca accttgccgg aaatgacgaa cgagtcaacc ggatcggtga ctgtggaggg     360
cgagctgagc cctgtgcgtg agtggggtct ggttgtgcag tgttcgtgga ccctgggagg     420
ctaggggcgc cccgctgggc tgggaaagga taaggagtgc aggggcagga gtctggggtt     480
ggggatggac cccgcggggg actgcggcgc ttcgcgaaag cgagccaagc gcctgtccac     540
cctcggtcct gcagggccgc cgccaca                                          567
```

<210> SEQ ID NO 18
<211> LENGTH: 22
<212> TYPE: DNA
<213> ORGANISM: Artificial Sequence
<220> FEATURE:
<223> OTHER INFORMATION: ME5 primer

<400> SEQUENCE: 18

```
acgcgtgcaa ggcatggaaa aa                                               22
```

<210> SEQ ID NO 19
<211> LENGTH: 35
<212> TYPE: DNA
<213> ORGANISM: Artificial Sequence
<220> FEATURE:
<223> OTHER INFORMATION: MP3 primer

<400> SEQUENCE: 19

```
acgcgtagat ctgaattcta cccgggcgac gcagt                                 35
```

<210> SEQ ID NO 20
<211> LENGTH: 21
<212> TYPE: DNA
<213> ORGANISM: Artificial Sequence
<220> FEATURE:
<223> OTHER INFORMATION: CMV5 primer

<400> SEQUENCE: 20

```
acgcgttgac attgattatt g                                                21
```

<210> SEQ ID NO 21
<211> LENGTH: 24
<212> TYPE: DNA
<213> ORGANISM: Artificial Sequence
<220> FEATURE:
<223> OTHER INFORMATION: KMD1 primer

<400> SEQUENCE: 21

```
tctagagcca aaacaaactc ccat                                             24
```

<210> SEQ ID NO 22
<211> LENGTH: 24
<212> TYPE: DNA

```
<213> ORGANISM: Artificial Sequence
<220> FEATURE:
<223> OTHER INFORMATION: KMD4 primer

<400> SEQUENCE: 22
gctagcggcc tccgcgccgg gttt                                            24

<210> SEQ ID NO 23
<211> LENGTH: 36
<212> TYPE: DNA
<213> ORGANISM: Artificial Sequence
<220> FEATURE:
<223> OTHER INFORMATION: KMD5 primer

<400> SEQUENCE: 23
acgcgtagat ctgaattcgt ctaacaaaaa agccaa                               36

<210> SEQ ID NO 24
<211> LENGTH: 41
<212> TYPE: DNA
<213> ORGANISM: Artificial Sequence
<220> FEATURE:
<223> OTHER INFORMATION: EEF1A1F primer

<400> SEQUENCE: 24
acgcgtgtaa gccagcaatg gtagagggaa gattctgcac g                         41

<210> SEQ ID NO 25
<211> LENGTH: 38
<212> TYPE: DNA
<213> ORGANISM: Artificial Sequence
<220> FEATURE:
<223> OTHER INFORMATION: EEF1A1R primer

<400> SEQUENCE: 25
ggatcctttt ggcttttagg ggtagttttc acgacacc                             38

<210> SEQ ID NO 26
<211> LENGTH: 30
<212> TYPE: DNA
<213> ORGANISM: Artificial Sequence
<220> FEATURE:
<223> OTHER INFORMATION: BApF primer

<400> SEQUENCE: 26
acgcgtgaga tgtccacacc taggatgtcc                                      30

<210> SEQ ID NO 27
<211> LENGTH: 27
<212> TYPE: DNA
<213> ORGANISM: Artificial Sequence
<220> FEATURE:
<223> OTHER INFORMATION: BApR primer

<400> SEQUENCE: 27
ggatccggtg agctgcgaga atagccg                                         27

<210> SEQ ID NO 28
<211> LENGTH: 26
<212> TYPE: DNA
<213> ORGANISM: Artificial Sequence
<220> FEATURE:
<223> OTHER INFORMATION: GAPDHF primer

<400> SEQUENCE: 28
acgcgtttca tccaagcgtg taaggg                                          26
```

```
<210> SEQ ID NO 29
<211> LENGTH: 28
<212> TYPE: DNA
<213> ORGANISM: Artificial Sequence
<220> FEATURE:
<223> OTHER INFORMATION: GAPDHR primer

<400> SEQUENCE: 29
gtttaaacgg tgtctgagcg atgtggct                                28

<210> SEQ ID NO 30
<211> LENGTH: 31
<212> TYPE: DNA
<213> ORGANISM: Artificial Sequence
<220> FEATURE:
<223> OTHER INFORMATION: RPLF primer

<400> SEQUENCE: 30
acgcgtaggc ccacctaggg tactttcctt t                            31

<210> SEQ ID NO 31
<211> LENGTH: 31
<212> TYPE: DNA
<213> ORGANISM: Artificial Sequence
<220> FEATURE:
<223> OTHER INFORMATION: RPLR primer

<400> SEQUENCE: 31
ggatccggcg acaccaggat cttcagtggc t                            31

<210> SEQ ID NO 32
<211> LENGTH: 31
<212> TYPE: DNA
<213> ORGANISM: Artificial Sequence
<220> FEATURE:
<223> OTHER INFORMATION: LENG8F1 primer

<400> SEQUENCE: 32
acgcgtagaa ttgtttgaac ccaggaggcg g                            31

<210> SEQ ID NO 33
<211> LENGTH: 33
<212> TYPE: DNA
<213> ORGANISM: Artificial Sequence
<220> FEATURE:
<223> OTHER INFORMATION: LENG8R1 primer

<400> SEQUENCE: 33
gtttaaacaa agtagaagac gacggcgcac gcg                          33

<210> SEQ ID NO 34
<211> LENGTH: 33
<212> TYPE: DNA
<213> ORGANISM: Artificial Sequence
<220> FEATURE:
<223> OTHER INFORMATION: LENG8F2 primer

<400> SEQUENCE: 34
gtttaaaccc acacccagaa ctcttcagat cct                          33

<210> SEQ ID NO 35
<211> LENGTH: 31
<212> TYPE: DNA
<213> ORGANISM: Artificial Sequence
<220> FEATURE:
<223> OTHER INFORMATION: LENG8R2 primer
```

```
<400> SEQUENCE: 35
gaattcctgg accttggggt ataagggtg g                                    31

<210> SEQ ID NO 36
<211> LENGTH: 30
<212> TYPE: DNA
<213> ORGANISM: Artificial Sequence
<220> FEATURE:
<223> OTHER INFORMATION: SNX3F primer

<400> SEQUENCE: 36
gaattcaatc cagacgcgtg tctggtgcaa                                     30

<210> SEQ ID NO 37
<211> LENGTH: 22
<212> TYPE: DNA
<213> ORGANISM: Artificial Sequence
<220> FEATURE:
<223> OTHER INFORMATION: SNX3R primer

<400> SEQUENCE: 37
ggatccttcg ctgtagctgc tg                                             22

<210> SEQ ID NO 38
<211> LENGTH: 37
<212> TYPE: DNA
<213> ORGANISM: Artificial Sequence
<220> FEATURE:
<223> OTHER INFORMATION: CNOT3F1 primer

<400> SEQUENCE: 38
acgcgtgtag ctcctccccc agaccaattg ttttaag                             37

<210> SEQ ID NO 39
<211> LENGTH: 37
<212> TYPE: DNA
<213> ORGANISM: Artificial Sequence
<220> FEATURE:
<223> OTHER INFORMATION: CNOT3R1 primer

<400> SEQUENCE: 39
ggatcctcca tccttccagc caggagccaa taccgac                             37

<210> SEQ ID NO 40
<211> LENGTH: 31
<212> TYPE: DNA
<213> ORGANISM: Artificial Sequence
<220> FEATURE:
<223> OTHER INFORMATION: CNOTF2 primer

<400> SEQUENCE: 40
agatcttggg gctggtctct tgtcagatag c                                   31

<210> SEQ ID NO 41
<211> LENGTH: 31
<212> TYPE: DNA
<213> ORGANISM: Artificial Sequence
<220> FEATURE:
<223> OTHER INFORMATION: CNOTR2 primer

<400> SEQUENCE: 41
ggatcccttc cctgccctac agacgcactc t                                   31

<210> SEQ ID NO 42
<211> LENGTH: 31
<212> TYPE: DNA
```

```
<213> ORGANISM: Artificial Sequence
<220> FEATURE:
<223> OTHER INFORMATION: CPNE1F1 primer

<400> SEQUENCE: 42
acgcgtgtcc atttaatcct caaaaaactt a                                      31

<210> SEQ ID NO 43
<211> LENGTH: 34
<212> TYPE: DNA
<213> ORGANISM: Artificial Sequence
<220> FEATURE:
<223> OTHER INFORMATION: CPNE1R1 primer

<400> SEQUENCE: 43
ggatcctttt tactgcagtc cccgttatta gctc                                   34

<210> SEQ ID NO 44
<211> LENGTH: 31
<212> TYPE: DNA
<213> ORGANISM: Artificial Sequence
<220> FEATURE:
<223> OTHER INFORMATION: CPNE1F2 primer

<400> SEQUENCE: 44
agatctagct gtgaagctga gctttatgac t                                      31

<210> SEQ ID NO 45
<211> LENGTH: 31
<212> TYPE: DNA
<213> ORGANISM: Artificial Sequence
<220> FEATURE:
<223> OTHER INFORMATION: CPNE1R2 primer

<400> SEQUENCE: 45
ggatccctga taaaacaaga gatgaatttc c                                      31

<210> SEQ ID NO 46
<211> LENGTH: 31
<212> TYPE: DNA
<213> ORGANISM: Artificial Sequence
<220> FEATURE:
<223> OTHER INFORMATION: HYPOF primer

<400> SEQUENCE: 46
acgcgttctt ttacacgttt ggttttatgg t                                      31

<210> SEQ ID NO 47
<211> LENGTH: 31
<212> TYPE: DNA
<213> ORGANISM: Artificial Sequence
<220> FEATURE:
<223> OTHER INFORMATION: HYPOR primer

<400> SEQUENCE: 47
ggatccggct gcaacaggcc aggaaacctt c                                      31

<210> SEQ ID NO 48
<211> LENGTH: 25
<212> TYPE: DNA
<213> ORGANISM: Artificial Sequence
<220> FEATURE:
<223> OTHER INFORMATION: DKC1F primer

<400> SEQUENCE: 48
acgcgtgcac actactccta ttggc                                             25
```

<210> SEQ ID NO 49
<211> LENGTH: 25
<212> TYPE: DNA
<213> ORGANISM: Artificial Sequence
<220> FEATURE:
<223> OTHER INFORMATION: DKC1R primer

<400> SEQUENCE: 49
gaattcgtta ccctgcaccg cgtgc                                     25

<210> SEQ ID NO 50
<211> LENGTH: 25
<212> TYPE: DNA
<213> ORGANISM: Artificial Sequence
<220> FEATURE:
<223> OTHER INFORMATION: VPS72F primer

<400> SEQUENCE: 50
acgcgtacaa aaattagttg ggcat                                     25

<210> SEQ ID NO 51
<211> LENGTH: 25
<212> TYPE: DNA
<213> ORGANISM: Artificial Sequence
<220> FEATURE:
<223> OTHER INFORMATION: VPS72R primer

<400> SEQUENCE: 51
gaattcaccg cctaccgaga ctgcg                                     25

<210> SEQ ID NO 52
<211> LENGTH: 27
<212> TYPE: DNA
<213> ORGANISM: Artificial Sequence
<220> FEATURE:
<223> OTHER INFORMATION: ITGB4BPF primer

<400> SEQUENCE: 52
acgcgttctg tccctcaagg cacagct                                   27

<210> SEQ ID NO 53
<211> LENGTH: 40
<212> TYPE: DNA
<213> ORGANISM: Artificial Sequence
<220> FEATURE:
<223> OTHER INFORMATION: ITGB4BPR primer

<400> SEQUENCE: 53
gtttaaacga ggcctagggg cggcggaggc gggagttcaa                     40

<210> SEQ ID NO 54
<211> LENGTH: 27
<212> TYPE: DNA
<213> ORGANISM: Artificial Sequence
<220> FEATURE:
<223> OTHER INFORMATION: UQCRQF primer

<400> SEQUENCE: 54
acgcgtgtca ccttttttgtt ccctccc                                  27

<210> SEQ ID NO 55
<211> LENGTH: 28
<212> TYPE: DNA
<213> ORGANISM: Artificial Sequence
<220> FEATURE:
<223> OTHER INFORMATION: UQCRQR primer

<400> SEQUENCE: 55
gtttaaactg tggcggcggc cctgcagg                                          28

<210> SEQ ID NO 56
<211> LENGTH: 22
<212> TYPE: DNA
<213> ORGANISM: Artificial Sequence
<220> FEATURE:
<223> OTHER INFORMATION: RGpA F primer

<400> SEQUENCE: 56 ggatccttt cctctgcca aa                                                  22

<210> SEQ ID NO 57
<211> LENGTH: 25
<212> TYPE: DNA
<213> ORGANISM: Artificial Sequence
<220> FEATURE:
<223> OTHER INFORMATION: RGpA R primer

<400> SEQUENCE: 57
actagtataa gagaagaggg acagc                                             25

<210> SEQ ID NO 58
<211> LENGTH: 38
<212> TYPE: DNA
<213> ORGANISM: Artificial Sequence
<220> FEATURE:
<223> OTHER INFORMATION: RPL F50 primer

<400> SEQUENCE: 58
acgcgtacgc gcgcagacag accgcctata taagccat                               38

<210> SEQ ID NO 59
<211> LENGTH: 37
<212> TYPE: DNA
<213> ORGANISM: Artificial Sequence
<220> FEATURE:
<223> OTHER INFORMATION: RPL F100 primer

<400> SEQUENCE: 59
acgcgttgac gtctgacaga gcgtccaccc gtcttcg                                37

<210> SEQ ID NO 60
<211> LENGTH: 38
<212> TYPE: DNA
<213> ORGANISM: Artificial Sequence
<220> FEATURE:
<223> OTHER INFORMATION: RPL F200 primer

<400> SEQUENCE: 60
acgcgtctgg ccgcccgcgg ccctggtacc cggtcacc                               38

<210> SEQ ID NO 61
<211> LENGTH: 39
<212> TYPE: DNA
<213> ORGANISM: Artificial Sequence
<220> FEATURE:
<223> OTHER INFORMATION: RPL F500 primer

<400> SEQUENCE: 61
acgcgtgtct cccctccgg cctcccgggt tgacaaagg                               39

<210> SEQ ID NO 62
<211> LENGTH: 39
<212> TYPE: DNA

```
<213> ORGANISM: Artificial Sequence
<220> FEATURE:
<223> OTHER INFORMATION: RPL F1000 primer

<400> SEQUENCE: 62
acgcgtgtgc gctcgagcag gatttcctcc cgtccttcc                           39

<210> SEQ ID NO 63
<211> LENGTH: 36
<212> TYPE: DNA
<213> ORGANISM: Artificial Sequence
<220> FEATURE:
<223> OTHER INFORMATION: RPL R TSS primer

<400> SEQUENCE: 63
ggatccgcgc tcctccgcct gcgcatggct tatata                              36

<210> SEQ ID NO 64
<211> LENGTH: 31
<212> TYPE: DNA
<213> ORGANISM: Artificial Sequence
<220> FEATURE:
<223> OTHER INFORMATION: LENG F50 primer

<400> SEQUENCE: 64
acgcgtgtga cgtcaggacg ccgcggtcag g                                   31

<210> SEQ ID NO 65
<211> LENGTH: 31
<212> TYPE: DNA
<213> ORGANISM: Artificial Sequence
<220> FEATURE:
<223> OTHER INFORMATION: LENG F100 primer

<400> SEQUENCE: 65
acgcgttggc gttcattggc tgtgcagggc c                                   31

<210> SEQ ID NO 66
<211> LENGTH: 31
<212> TYPE: DNA
<213> ORGANISM: Artificial Sequence
<220> FEATURE:
<223> OTHER INFORMATION: LENG F200 primer

<400> SEQUENCE: 66
acgcgtttgt cccctcgggg ccaccgtccc c                                   31

<210> SEQ ID NO 67
<211> LENGTH: 31
<212> TYPE: DNA
<213> ORGANISM: Artificial Sequence
<220> FEATURE:
<223> OTHER INFORMATION: LENG F1000 primer

<400> SEQUENCE: 67
acgcgtttgt atcagagtcc tggacggaaa c                                   31

<210> SEQ ID NO 68
<211> LENGTH: 33
<212> TYPE: DNA
<213> ORGANISM: Artificial Sequence
<220> FEATURE:
<223> OTHER INFORMATION: LENG R TSS primer

<400> SEQUENCE: 68
gtttaaacct ctggtcttct ttggcttcga cgt                                 33
```

<210> SEQ ID NO 69
<211> LENGTH: 42
<212> TYPE: DNA
<213> ORGANISM: Artificial Sequence
<220> FEATURE:
<223> OTHER INFORMATION: SCV3LB primer

<400> SEQUENCE: 69
ggatccctcg agcgataaaa taaaagattt tatttagtct cc        42

<210> SEQ ID NO 70
<211> LENGTH: 32
<212> TYPE: DNA
<213> ORGANISM: Artificial Sequence
<220> FEATURE:
<223> OTHER INFORMATION: SCV3LRI primer

<400> SEQUENCE: 70
gaattcgtcg actgaaagac ccccgctgac gg        32

<210> SEQ ID NO 71
<211> LENGTH: 24
<212> TYPE: DNA
<213> ORGANISM: Artificial Sequence
<220> FEATURE:
<223> OTHER INFORMATION: 3'LTR-1 primer

<400> SEQUENCE: 71
gctagcccct gtgccttatt tgaa        24

<210> SEQ ID NO 72
<211> LENGTH: 36
<212> TYPE: DNA
<213> ORGANISM: Artificial Sequence
<220> FEATURE:
<223> OTHER INFORMATION: NEWMCSF primer

<400> SEQUENCE: 72
acgcgtttaa accgcggaat tcggatccac atcgtg        36

<210> SEQ ID NO 73
<211> LENGTH: 36
<212> TYPE: DNA
<213> ORGANISM: Artificial Sequence
<220> FEATURE:
<223> OTHER INFORMATION: NEWMCSR primer

<400> SEQUENCE: 73
ctcgagatct aggcctcacg atgtggatcc gaattc        36

<210> SEQ ID NO 74
<211> LENGTH: 30
<212> TYPE: DNA
<213> ORGANISM: Artificial Sequence
<220> FEATURE:
<223> OTHER INFORMATION: eGFP5 primer

<400> SEQUENCE: 74
acgcgtggat ccatggtgag caagggcgag        30

<210> SEQ ID NO 75
<211> LENGTH: 30
<212> TYPE: DNA
<213> ORGANISM: Artificial Sequence

```
<220> FEATURE:
<223> OTHER INFORMATION: eGFP3 primer

<400> SEQUENCE: 75
ctcgagagat ctttacttgt acagctcgtc                                    30

<210> SEQ ID NO 76
<211> LENGTH: 27
<212> TYPE: DNA
<213> ORGANISM: Artificial Sequence
<220> FEATURE:
<223> OTHER INFORMATION: GP91F primer

<400> SEQUENCE: 76
ggatccatgg ggaactgggc tgtgaat                                       27

<210> SEQ ID NO 77
<211> LENGTH: 35
<212> TYPE: DNA
<213> ORGANISM: Artificial Sequence
<220> FEATURE:
<223> OTHER INFORMATION: GP91R primer

<400> SEQUENCE: 77
ggatccctcg agttagaagt tttccttgtt gaaaa                              35

<210> SEQ ID NO 78
<211> LENGTH: 37
<212> TYPE: DNA
<213> ORGANISM: Artificial Sequence
<220> FEATURE:
<223> OTHER INFORMATION: L1F primer

<400> SEQUENCE: 78
gctcttccgc tcacgtgtga tcaatttaaa tttcgaa                            37

<210> SEQ ID NO 79
<211> LENGTH: 37
<212> TYPE: DNA
<213> ORGANISM: Artificial Sequence
<220> FEATURE:
<223> OTHER INFORMATION: L1R primer

<400> SEQUENCE: 79
agcggaagag cttcgaaatt taaattgatc acacgtg                            37

<210> SEQ ID NO 80
<211> LENGTH: 63
<212> TYPE: DNA
<213> ORGANISM: Artificial Sequence
<220> FEATURE:
<223> OTHER INFORMATION: L2F primer

<400> SEQUENCE: 80
aggcctggtc accggccatt atggccacgt gatcatttaa atttgaagca tttatcaggg   60
tta                                                                 63

<210> SEQ ID NO 81
<211> LENGTH: 27
<212> TYPE: DNA
<213> ORGANISM: Artificial Sequence
<220> FEATURE:
<223> OTHER INFORMATION: L2R primer

<400> SEQUENCE: 81
tattcgcgcg tttcggtgat gaatatt                                       27
```

<210> SEQ ID NO 82
<211> LENGTH: 39
<212> TYPE: DNA
<213> ORGANISM: Artificial Sequence
<220> FEATURE:
<223> OTHER INFORMATION: BApF primer

<400> SEQUENCE: 82
gtcgacatta atgccggtga gtgagcggcg cggggccaa          39

<210> SEQ ID NO 83
<211> LENGTH: 32
<212> TYPE: DNA
<213> ORGANISM: Artificial Sequence
<220> FEATURE:
<223> OTHER INFORMATION: BApR primer

<400> SEQUENCE: 83
ggatccggtg gcgcgtcgcg ccgctgggtt tt                 32

<210> SEQ ID NO 84
<211> LENGTH: 27
<212> TYPE: DNA
<213> ORGANISM: Artificial Sequence
<220> FEATURE:
<223> OTHER INFORMATION: NeoF primer

<400> SEQUENCE: 84
agatctatgg gatcggccat tgaacaa                      27

<210> SEQ ID NO 85
<211> LENGTH: 29
<212> TYPE: DNA
<213> ORGANISM: Artificial Sequence
<220> FEATURE:
<223> OTHER INFORMATION: pAR primer

<400> SEQUENCE: 85
catatgtcat aatcagccat accacattt                    29

<210> SEQ ID NO 86
<211> LENGTH: 27
<212> TYPE: DNA
<213> ORGANISM: Artificial Sequence
<220> FEATURE:
<223> OTHER INFORMATION: SVpAF primer

<400> SEQUENCE: 86
ctcgagatgg gatcggccat tgaacaa                      27

<210> SEQ ID NO 87
<211> LENGTH: 28
<212> TYPE: DNA
<213> ORGANISM: Artificial Sequence
<220> FEATURE:
<223> OTHER INFORMATION: SVpAR primer

<400> SEQUENCE: 87
catatgagta atcagccata ccacattt                     28

EXPRESSION VECTORS WITH IMPROVED SAFETY

This is a non-provisional application which claims priority from U.S. Ser. No. 60/850,269 filed Oct. 10, 2006, and is incorporated herein by reference.

BACKGROUND OF THE INVENTION

1. Field of the Invention

The present invention provides expression vectors comprising internal promoters that can be used for expressing proteins of interest. In one embodiment, the present invention provides retroviral vectors comprising an enhancer-deleted U3 region.

2. Background Art

Gene transfer involves the transfer of genetic material to a cell, usually for transcription and expression. The method is ideal for protein expression as well as for therapeutic purposes. Various transfer methods are known, such as DNA transfection and viral transduction. Virally-mediated gene transfer is attractive due to the efficiency of transfer and high levels of transgene expression, as well as the potential for targeting particular receptors and/or cell types if needed through natural affinity or pseudotyping.

In particular, retroviral vectors are useful for longer term expression due to their ability to integrate into the cellular genome. Murine leukemia virus-based (MLV) vectors are the most common retroviral vector, with many backbone plasmids and packaging cell lines available to suit most applications (See e.g., Miller and Buttimore, *Mol. Cell. Biol.* 6:2895 (1986)). Like all "simple" retroviruses, e.g. retroviruses that only encode structural and enzymatic viral proteins and do not utilize viral accessory proteins, MLV vectors can only integrate into dividing cells. Other simple retroviruses potentially suitable for use as vectors include other members of the mammalian C-type viruses (e.g., murine stem cell virus, Harvey murine sarcoma virus and spleen necrosis virus), B type viruses (e.g., mouse mammary tumor virus), and D type viruses (e.g., Mason Pfizer monkey virus). Other retroviruses suitable for use as a retroviral vector of the invention include avian retroviruses (e.g., Rous sarcoma virus), spumaviruses (e.g., foamy viruses), and the HTLV-BLV viruses (e.g., HTLV-1).

Lentiviruses are a subgroup of retroviruses that express viral accessory proteins and are capable of infecting and integrating into non-dividing, as well as dividing, cells. Vectors derived from lentiviruses are ideal tools for delivering exogenous genes to target cells because of their ability to stably integrate into the genome of dividing and non-dividing cells and to mediate long-term gene expression (Gilbert et al., *Somat. Cell Mol. Genet.* 26:83 (2001); Mitrophanous et al., *Gene Ther.* 6:1808 (1999); Naldini et al., *Science* 272:263 (1996); Sauter et al., *Somat. Cell Mol. Genet.* 26:99 (2001)).

Lentiviruses have been isolated from many vertebrate species including primates, e.g., human and simian immunodeficiency viruses (HIV-1, HIV-2, SIV), as well as non-primates, e.g., feline immunodeficiency virus (FIV), bovine immunodeficiency virus (BIV), equine infectious virus (EIAV), caprine arthritis encephalitis virus (CAEV) and the visna virus. Of these, HIV and SIV are presently best understood. Among non-primate lentiviral vectors, vectors derived from FIV (Curran et al., *Curr. Top. Microbiol. Immunol.* 261:75 (2002)) and EIAV (U.S. Patent Application No. 2001/0044149) are best characterized.

There are two major safety aspects that have received considerable attention in the context of retroviral gene therapy, regardless of whether the vector is based on murine leukemia virus (MLV) or lentivirus. Specifically, they are the presence of replication competent retrovirus (RCR) and the incidence of insertional mutagenesis. The former problem has greatly been improved by the development of a minimum sized retroviral vector that contains no overlapping viral sequences between the vectors and the packaging genome. However, the latter possibility has recently raised serious concerns, mainly because of the three leukemia cases found in the X-SCID human trial (Hacein-Bey-Abina et al., *Science* 302:415 (2003)). The retrospective analysis of the first two leukemia cases revealed that the leukemia probably resulted from the retroviral integration into the chromosome and the subsequent activation of the LMO2 gene, located in close proximity to the integration site, by the long terminal repeat (LTR). Although it was argued that this vector-mediated tumorigenesis might be restricted to the X-SCID gene therapy case due to the particular nature of this disease and its gene, it is now clear that the safety of retroviral vectors needs further improvement to become a viable form of therapeutics in the real world.

There have been several approaches for reducing the probability of vector-mediated tumorigenesis. One approach is to remove the U3 region of the LTR (Yu et al., *Proc. Natl. Acad. Sci. USA* 83:3194 (1986); Hawley et al., *Proc. Natl. Acad. Sci. USA* 84:2406 (1987); Yee et al., *Proc. Natl. Acad. Sci. USA* 84:5197 (1987)). The retroviral LTR consists of U3, R, and U5 regions, and the U3 region contains the enhancer and promoter sequence that control gene expression (Sun et al., *J. Virol.* 69:4941 (1995); Wahlers et al., *Mol. Ther.* 6:313 (2002)). Therefore, the insertional activation by a vector can be reduced by removing the U3 region. In that case, an additional promoter should be supplied to the vector to drive the expression of the target gene because the U3-deleted vector no longer contains the promoter sequence in the LTR.

As discussed previously, the U3-inactivated retroviral vector needs an internal promoter for the expression of target gene. One of the most frequently used internal promoters in retroviral vectors is the human cytomegalovirus (HCMV) immediate-early (IE) promoter (Jaalouk et al., *Virol. J.* 3:27 (2006); pQCXIN available from BD Biosciences) or related ones such as CA (HCMV IE enhancer/chicken β-actin promoter) (Ramezani et al., *Mol. Ther.* 14:245 (2006)). However, the HCMV IE promoter is known to be rapidly inactivated in primary human cells, while it does not work for certain genes (Herweijer et al., *J. Gene Med.* 3:280 (2001)). Thus, commonly used promoters have been shown to decrease expression of heterologous genes, be inactive in certain cell types, and potentially activate LTR-driven transcription, all of which decrease the safety and efficacy of the retroviral vector.

Finally, U3-inactivated retroviral vectors have been associated with very low titers due to promoter suppression by commonly-used promoters, such as CMV and SV40, which reduce transcription of genomic RNA for packaging (Jaalouk et al., *Virol. J.* 3:27 (2006)) Indeed, MLV based U3-deleted vectors have been associated with titers up to four orders of magnitude less than the comparable MLV vector with intact U3 regions (Olson et al., *J. Virol.* 68:7060 (1994)). Thus, it is surprising to find promoters that are capable of both driving high levels of heterologous gene transcription as well as enabling high viral titers to be produced. Therefore, new promoters are needed to be developed for use as an internal promoter in the retroviral vector.

BRIEF SUMMARY OF THE INVENTION

The present invention provides expression vectors comprising a heterologous internal promoter. In one embodiment, the vector comprises a nucleotide sequence comprising a 5'LTR and a 3'LTR. In further embodiments, the enhancer element of the U3 region of the 3'LTR or both the 3'LTR and 5'LTR is deleted. In one embodiment, the vectors are plasmid vectors. In a further embodiment, the vectors are retroviral vectors comprising one or more enhancer-deleted U3 regions, and which further comprise an internal promoter operably linked to a heterologous gene such that the retroviral vector is capable of producing high viral titers and high levels of transcription of the heterologous gene. Such vectors would also comprise the cis-acting elements required for reverse transcription, packaging, etc., as is well known in the art for retroviral vectors. In another embodiment, the vectors encode a retroviral vector comprising one or more enhancer-deleted U3 regions.

In one embodiment of the invention, the internal promoter is a eukaryotic, prokaryotic or viral promoter. In a further embodiment, the internal promoter is a mammalian cellular gene promoter. In a further embodiment, the internal promoter is selected from RPL10 promoter (SEQ ID NO:8), LENG8 promoter (SEQ ID NO:9), SNX3 promoter (SEQ ID NO:10), UQCRQ promoter (SEQ ID NO:17), or ITGB4BP promoter (SEQ ID NO:16). In a further embodiment, the internal promoter is a fragment or variant of the full length promoter and is capable of driving high levels of transcription of the heterologous gene while the vector comprising the promoter is capable of producing high viral titers. In one embodiment, a vector comprising the fragment or variant of the promoter retains substantially the same ability to produce high viral titers and high levels of transcription as a vector comprising the wild-type promoter. In a further embodiment, the internal promoter consists essentially of the TATA box.

In some embodiments, the internal promoter further comprises splicing sites for high levels of gene expression. In another embodiment, the vector is a retroviral vector that further comprises additional sequences, including polyadenylation sites, insulator sequences, splicing sites, an internal ribosomal entry site (IRES) and other transcriptional and translational effector sequences as is well known in the art.

In another embodiment, the vector is a plasmid comprising DNA encoding the retroviral vector comprising a 3' LTR with an enhancer-deleted U3 region. In another embodiment, the plasmid encodes a vector with enhancer-deleted U3 regions in both the 5' and 3' LTRs. In a further embodiment, an infectious retroviral particle encapsulating the vector RNA comprising enhancer-deleted U3 regions in both LTRs is provided. In another embodiment, the vector is in either RNA or DNA form, with one or both U3 regions being enhancer-deleted.

In another embodiment, the heterologous gene encodes a transcript of interest. In a further embodiment, the transcript of interest is a biologically active transcript, such as, but not limited to, a small interfering RNA, a ribozyme, an antisense RNA, or a decoy RNA. In a further embodiment, the heterologous gene encodes a polypeptide. The polypeptide may be any desired protein, e.g., a therapeutic protein or a marker protein. In one embodiment, the heterologous gene encodes eGFP or gp91.

A composition comprising the vector and suitable carriers is also provided. The composition may be suitable for in vivo administration.

A cell comprising the vector of the invention is provided, including target cells transformed with the vector or producer cells comprising the vector and additional sequences encoding factors required for the generation of infectious particles, such as retroviral env, and gag-pol, and other factors as needed. The target cells and producer cells may be any suitable eukaryotic cell type, such as mammalian cells. In a further embodiment, the cells may be of human, primate or murine origin. The cells may be primary cells or cell lines.

The present invention also provides for a method of producing infectious retroviral particles comprising cultivating a producer cell line comprising the retroviral vector as described above or a plasmid encoding the retroviral vector, collecting the supernatant, and filtering the medium to obtain a cell-free viral supernatant. The packaging cell line used for construction of a producer cell line may be any currently known in the art or one generated by transferring genes encoding the necessary viral proteins into a cell line such that once the retroviral vector, which comprises the packaging signal, is transcribed in the cell, the retroviral vector is packaged in infectious particles.

The present invention also provides for a method of transducing target cells comprising contacting said cells with the viral supernatant prepared as described above and comprising infectious retroviral particles according to the invention. The target cell, as described above, may be, but is not limited to, mammalian cells, human cells, primate cells, or murine cells. The target cells may be primary cells or cell lines.

The present invention further provides for a method of treating a subject comprising administering a composition comprising the vector of the invention and a suitable carrier, wherein the heterologous gene encodes a therapeutically useful polypeptide or transcript. In a further embodiment, the method is for treating a genetic disorder, a proliferation disorder, or an infectious disease.

The present invention also provides kits comprising the polynucleotides and vectors of the invention.

BRIEF DESCRIPTION OF THE DRAWINGS/FIGURES

FIG. 1 is a schematic of the enhancer-deleted U3 retroviral vectors pMT and pI-D.

FIG. 2 is a schematic of the enhancer-deleted U3 retroviral vector pI-ND.

FIG. 3 is a schematic of the enhancer-deleted U3 retroviral vector pI-LND-n.

FIG. 4 shows the levels of heterologous gene expression (gp91) of enhancer-deleted U3 retroviral vectors comprising the indicated promoters. The control is MT-gp91-n vector.

FIG. 5 shows the promoter sequence for GAPDH (SEQ ID NO:7).

FIG. 6 shows the promoter sequence for RPL10 (SEQ ID NO:8).

FIG. 7 shows the promoter sequence for LENG8 (SEQ ID NO:9).

FIG. 8 shows the promoter sequence for SNX3 (SEQ ID NO:10).

FIG. 9 shows the promoter sequence for ITGB4BP (SEQ ID NO:16).

FIG. 10 shows the promoter sequence for UQCRQ (SEQ ID NO:17).

DETAILED DESCRIPTION OF THE INVENTION

The invention relates to expression vectors comprising a heterologous internal promoter. In one embodiment, the vector is a retroviral vector comprising an enhancer-deleted U3 region in one or both LTRs with a heterologous promoter operably linked to a heterologous gene and which is capable of high levels of transcription of the heterologous gene and high viral titers. In another embodiment, the vector encodes a retroviral vector comprising an enhancer-deleted U3 region in one or both LTRs.

The Vector

As used herein, the term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles.

As used herein, the term "vector" refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors in RNA or DNA form. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCMVDsRed2-express, pIRES2-DsRed2, pDsRed2-Mito, and pCMV-EGFP available from Clontech. Many other vectors are well-known and commercially available. The insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

As described previously, the retroviral vector of the present invention or the retroviral vector encoded by a vector of the present invention may be based on simple retroviruses, such as MLV, lentiviruses, such as HIV, or any other retrovirus. These vectors retain the cis elements required for production of infectious particles. Such elements include a packaging signal located adjacent to the 5' LTR of the retroviral genome which is required for encapsidation of the viral RNA into the viral capsid or particle. Several retroviral vectors use the minimal packaging signal (also referred to as the psi [ψ] sequence) needed for encapsidation of the viral genome. Additional cis elements are well known in the art, such as the primer binding site, the polypurine tract and other sequences, and are included in the retroviral vector. However, sequences encoding viral proteins are removed from the vector such that no full-length viral protein is expressed. Any viral proteins required for the production of infectious particles are provided in trans by the packaging constructs.

The vector may further comprise sequences such as polyadenylation sequence, insulator sequences, splicing sites, IRES and other transcriptional and translational effector sequences.

The term "polyadenylation site", "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in the present vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation. Suitable polyadenylation sequences of the present invention also include, but are not limited to the bovine growth hormone (bGH) polyadenylation signal, the β-globin polyA site, and herpes simplex virus thymidine kinase polyA site (Sambrook et al., *Molecular Cloning: A Laboratory Manual,* 2nd ed., Cold Spring Harbor Laboratory Press, New York, pp. 16.7-16.8 (1989)).

Vectors of the present invention may also contain additional nucleic acid sequences, such as an intron sequence, splicing sequences, a localization sequence, or a signal sequence, sufficient to permit a cell to efficiently and effectively process the protein expressed by the nucleic acid of the vector. Examples of intron sequences include the β-globin intron and the human EF-1α intron (U.S. Pat. No. 7,049,143). Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York, pp. 16.7-16.8 (1989)).

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., *Biochem.* 76:801 (1994); Meyer et al., *J. Virol.* 69:2819 (1995); Jang et al., *J. Virol.* 62:2636 (1998); Haller et al., *J. Virol.* 66:5075 (1995)). Vectors incorporating IRESs may be assembled as is known in the art. For example, a vector containing a polycistronic sequence may contain the following elements in operable association: internal promoter, heterologous gene, an internal ribosome entry site and a second heterologous gene.

Such additional sequences are inserted into the vector such that they are operably linked with the promoter sequence, if transcription is desired, or additionally with the initiation and processing sequence if translation and processing are desired. Alternatively, the inserted sequences may be placed at any position in the vector.

Standard techniques for the construction of the vectors of the present invention are well-known to those of ordinary skill in the art and can be found in such references as Sambrook et al., *Molecular Cloning: A Laboratory Manual,* 2nd ed., Cold Spring Harbor Laboratory Press, New York, (1989). A variety of strategies are available for ligating fragments of DNA, the choice of which depends on the nature of the termini of the DNA fragments and which choices can be readily made by the skilled artisan.

Compositions comprising the expression vectors of the present invention and a suitable carrier are also envisioned. Such carriers are well known in the art and refer to a diluent, adjuvant, excipient, or vehicle with which the therapeutic is administered. Such suitable carriers can be sterile liquids, such as water and oils, including those of petroleum, animal, vegetable or synthetic origin, such as peanut oil, soybean oil, mineral oil, sesame oil and the like. Water is a preferred carrier when the composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain a therapeutically effective amount of the retroviral vector of the present invention, together with a suitable amount of carrier so as to provide the form for proper administration to the patient. The formulation should suit the mode of administration.

The U3 Region

As discussed previously, the retroviral genome comprises long terminal repeats (LTRs) at the 5' and 3' ends of the genome containing sequences important for replication during the retroviral life cycle. The promoter and enhancer elements of the U3 region are important for generating full-length transcripts of the retroviral genome during replication. During reverse transcription, a portion of the 3' LTR serves as a template for both the 3' as well as the 5' LTR, so the sequence of the 3' LTR is copied into the 5' LTR. Therefore, a deletion or mutation in the 3' U3 region is copied into the 5' LTR, rendering both U3 regions substantially inactive. This duplication of the 3' LTR allows a vector sequence to contain the unaltered 5' U3 region during packaging so as to allow generation of full length transcripts from the 5' LTR to be generated and packaged. However, during replication, the 5' U3 is lost due to the duplication of the 3' U3 region comprising the enhancer-deleted U3 region into the 5' LTR. In this way, full length transcripts are produced for packaging, but the vector is self-inactivating because both LTRs are rendered transcriptionally silent after one round of replication. Alternatively, the U3 regions of both LTRs may be enhancer-deleted, and full length genomic transcripts may be generated using a heterologous promoter.

"Enhancer-deleted" is used herein to refer to U3 regions in which all or a portion of the enhancer has been altered by deletion, addition and/or substitution within and/or around the enhancer such that the enhancer has been substantially inactivated. An enhancer is considered to be substantially inactivated when the alteration of the enhancer is sufficient to substantially eliminate U3-driven transcripts. In one embodiment, less than 1% of the total retroviral transcripts is driven from the U3 region of the LTR as compared to the internal promoter-driven gene expression. In one embodiment of the invention, less than 0.1% of the total transcripts is driven from the U3 region of the LTR. In another embodiment, no detectable U3-driven transcript is found.

In one embodiment of the invention, the enhancer-deleted U3 region is substantially inactivated by deletion of some or all of the enhancer and promoter elements in that region. In another embodiment, the U3 region is substantially inactivated by substitution or insertion of nucleotides in the U3 region. In a further embodiment, the entire U3 region is deleted. The U3 regions of both the known retroviral vectors as well as wild type retroviruses suitable for use in the invention are well known in the art and readily recognized (Coffin, JM, *Fundamental Virology,* pp. 798-800, Fields et al. eds., 3$^{rd}$ Ed., Lippincott-Raven Publ. (1996)).

Internal Promoters

In the present invention, promoters are provided which can produce high viral titer and high levels of gene expression in the enhancer-deleted U3 retroviral vector environment. In one embodiment, the internal promoter is heterologous to the vector, i.e., is not present in the vector as the vector is found in nature. Various promoters were tested, including HCMV IE promoter (SEQ ID NO:1), MLV U3 region (SEQ ID NO:2), CMV enhancer/ubiquitin promoter (SEQ ID NO:3), cytomegalovirus enhancer/chicken β-actin (CAG) promoter (SEQ ID NO:4), human elongation factor 1 alpha (EF-1α) promoter (SEQ ID NO:5), human β-actin (ACTB) promoter (SEQ ID NO:6), human glyceraldehyde-3-phosphate dehydrogenase (GAPDH) promoter (SEQ ID NO:7), human ribosomal protein L10 (RPL10) promoter (SEQ ID NO:8), human leukocyte receptor cluster member 8 (LENG8) promoter (SEQ ID NO:9), human sorting nexin 3 (SNX3) promoter (SEQ ID NO:10), human CCR4-NOT transcription complex, subunit 3 (CNOT3) promoter (SEQ ID NO:11), human copine 1 (CPNE1) promoter (SEQ ID NO:12), human hypothetical protein (HYPO) promoter (SEQ ID NO:13), human dyskeratosis congenita 1, dyskerin (DKC1) promoter (SEQ ID NO:14), human vacuolar protein sorting 72 (VPS72) promoter (SEQ ID NO:15), integrin beta 4 binding protein (ITGB4BP) promoter (SEQ ID NO:16), and ubiquinol-cytochrome c reductase, complex III subunit VII (UQCRQ) promoter (SEQ ID NO:17). It was found that the UQCRQ, SNX3, ITGB4BP, GAPDH, RPL10 and LENG8 promoters could produce high viral titer and high levels of gene expression. These data show that the cellular promoters of the present invention can drive gene expression in enhancer-deleted U3 retroviral vectors. In one embodiment of the invention, the internal promoter may be a fragment or variant of the above-listed promoters which can produce high viral titer and high levels of gene expression. A fragment of a promoter, as used herein, refers to a polynucleotide comprising a sequence that is identical to but less than the full length of the naturally occurring promoter. In one embodiment, the fragment has at least about 20% (e.g., about 30, 40, 50, 60, 70, 80, 85, 90, or 95%) of the transcriptional activity of the full length promoter. Fragments that may be used include, without limitation, fragments of the RPL10 promoter comprising or consisting of the nucleotide sequences about −50 to about +143 (about nucleotides 951 to 1143 of SEQ ID NO:8), about −100 to about +143 (about nucleotides 901 to 1143 of SEQ ID NO:8), about −200 to about +143 (about nucleotides 801 to 1143 of SEQ ID NO:8), about −350 to about +143 (about nucleotides 651 to 1143 of SEQ ID NO:8), about −500 to about +143 (about nucleotides 501 to 1143 of SEQ ID NO:8), about −1000 to about +143 (about nucleotides 1 to 1143 of SEQ ID NO:8), or about −350 to about +1 (about nucleotides 651 to 1001 of SEQ ID NO:8), and fragments of the LENG8 promoter comprising the nucleotide sequences about −50 to about +305 (about nucleotides 970 to 1325 of SEQ ID NO:9), about −100 to about +305 (about nucleotides 920 to 1325 of SEQ ID NO:9), about −200 to about +305 (about nucleotides 820 to 1325 of SEQ ID NO:9), about −385 to about +305 (about nucleotides 635 to 1325 of SEQ ID NO:9), about −1020 to about +305 (about nucleotides 1 to 1325 of SEQ ID NO:9), or about −385 to about +1 (about nucleotides 635 to 1020 of SEQ ID NO:9) (with the transcription start site considered to be +1 for each promoter). A variant of a promoter, as used herein, refers to a polynucleotide comprising a sequence that is at least about 70% (e.g., at least about 80, 85, 90, 91, 92, 93, 94, 95, 96, 97, 98, or 99%) identical to the sequence of a naturally occurring promoter and which has at least about 20% (e.g., about 30, 40, 50, 60, 70, 80, 85, 90, or 95%) of the transcriptional activity of the naturally occurring promoter. A variant of a promoter may also be a fragment of that promoter.

"High viral titers" is used herein to mean that the enhancer-deleted U3 retroviral vector produces at least 10% of infectious retroviral particles containing the vector as the same vector that has functional, unaltered U3 regions in both LTRs. In other embodiments, the titer of the enhancer-deleted U3 vector is at least 20%, 30%, 40%, 50%, 60%, 70%, 80%, 90%, 100%, 110%, 120%, 130%, 140%, 150%, 160%, 170%, 180%, 190%, 200% or more as compared to the U3-functional vector. Such comparisons of the titers can be made in several ways, such as by the expression of a reporter gene, e.g. GFP or luciferase, in transduced cells, selection of transduced cells using a selectable marker expressed by the vectors, or expression of a therapeutic gene by the vectors. Many such methods for measuring viral titers are well known in the art.

"High levels of heterologous gene transcription" or "high levels of gene expression" encompasses the transcription or expression of the heterologous gene that is at least 70% (e.g., at least 80, 90, 95, 96, 97, 98, or 99%) of the total transcripts produced by the retroviral vector and is at least 10% of the transcription or expression as the same gene in the same vector that has functional, unaltered U3 regions in both LTRs. In other embodiments, the transcription or expression of the heterologous gene in the enhancer-deleted U3 vector is at least 20%, 30%, 40%, 50%, 60%, 70%, 80%, 90%, 100%, 110%, 120%, 130%, 140%, 150%, 160%, 170%, 180%, 190%, 200% or more as compared to same gene in the U3-functional vector. Such comparisons can be made, e.g., by measuring reporter gene expression or by analyzing the amounts of the heterologous transcript or protein that is made using standard molecular biology techniques, e.g. by Northern blot analysis, RT-PCR, Western blot analysis, immunohistochemistry and enzyme-linked immunosorbent assays (ELISA).

A promoter of the present invention may comprise a promoter of eukaryotic, prokaryotic or viral origin, and will be sufficient to direct the transcription of a distally located sequence (a sequence linked to the 3' end of the promoter sequence) in a cell. The internal promoter should drive high levels of transcription of the heterologous gene to which it is operably linked while also allowing high viral titers through generation and packaging of the genomic RNA in the producer cell line. The promoter may also further comprise enhancer elements. Promoters and enhancers consist of short arrays of DNA sequences that interact specifically with cellular proteins involved in transcription (Maniatis et al., *Science* 236:1237 (1987)). Promoter and enhancer elements have been isolated from a variety of eukaryotic sources including genes in yeast, insect and mammalian cells, and viruses (analogous control elements are also found in prokaryotes). The selection of a particular promoter and enhancer depends on what cell type is to be used to express the protein of interest.

Promoters, enhancers and other regulatory elements may be tissue specific or cell specific. The term "tissue specific" as it applies to a regulatory element refers to a regulatory element that is capable of directing selective expression of a heterologous gene to a specific type of tissue (e.g., liver) to a greater extent than the expression of the same nucleotide sequence of interest in a different type of tissue (e.g., lung). The term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues. Likewise, the term "cell type specific" as applied to a regulatory element refers to a regulatory element which is capable of directing selective expression of a nucleotide sequence of interest in a specific type of cell to a greater extent than the expression of the same nucleotide sequence of interest in a different type of cell within the same tissue (e.g., hyperproliferative cells, for example, cancer cells). The term "cell type specific" when applied to a regulatory element also means a regulatory element capable of promoting selective expression of a nucleotide sequence of interest in a region within a single tissue.

While any internal promoter capable of producing high levels of transcription while also allowing high viral titers is contemplated in the present invention, in one embodiment, the internal promoter is a cellular promoter. In a further embodiment, the internal promoter is selected from RPL10 promoter (SEQ ID NO:8), LENG8 promoter (SEQ ID NO:9), SNX3 promoter (SEQ ID NO:10), UQCRQ promoter (SEQ ID NO:17), or ITGB4BP promoter (SEQ ID NO:16). In a further embodiment, the internal promoter is a variant of the full length promoter and is capable of driving high levels of transcription of the heterologous gene while the vector comprising the promoter is capable of producing high viral titers. In a further embodiment, the internal promoter consists essentially of the TATA box. In some embodiments, the internal promoter further comprises one or more splicing sites for high levels of gene expression.

To reduce any possibility of insertional activation from the internal promoter, insulator sequences may be used to block the activation effect of the internal promoter to nearby genes (Ramezani et al., *Mol. Ther.* 14:245 (2006)). Another approach is to modify the vector by inserting additional polyadenylation signals to inhibit the read-through from the internal promoter (Ramezani et al., *Mol. Ther.* 14:245 (2006)).

Heterologous Gene

The term "operably linked" is used to describe a linkage between a gene sequence and a promoter or other regulatory or processing sequence such that the transcription of the gene sequence is directed by an operably linked promoter sequence.

The term "gene" refers to a DNA sequence that comprises control and coding sequences necessary for the production of a polypeptide or transcript. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "polynucleotide" or "nucleic acid molecule", as used interchangeably herein, refers to nucleotide polymers of any length, such as two or more, and includes both DNA and RNA. The nucleotides can be deoxyribonucleotides, ribonucleotides, nucleotide analogs (including modified phosphate moieties, bases, or sugars), or any substrate that can be incorporated into a polymer by a suitable enzyme, such as a DNA polymerase or an RNA polymerase.

As will be appreciated by one skilled in the art, the nucleotide sequence of the inserted polynucleotide of interest may be of any nucleotide sequence. For example, the polynucleotide sequence may be a reporter gene sequence or a selectable marker gene sequence. A reporter gene sequence, as used herein, is any gene sequence which, when expressed, results in the production of a protein whose presence or activity can be monitored. Examples of reporter genes include, but are not limited to, luciferase (See, e.g., deWet et al., *Mol. Cell. Biol.* 7:725 (1987) and U.S. Pat Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif), chloramphenicol acetyltransferase, β-galactosidase, alkaline phosphatase, and horse radish peroxidase. Alternatively, the reporter gene sequence may be any gene sequence whose expression produces a gene product that affects cell physiology. Polynucleotide sequences of the present invention may comprise one or more gene sequences that already possess one or more promoters, initiation sequences, or processing sequences.

A reporter gene sequence may be a selectable marker, which is any gene sequence capable of expressing a protein whose presence permits one to selectively propagate a cell which contains it. Selectable markers may be "dominant"; a dominant selectable marker encodes an enzymatic activity that can be detected in any eukaryotic cell line. Examples of dominant selectable markers include, but are not limited to, the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual*, 2nd ed., Cold Spring Harbor Laboratory Press, New York pp. 16.9-16.15 (1989).

Reporter gene sequences are sufficient to permit the recognition or selection of the vector in normal cells. In one embodiment of the invention, the reporter gene sequence may encode an enzyme or other protein which is normally absent from mammalian cells, and whose presence can, therefore, definitively establish the presence of the vector in such a cell.

The retroviral vectors of the present invention provide for the incorporation of heterologous genes into virus particles, thereby providing a means for amplifying the number of infected host cells containing heterologous nucleic acid therein. The incorporation of the heterologous gene facilitates the replication of the heterologous gene within the viral particle, and the subsequent production of a heterologous transcript or protein therein. A gene is said to be heterologous if it is not naturally present in the wild-type of the vector used to deliver the gene into a cell. The term heterologous gene, as used herein, is intended to refer to a nucleic acid molecule.

The heterologous gene may also comprise the coding sequence of a desired product such as a suitable biologically active protein or polypeptide, immunogenic or antigenic protein or polypeptide, or a therapeutically active protein or polypeptide. The polypeptide may supplement deficient or nonexistent expression of an endogenous protein in a host cell. Such gene sequences may be derived from a variety of sources including DNA, cDNA, synthetic DNA, RNA or combinations thereof. Such gene sequences may comprise genomic DNA which may or may not include naturally occurring introns. Moreover, such genomic DNA may be obtained in association with promoter sequences or polyadenylation sequences. The gene sequences of the present invention are preferably cDNA. Genomic DNA or cDNA may be obtained in any number of ways. Genomic DNA can be extracted and purified from suitable cells by means well-known in the art. Alternatively, mRNA can be isolated from a cell and used to prepare cDNA by reverse transcription, or other means. Alternatively, the polynucleotide sequence may comprise a sequence complementary to an RNA sequence, such as an antisense RNA sequence, which antisense sequence can be administered to an individual to inhibit expression of a complementary polynucleotide in the cells of the individual.

Expression of the heterologous gene may provide an immunogenic or antigenic protein or polypeptide to achieve an antibody response. The antibodies thus raised may be collected from an animal in a body fluid such as blood, serum or ascites.

The heterologous gene can also be any nucleic acid of interest that can be transcribed. Generally the foreign gene encodes a polypeptide. Preferably the polypeptide has some therapeutic benefit. The polypeptide may supplement deficient or nonexistent expression of an endogenous protein in a host cell. The polypeptide can confer new properties on the host cell, such as a chimeric signaling receptor, see U.S. Pat. No. 5,359,046. One of ordinary skill can determine the appropriateness of a heterologous gene practicing techniques taught herein and known in the art. For example, the artisan would know whether a heterologous gene is of a suitable size for encapsidation and whether the heterologous gene product is expressed properly.

The particular heterologous gene that can be employed in the present invention is not critical thereto. However, in one embodiment, the heterologous gene encodes cytokines, chemokines, hormones, antibodies, engineered immunoglobulin-like molecules, a single chain antibody, fusion proteins, enzymes, immune co-stimulatory molecules, immunomodulatory molecules, anti-sense RNA, ribozymes, RNA external guide sequences, a transdominant negative mutant of a target protein, a toxin, a conditional toxin, an antigen, a tumour suppressor protein and growth factors, membrane proteins, vasoactive proteins and peptides, anti-viral proteins or variants thereof.

In a further embodiment, the heterologous gene may encode a polypeptide including, but not limited to, immunoglobulins, erythropoietin, alpha-interferon, alpha-1 proteinase inhibitor, angiogenin, antithrombin III, beta-acid decarboxylase, human growth hormone, bovine growth hormone, porcine growth hormone, human serum albumin, beta-interferon, calf intestine alkaline phosphatase, cystic fibrosis transmembrane regulator, Factor VIII, Factor IX, Factor X, insulin, lactoferrin, tissue plasminogen activator, myelin basic protein, insulin, proinsulin, prolactin, hepatitis B antigen, immunoglobulin fragments (e.g., FABs), monoclonal antibody CTLA4 Ig, Tag 72 monoclonal antibody, Tag 72 single chain antigen binding protein, protein C, cytokines and their receptors, including, for instance tumor necrosis factors alpha and beta, their receptors and their derivatives; renin; growth hormone releasing factor; parathyroid hormone; thyroid stimulating hormone; lipoproteins; alpha-1-antitrypsin; follicle stimulating hormone; calcitonin; luteinizing hormone; glucagon; von Willebrands factor; atrial natriuretic factor; lung surfactant; urokinase; bombesin; thrombin; hemopoietic growth factor; enkephalinase; human macrophage inflammatory protein (MIP-1-alpha); a serum albumin such as mullerian-inhibiting substance; relaxin A-chain; relaxin B-chain; prorelaxin; mouse gonadotropin-associated peptide; beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derived growth factor (PDGF); fibroblast growth factor such as aFGF and bFGF; epidermal growth factor (EGF); transforming growth factor (TGF) such as TGF-α and TGF-β, including TGF-β1, TGF-.β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-12; superoxide dismutase; T-cell receptors; surface membrane proteins; decay accelerating factor; viral antigen such as, for example, a portion of the AIDS envelope; transport proteins; homing receptors; addressins; regulatory proteins; antibodies; chimeric proteins, such as immunoadhesins, and fragments or fusions of any of the above-listed polypeptides. In a further embodiment, the heterologous gene encodes an oxidase, in particular NADPH oxidase, e.g. the gp91 subunit of NADPH oxidase. Nucleic acid and protein sequences for these proteins are available in public databases such as GenBank.

Where a particular protein has more than one subunit (such as an immunoglobulin), the genes encoding the sequences may be arranged in a polycistronic sequence in the vector, separated by one or more IRES elements. Alternatively, genes encoding different subunits of a protein may be introduced into the host cell on separate vectors. In accordance with the present invention, the gene encoding the protein of interest preferably comprises one or more introns. The introns may be introns normally associated with the gene or may be synthetic or exogenous introns. In some embodiments, the gene may comprise less than its normal complement of introns. For example, some of the naturally occurring introns may be removed from the gene while others are retained, or one or more of the naturally occurring introns can be replaced by one or more exogenous introns.

By "wild type" or native, it is intended that the nucleotide or amino acid sequence is identical to the sequence found in nature.

By "variant" it is intended to include substantially similar sequences. Thus, for nucleotide sequences or amino acid sequences, variants include sequences that are functionally equivalent, e.g., retain at least 20% (e.g., 30, 40, 50, 60, 70, 80, or 90%) of one or more of the activities of the wild-type sequence. Variant nucleotide sequences also include synthetically derived nucleotide sequences that have been generated, for example, by site directed mutagenesis, but which still retain the function of the native sequence. Generally, nucleotide sequence variants or amino acid sequence variants of the invention will have at least 70%, generally 80%, 85%, 90%, 91%, 92%, 93%, 94%, 95%, 96%, 97%, 98%, or 99% sequence identity to its respective native nucleotide sequence.

One of skill will appreciate that many conservative variations of the nucleic acid constructs disclosed yield a functionally identical construct. Conservative variations of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For example, due to the degeneracy of the genetic code, "silent substitutions" (e.g., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence of a packaging or packageable construct are substituted with different amino acids with highly similar properties, are also readily identified as being highly similar to a disclosed construct. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in any described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company. Finally, the addition of sequences which do not alter the activity of a nucleic acid molecule, such as a non-functional sequence is a conservative modification of the basic nucleic acid. Such conservatively substituted variations of each disclosed sequence are a feature of the present invention.

With respect to the amino acid sequences for the various full-length or mature polypeptides used in the vector system of the present invention, variants include those polypeptides that are derived from the native polypeptides by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Such variants may result from, for example, genetic polymorphism or from human manipulation. Methods for such manipulations are generally known in the art.

One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques.

A variant of a native nucleotide sequence or native polypeptide has substantial identity to the native sequence or native polypeptide. A variant may differ by as few as 1 to 10 amino acid residues, such as 6-10, as few as 5, as few as 4, 3, 2, or even 1 amino acid residue. A variant of a nucleotide sequence may differ by as few as 1 to 30 nucleotides, such as 6 to 20, as low as 5, as few as 4, 3, 2, or even 1 nucleotide residue.

It is intended by "sequence identity" that the same nucleotides or amino acid residues are found within the variant sequence and a reference sequence when a specified, contiguous segment of the nucleotide sequence or amino acid sequence of the variant is aligned and compared to the nucleotide sequence or amino acid sequence of the reference sequence. Methods for sequence alignment and for determining identity between sequences are well known in the art. With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. The contiguous segment used for comparison to the reference nucleotide sequence or reference amino acid sequence will comprise at least 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties.

Cells

Cells comprising the expression vectors of the present invention are also encompassed. In one embodiment, cells comprising enhancer-deleted U3 retroviral vectors are also encompassed. The target cell, which is transduced by the expression vector of the present invention, can be any eukaryotic cell type capable of being transduced, including mammalian cells, avian cells, amphibian cells, plant cells, fish cells, and insect cells, whether located in vitro or in vivo. In one embodiment, the target cell is a mammalian cell, particularly a human cell. The target cell may be a primary cell or a cell line.

In one embodiment, producer cell lines which further comprise the necessary viral proteins in trans to produce infectious retroviral particles comprising the present vector are encompassed by the present invention. Such producer cell lines produce the retroviral capsids and transcribe the retroviral vector, which is then recruited through the packaging signal to the viral capsid. The packaging cell lines required for the construction of producer cell lines are known in the art and typically comprise the retroviral gag-pol and env genes, which provide the enzymes (e.g., reverse transcriptase) and structural proteins (e.g., Gag and Env) required for the infectious retroviral particles. Many such packaging cells are known, such as PG13, ψCRIP, PA317, GP+envAm12, FLYA13, FLYRD18, Phoenix-Ampho, Phoenix-Eco, Phoenix-GALV, PE501, GP+E86, PT67, BING, BOSC23, ProPak-A, and others, as well as lentiviral packaging cell lines (Logan et al., *J Virol.* 78:8421-8436 (2004)). Further, packaging cell lines can be transiently transfected for short term use or have the viral genes integrated into their genome for long term use.

Many packaging cell lines utilize the native envelope of the retrovirus upon which the retroviral vector is based. It is also possible to alter the host range of cells that the viral vectors of the present invention can infect by utilizing an envelope gene from another closely related virus. In other words, it is possible to expand the host range of the retroviral vectors of the present invention by taking advantage of the capacity of the envelope proteins of certain viruses to participate in the encapsidation of other viruses. Examples of retroviral-derived env genes include, but are not limited to: the G-protein of vesicular-stomatitis virus (VSV-G), gibbon ape leukemia virus (GaLV), cat endogenous virus RD114, Rous sarcoma virus (RSV), amphotropic Moloney murine leukemia virus (MoMuLV), ecotropic Moloney murine leukemia virus (MoMuLV), 10A1 murine leukemia virus, Molony mink cell focus-inducing virus (MCFV), Mus dunni endogenous virus (MDEV), mouse mammary tumor virus (MMTV), and human immunodeficiency virus (HIV). All of these viral envelope proteins efficiently form pseudotyped virions with genome and matrix components of other viruses. As used herein, the term "pseudotype" refers to a viral particle that contains nucleic acid of one virus but the envelope protein of another virus. In general, either VSV-G or GaLV pseudotyped vectors have a very broad host range, and may be pelleted to titers of high concentration by ultracentrifugation while still retaining high levels of infectivity.

Methods of the Invention

The present invention further provides methods of producing infectious retroviral particles comprising the retroviral vector of the present invention by cultivating a producer cell line as described above, collecting the supernatant from the cell culture, and filtering the supernatant to obtain a cell-free viral supernatant. One of skill in the art would readily optimize the conditions for obtaining good viral titers, such as using the appropriate culture medium and determining the optimal collection time periods and cell densities in the culture.

It is further provided herein a method for transducing target cells comprising contacting said cells with the viral supernatant prepared as described above and comprising infectious retroviral particles according to the invention. The target cell, as described above, may be, but is not limited to, mammalian cells, human cells, primate cells, or murine cells. The target cells may be primary cells or cell lines. The method may further comprise the addition of substances to increase transduction to the viral supernatant, such as polybrene, retronectin, and/or protamine sulfate. Additionally, the method may further comprise low-speed centrifugation of the cells once the viral supernatant is applied. These and other transduction optimization techniques are well known and routine in the art.

The present invention further provides a method of treating a subject by administering cells transduced with the retroviral vector of the invention, wherein the heterologous gene encodes a therapeutically useful polypeptide or transcript. In one embodiment, the cells are transduced in vitro or ex vivo.

The present invention further provides a method of treating a subject comprising administering a composition comprising the expression vector of the invention and a suitable carrier, wherein the heterologous gene encodes a therapeutically useful polypeptide or transcript. In one embodiment, the nucleic acid of interest encodes a therapeutic agent. The term "therapeutically useful" is used in a generic sense and includes treating agents, prophylactic agents, and replacement agents. A therapeutic agent may be considered therapeutic if it improves or prevents at least one symptom of a disease or medical condition. Genetic diseases which may be treated with vectors and/or methods of the present invention include those in which long-term expression of the therapeutic nucleic acid is desired. In a further embodiment, the method is for treating a genetic disorder, a proliferation disorder, or an infectious disease. A further embodiment includes a method for treating one or more diseases, disorders, or conditions, including but not limited to: neural disorders, immune system disorders, muscular disorders, reproductive disorders, gastrointestinal disorders, pulmonary disorders, cardiovascular disorders, renal disorders, proliferative disorders, and/or cancerous diseases and conditions. Further embodiments include the treatment of neurodegenerative diseases or disorders, Alzheimer's, schizophrenia, epilepsy, neoplasms, cancer and AIDS or other diseases requiring replacement or the up or down regulation of a gene of interest.

Methods of administering the expression vector of the present invention include, but are not limited to, intradermal, intramuscular, intraperitoneal, intravenous, subcutaneous, intranasal, epidural, and oral routes. The vector or composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or localized. In addition, it may be desirable to introduce the vector or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

Kits

It is a further object of this invention to provide a kit or drug delivery system comprising the vectors for use in the methods described herein. All the essential materials and reagents required for administration of the targeted retroviral particle may be assembled in a kit (e.g., packaging cell construct or cell line). The components of the kit may be provided in a variety of formulations. The one or more retroviral vectors of the present invention may be formulated with one or more agents (e.g., a chemotherapeutic agent) into a single pharmaceutically acceptable composition or separate pharmaceutically acceptable compositions.

The components of these kits or drug delivery systems may also be provided in dried or lyophilized forms. When reagents or components are provided as a dried form, reconstitution generally is by the addition of a suitable solvent, which may also be provided in another container means. The kits of the invention may also comprise instructions regarding the dosage and or administration information. The kits or drug delivery systems of the present invention also will typically include a means for containing the vials in close confinement for commercial sale such as, e.g., injection or blow-molded plastic containers into which the desired vials are retained. Irrespective of the number or type of containers, the kits may also comprise, or be packaged with, an instrument for assisting with the injection/administration or placement of the ultimate complex composition within the body of a subject. Such an instrument may be an applicator, inhalant, syringe, pipette, forceps, measured spoon, eye-dropper or any such medically approved delivery vehicle.

It must be noted that as used in this specification and the appended claims, the singular forms "a," "an," "the," and the like, include plural references unless the context clearly dictates otherwise. Thus, for example, reference to "a polynucleotide" includes polynucleotides and "a cell" includes a plurality of cells.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

The following examples are illustrative, but not limiting, of the methods of the present invention. Other suitable modifications and adaptations of the variety of conditions and parameters normally encountered in medical treatment and pharmaceutical science and which are obvious to those skilled in the art are within the spirit and scope of the invention.

EXAMPLE 1

In the present example, the construction process of various promoters is provided.

1) Human cytomegalovirus (HCMV) immediate early (IE) promoter (SEQ ID NO:1)

The HCMV IE promoter was obtained from a pCN plasmid (Lee et al., *Biochem. Biophys. Res. Commun.* 272: 230 (2000)).

2) U3 of MLV (SEQ ID NO:2)

The U3 region of MLV LTR contains strong enhancer and promoter sequences. The U3 region in the MLV 3' LTR was amplified by PCR using an MLV vector, MT (Hong et al., *J.*

*Gene Med.* 6: 724 (2004); U.S. Pat. No. 6,451,595) as a template. The following primer pairs were used for PCR.

```
                                         (SEQ ID NO:18)
ME5:    ACGCGTGCAAGGCATGGAAAAA
        MluI (SEQ ID NO:19)
MP3:    ACGCGTAGATCTGAATTCTACCCGGGCGACGCAGT
        MluI  BglII  EcoRI
```

One hundred microliters of the PCR reaction solution containing 200 ng of the template plasmid DNA and 1 μl each of the primers (10 pmol/μl) were subjected to 35 cycles of PCR amplification reaction by Expend High Fidelity PCR system (Cat#92351824, Roche). Each cycle was conducted for 30 seconds at 95° C. (denaturation), 30 seconds at 55° C. (annealing) and 30 seconds at 72° C. (polymerization).

The amplified fragment of 455 bps was cloned into the pGEM T easy vector (Cat#A1360, Promega, Wis., USA), resulting in pGEM T-MTU3.

3) CMV/Ubiquitin promoter (SEQ ID NO:3)

A. CMV Enhancer

The CMV enhancer was amplified by PCR using pCK (PCT/KR99/00855) as a template. The following primer pairs were used for PCR.

```
                                         (SEQ ID NO:20)
CMV5:   ACGCGTTGACATTGATTATTG
        MluI (SEQ ID NO:21)
KMD1:   TCTAGAGCCAAAACAAACTCCCAT
        XbaI
```

Fifty microliters of the PCR reaction solution containing 200 ng of the template plasmid DNA and 2 μl each of the primers (5 pmol/μl) were subjected to 30 cycles of PCR amplification reaction by Expend High Fidelity PCR system. Each cycle was conducted for 1 minute at 94° C. (denaturation), 1 minute at 55° C. (annealing) and 1 minute at 72° C. (polymerization).

The amplified fragment was cloned into the pGEM T easy vector, resulting in pGEM T-Enh. The nucleotide sequence was confirmed by sequencing.

B. Human Polyubiquitin C Promoter (Gill et al., *Gene Ther.* 8:1539 (2001))

Human polyubiquitin C promoter (−333~+877) was amplified using genomic DNA isolated from HT1080 cells as a template. The following primer pairs were used for PCR.

```
                                         (SEQ ID NO:22)
KMD4:   GCTAGCGGCCTCCGCGCCGGGTTT
        NheI (SEQ ID NO:23)
KMD5:   ACGCGTAGATCTGAATTCGTCTAACAAAAAGCCAA
        MluI  BglII  EcoRI
```

Fifty microliters of the PCR reaction solution containing 200 ng of the template DNA and 2 μl each of the primers (5 pmol/μl) were subjected to 30 cycles of PCR amplification reaction by Expend High Fidelity PCR system. Each cycle was conducted for 1 minute at 94° C. (denaturation), 1 minute at 55° C. (annealing) and 1 minute 30 seconds at 72° C. (polymerization).

The amplified fragment of 1230 bps was cloned into the pGEM T easy vector, resulting in pGEM T-UbC. The nucleotide sequence was confirmed by sequencing.

C. CMV Enhancer/UbC Promoter

To construct a hybrid promoter consisting of the CMV enhancer and the UbC promoter, the SalI-XbaI fragment from pGEM T Easy-Enh was excised and inserted into the SalI-XbaI site of pGEM T Easy-UbC to generate pGEM T Easy-Enh+UbC.

4) CAG (cytomegalovirus enhancer, chicken β-actin promoter) promoter (SEQ ID NO:4)

To obtain the CAG promoter (cytomegalovirus enhancer, chicken β-actin promoter) (SEQ ID NO:4), the Klenow fragment treated SalI-SwaI fragment from pAxCAwt (Takara Bio, Otsu, Japan) was cloned into pGEM T easy (Promega, Wis., USA) to generate pGEM T easy-CAG. The nucleotide sequence was confirmed by sequencing.

5) Human Elongation Factor 1 alpha (EF1-α) promoter (SEQ ID NO:5) (Kim et al., *Gene* 91:217 (1990))

The human Elongation Factor 1 alpha (EF1-α) promoter (−341~+1007) was amplified using genomic DNA isolated from HT1080 cells (human fibrosarcoma cell line, ATCC CCL-121) as a template. The nucleotide sequences of the primer pairs used for PCR are as follows:

```
                                         (SEQ ID NO:24)
EEF1A1F: ACGCGTGTAAGCCAGCAATGGTAGAGGGAAGATTCTGCACG
         MluI (SEQ ID NO:25)
EEF1A1R: GGATCCTTTTGGCTTTTAGGGGTAGTTTTCACGACACC
         BamHI
```

Fifty microliters of the PCR reaction solution containing 500 ng of template genomic DNA, 1 μl each of the primers (10 pmol/μl) and 5 μl of DMSO (dimethyl sulphoxide) were subjected to 30 cycles of PCR amplification reaction by Expend High Fidelity PCR system (Cat#92351824, Roche). Each cycle was conducted for 1 minute at 95° C. (denaturation), 1 minute at 55° C. (annealing) and 1 minute 30 seconds at 72° C. (polymerization).

The amplified fragment was initially cloned into pGEM T easy to generate pGEM T easy-EF. The nucleotide sequence was confirmed by sequencing.

6) Human β-actin promoter (SEQ ID NO:6) (Nakajima-Iijima et al., *Proc. Natl. Acad. Sci. USA* 82: 6133 (1985); Miyamoto, *Nucleic Acids Res.* 15:9095 (1987))

The human β-actin promoter (−387~+944) was amplified using genomic DNA isolated from K562 cells (human myelogenous cell line, ATCC CCL-243) as a template. The nucleotide sequences of the primer pairs used for PCR are as follows:

```
                                         (SEQ ID NO:26)
BApF:   ACGCGTGAGATGTCCACACCTAGGATGTCC
        MluI (SEQ ID NO:27)
BApR:   GGATCCGGTGAGCTGCGAGAATAGCCG
        BamHI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragments were cloned into pGEM T easy, generating pGEM T easy-BA. The nucleotide sequence was confirmed by sequencing.

7) Human glyceraldehyde-3-phosphate dehydrogenase (GAPDH) promoter (SEQ ID NO:7) (Ercolani et al., *J. Biol. Chem.* 263:15335 (1988))

The human GAPDH (GlycerAldehyde-3-Phosphate DeHydrogenase) promoter (−350~+315) was amplified using genomic DNA isolated from HT1080 cells as a template. The nucleotide sequences of the primer pairs used for PCR are as follows:

```
                                         (SEQ ID NO:28)
    GAPDHF:     ACGCGTTTTCATCCAAGCGTGTAAGGG
                MluI (SEQ ID NO:29)
    GAPDHR:     GTTTAAACGGTGTCTGAGCGATGTGGCT
                PmeI
```

Fifty microliters of the PCR reaction solution containing 500 ng of template genomic DNA, 1 µl each of the primers (10 pmol/µl) and 5 µl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was cloned into pGEM T easy, producing pGEM T easy-GAPDH. The nucleotide sequence was confirmed by sequencing.

8) Human ribosomal protein L10 (RPL10) promoter (SEQ ID NO:8) (NCBI accession No: NM_006013, NT_011726; Bignon et al., *Biochem. Biophys. Res. Commun.* 184:1165 (1992))

The human RPL10 (ribosomal protein L10) promoter (−350~+143) (nucleotides 651 to 1143 of SEQ ID NO:8) was amplified using genomic DNA isolated from HT1080 cells as a template. The nucleotide sequences of the primer pairs used for PCR are as follows:

```
                                         (SEQ ID NO:30)
    RPLF:       ACGCGTAGGCCCACCTAGGGTACTTTCCTTT
                MluI (SEQ ID NO:31)
    RPLR:       GGATCCGGCGACACCAGGATCTTCAGTGGCT
                BamHI
```

Fifty microliters of the PCR reaction solution containing 500 ng of template genomic DNA, 1 µl each of the primers (10 pmol/µl) and 5 µl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was cloned into pGEM T easy to generate pGEM T easy-RPL. The nucleotide sequence was confirmed by sequencing.

9) Human leukocyte receptor cluster member 8 (LENG8) promoter (SEQ ID NO:9) (NCBI accession No: AL834532, NT_011109; Cooper et al., *Genome Res.* 16:1 (2006))

The human LENG8 (leukocyte receptor cluster (LRC) member 8) promoter (−385~+305, +1908~+2121) (nucleotides 635 to 1538 of SEQ ID NO:9) was amplified using genomic DNA isolated from HT1080 cells as a template. The nucleotide sequences of the primer pairs used for PCR are as follows:

```
                                         (SEQ ID NO:32)
    LENG8F1:    ACGCGTAGAATTGTTTGAACCCAGGAGGCGG
                MluI (SEQ ID NO:33)
    LENG8R1:    GTTTAAACAAAGTAGAAGACGACGGCGCACGCG
                PmeI (SEQ ID NO:34)
    LENG8F2:    GTTTAAACCCACACCCAGAACTCTTCAGATCCT
                PmeI (SEQ ID NO:35)
    LENG8R2:    GAATTCCTGGACCTTGGGGTATAAGGGGTGG
                EcoRI
```

Fifty microliters of the PCR reaction solution containing 500 ng of template genomic DNA, 1 µl each of the primers (10 pmol/µl) and 5 µl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragments were initially cloned into pGEM T easy, resulting in pGEM T easy-LENG1 and LENG2, respectively. After the confirmation of their nucleotide sequence, the MluI-PmeI fragment of pGEM T easy-LENG1 was cloned into the MluI-PmeI site of pGEM T easy-LENG2, to make pGEM T easy-LENG8.

10) Human sorting nexin 3 (SNX3) promoter (SEQ ID NO:10) (NCBI accession No: NM_152828, NT_025741; Haft et al., *Mol. Cell. Biol.* 18:7278-87 (1998))

The human SNX3 (sorting nexin 3) promoter (−353~+338) was amplified using genomic DNA isolated from HT1080 cells as a template. The nucleotide sequences of the primer pairs used for PCR are as follows:

```
                                         (SEQ ID NO:36)
    SNX3F:      GAATTCAATCCAGACGCGTGTCTGGTGCAA
                EcoRI (SEQ ID NO:37)
    SNX3R:      GGATCCTTCGCTGTAGCTGCTG
                BamHI
```

Fifty microliters of the PCR reaction solution containing 500 ng of template genomic DNA, 1 µl each of the primers (10 pmol/µl) and 5 µl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was cloned into pGEM T easy to generate pGEM T easy-SNX. The nucleotide sequence was confirmed by sequencing.

11) Human CNOT3 (SEQ ID NO:11) (CCR4-NOT transcription complex, subunit 3) promoter (NCBI accession No: NM_014516; Albert et al., *Nucleic Acids Res.* 28:809 (2000))

The human CNOT3 (CCR4-NOT transcription complex, subunit 3) promoter (−350~+654, +5076~+5266) was amplified using genomic DNA isolated from HT1080 cells as a template. The nucleotide sequences of the primer pairs used for PCR are as follows:

```
                                         (SEQ ID NO:38)
    CNOT3F1:    ACGCGTGTAGCTCCTCCCCCAGACCAATTGTTTTAAG
                MluI
```

```
                           (SEQ ID NO:39)
CNOT3R1:  GGATCCTCCATCCTTCCAGCCAGGAGCCAATACCGAC
          BamHI (SEQ ID NO:40)
CNOTF2:   AGATCTTGGGGCTGGTCTCTTGTCAGATAGC
          BglII (SEQ ID NO:41)
CNOTR2:   GGATCCCTTCCCTGCCCTACAGACGCACTCT
          BamHI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragments were initially cloned into pGEM T easy, resulting in pGEM T easy-CNOT1 and CNOT2, respectively. After the confirmation of their nucleotide sequence, the MluI-BamHI fragment of pGEM T easy-CNOT1 was cloned into the MluI-BglII site of pGEM T easy-CNOT2, to make pGEM T easy-CNOT3.

12) Human CPNE1 (copine I) promoter (SEQ ID NO:12) (NCBI accession No: NM_152926; Creutz et al., *J. Biol. Chem.* 273:1393 (1998))

The human CPNE1 (copine I) promoter (−300~+489, +5612~+5999) was amplified using genomic DNA isolated from HT1080 cells as a template. The nucleotide sequences of the primer pairs used for PCR are as follows:

```
                           (SEQ ID NO:42)
CPNE1F1:  ACGCGTGTCCATTTAATCCTCAAAAAACTTA
          MluI (SEQ ID NO:43)
CPNE1R1:  GGATCCTTTTTACTGCAGTCCCCGTTATTAGCTC
          BamHI (SEQ ID NO:44)
CPNE1F2:  AGATCTAGCTGTGAAGCTGAGCTTTATGACT
          BglII (SEQ ID NO:45)
CPNE1R2:  GGATCCCTGATAAAACAAGAGATGAATTTCC
          BamHI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragments were initially cloned into pGEM T easy, resulting in pGEM T easy-CPNEF and CPNER, respectively. After the confirmation of their nucleotide sequence, the MluI-BamHI fragment of pGEM T easy-CPNEF was cloned into the MluI-BglII site of pGEM T easy-CPNER, to make pGEM T easy-CPNE1.

13) Human HYPO (hypothetical protein) promoter (SEQ ID NO:13) (NCBI accession No: AF351613)

The human HYPO (hypothetical protein) promoter (−350~+66) was amplified using genomic DNA isolated from HT1080 cells as a template. The nucleotide sequences of the primer pairs used for PCR are as follows:

```
                           (SEQ ID NO:46)
HYPOF:    ACGCGTTCTTTTACACGTTTGGTTTTATGGT
          MluI (SEQ ID NO:47)
HYPOR:    GGATCCGGCTGCAACAGGCCAGGAAACCTTC
          BamHI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was initially cloned into pGEM T easy to generate pGEM T easy-HYPO. The nucleotide sequence was confirmed by sequencing.

14) Human DKC1 (dyskeratosis congenita 1, dyskerin) promoter (SEQ ID NO:14) (NCBI accession No: BC 009928; Strausberg et al., *Proc. Natl. Acad. Sci. USA* 99:16899 (2002))

The human DKC1 (dyskeratosis congenita 1, dyskerin) promoter (−473~+91) was amplified using genomic DNA isolated from HT1080 cells as a template. The nucleotide sequences of the primer pairs used for PCR are as follows:

```
                           (SEQ ID NO:48)
DKC1F:    ACGCGTGCACACTACTCCTATTGGC
          MluI (SEQ ID NO:49)
DKC1R:    GAATTCGTTACCCTGCACCGCGTGC
          EcoRI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was initially cloned into pGEM T easy to generate pGEM T easy-DKC1. The nucleotide sequence was confirmed by sequencing.

15) Human VPS72 (vacuolar protein sorting 72) promoter (SEQ ID NO:15) (NCBI accession No: NM_005997; Horikawa et al., *Biochem. Biophys. Res. Commun.* 208:999 (1995))

The human VPS72 (vacuolar protein sorting 72) promoter (−466~+43) was amplified using genomic DNA isolated from HT1080 cells as a template. The nucleotide sequences of the primer pairs used for PCR are as follows:

```
                           (SEQ ID NO:50)
VPS72F:   ACGCGTACAAAAATTAGTTGGGCAT
          MluI (SEQ ID NO:51)
VPS72R:   GAATTCACCGCCTACCGAGACTGCG
          EcoRI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was initially cloned into pGEM T easy to generate pGEM T easy-VPS72. The nucleotide sequence was confirmed by sequencing.

16) Human ITGB4BP (InTeGrin Beta 4 Binding Protein) promoter (SEQ ID NO:16) (NCBI accession No: BC011845, NT_028392; Strausberg et al., *Proc. Natl. Acad. Sci. USA* 99:16899 (2002))

The human ITGB4BP (InTeGrin Beta 4 Binding Protein) promoter (−350~+304) was amplified using genomic DNA isolated from HT1080 cells as a template. The nucleotide sequences of the primer pairs used for PCR are as follows:

```
                                        (SEQ ID NO:52)
ITGB4BPF:  ACGCGTTCTGTCCCTCAAGG CACAGCT
           MluI (SEQ ID NO:53)
ITGB4BPR:  GTTTAAACGAGGCCTAGGGGCGGCGGAGGCGGGAGTTCAA
           PmeI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was initially cloned into pGEM T easy to generate pGEM T easy-ITGB4BP. The nucleotide sequence was confirmed by sequencing.

17) Human UQCRQ (UbiQuinol-Cytochrome c Reductase, complex III subunit VII) promoter (SEQ ID NO:17) (NCBI accession No: BC090048, NT_034772; Strausberg et al., *Proc. Natl. Acad. Sci. USA* 99:16899 (2002))

The human UQCRQ (UbiQuinol-Cytochrome c Reductase, complex III subunit VII) promoter (−350~+217) was amplified using genomic DNA isolated from HT1080 cells as a template. The nucleotide sequences of the primer pairs used for PCR are as follows:

```
                                        (SEQ ID NO:54)
UQCRQF:    ACGCGTGTCACCTTTTTGTTCCCTCCC
           MluI (SEQ ID NO:55)
UQCRQR:    GTTTAAACTGTGGCGGCGGCCCTGCAGG
           PmeI
```

Fifty microliters of the PCR reaction solution containing 500 ng of template genomic DNA, 1 μl each of the primers (10 pmol/μl) and 5 μl of DMSO were subjected to 30 cycles of PCR amplification reaction by Expend High Fidelity PCR system. Each cycle was conducted for 1 minute at 95° C. (denaturation), 1 minute at 55° C. (annealing) and 1 minute 30 seconds at 72° C. (polymerization).

The amplified fragment was initially cloned into pGEM T easy to generate pGEM T easy-UQCRQ. The nucleotide sequence was confirmed by sequencing.

EXAMPLE 2

In the present example, the effects of the promoters prepared in EXAMPLE 1 on enhanced green fluorescence protein (eGFP) gene expression in an expression vector were compared.

1. Construction of eGFP Expression Vectors

First, rabbit beta-globin polyA sequence was obtained from pAxCAwt (Takara Bio, Japan) by PCR. The nucleotide sequences of the primer used for PCR are as follows:

```
                                        (SEQ ID NO:56)
RGpA F:    GGATCCTTTTCCCTCTGCCAAA
           BamHI (SEQ ID NO:57)
RGpA R:    ACTAGTATAAGAGAAGAGGGACAGC
           SpeI
```

Fifty microliters of the PCR reaction solution containing 100 ng of template pAxCAwt DNA (1 μl), 1 μl each of the primers (10 pmol/μl) and 5 μl of dNTPs (10 mM) were subjected to 30 cycles of PCR amplification reaction by Expend High Fidelity PCR system. Each cycle was conducted for 1 minute at 95° C. (denaturation), 1 minute at 50° C. (annealing) and 1 minute 30 seconds at 72° C. (polymerization).

The amplified fragment was initially cloned into pGEM T easy to generate pGEM T easy-RGpA. The nucleotide sequence was confirmed by sequencing.

Then, the MluI-BglII fragments from pC-LND-GFP-n, pG-LND-GFP-n, pR-LND-GFP-n, pL-LND-GFP-n, pIT-LND-GFP-n, and pU-LND-GFP-n (described in EXAMPLE 7) were cloned into the MluI-BamHI site of pGEM T easy-RGpA, resulting in pC-GFP-RGpA, pG-GFP-RGpA, pR-GFP-RGpA, pL-GFP-RGpA, pIT-GFP-RGpA, and pU-GFP-RGpA. To construct pS-GFP-RGpA, the EcoRI-XhoI fragment of pS-LND-GFP-n was made blunt and then cloned into the blunted BamH I site of pGEM T easy-RGpA.

2. Analysis of eGFP Expression

The expression vectors containing the eGFP gene were transfected into 293T cells using FuGene6 according to the manufacturer's instructions. The level of GFP expression was measured by flow cytometry analysis. Flow cytometry was performed as follows: 48 hours after transfection, 293T cells were harvested, and washed once with phosphate-buffered saline (PBS) containing 0.1% sodium azide (FACS buffer). Then the cells were re-suspended in PBS, and analyzed by FACSort (Becton Dickinson, Los Angeles, Calif., USA) with the aid of CellQuest (Becton Dickinson) data acquisition and analysis software. The results are given in Table 1.

TABLE 1

| Comparison of GFP expression | |
|---|---|
| Promoter | Relative mean fluorescence intensity |
| CMV | 100 |
| GAPDH | 102.5 |
| RPL10 | 81.9 |
| LENG8 | 66.6 |
| SNX3 | 36.4 |
| ITGB4BP | 76.4 |
| UQCRQ | 47.1 |

The data show that the HCMV and GAPDH promoters produced comparable levels of GFP expression. Other promoters, such as RPL10, LENG8 and ITGB4BP also induced significant GFP expression, indicating the possibility of their use as a promoter in the eukaryotic gene expression system.

EXAMPLE 3

Among the various promoters prepared in EXAMPLE 1, the RPL10 and LENG8 promoters were selected and further characterized to analyze the promoter sequences required for gene expression.

1. Construction of a Series of RPL10 Promoters
  1) Construction of a Series of RPL10 Promoters Various lengths of RPL10 promoter were produced by PCR. RPL promoters were amplified using genomic DNA of HT1080 as a template. The nucleotide sequences of the primer pairs used for PCR are as follows:

```
                                           (SEQ ID NO:58)
RPL F50:    ACGCGTACGCGCGCAGACAGACCGCCTATATAAGCCAT
            MluI (SEQ ID NO:59)
RPL F100:   ACGCGTTGACGTCTGACAGAGCGTCCACCCGTCTTCG
            MluI (SEQ ID NO:60)
RPL F200:   ACGCGTCTGGCCGCCCGCGGCCCTGGTACCCGGTCACC
            MluI (SEQ ID NO:61)
RPL F500:   ACGCGTGTCTCCCCCTCCGGCCTCCCGGGTTGACAAAGG
            MluI (SEQ ID NO:62)
RPL F1000:  ACGCGTGTGCGCTCGAGCAGGATTTCCTCCCGTCCTTCC
            MluI (SEQ ID NO:31)
RPLR:       GGATCCGGCGACACCAGGATCTTCAGTGGCT
            BamHI (SEQ ID NO:63)
RPL R TSS:  GGATCCGCGCTCCTCCGCCTGCGCATGGCTTATATA
            BamHI
```

Fifty microliters of the PCR reaction solution containing 1 μg of template genomic DNA, 1 μl each of the primers (10 pmol/μl) and 5 μl of dNTPs (10 mM) were subjected to 30 cycles of PCR amplification reaction by Expend High Fidelity PCR system. Each cycle was conducted for 1 minute at 95° C. (denaturation), 1 minute at 60° C. (annealing) and 1 minute 30 seconds at 72° C. (polymerization).

The RPL promoter (−350~+143) (nucleotides 651 to 1143 of SEQ ID NO:8) was described in EXAMPLE 1 (8).

The RPL50 promoter (−50~+143) (nucleotides 951 to 1143 of SEQ ID NO:8) was amplified by using primer pairs RPL F50 and RPLR and cloned into pGEM T easy, resulting in pGem T easy-pRPL50.

The RPL100 promoter (−100~+143) (nucleotides 901 to 1143 of SEQ ID NO:8) was amplified by using primer pairs RPL F100 and RPLR and cloned into pGEM T easy, resulting in pGem T easy-pRPL100.

The RPL200 promoter (−200~+143) (nucleotides 801 to 1143 of SEQ ID NO:8) was amplified by using primer pairs RPL F200 and RPLR and cloned into pGEM T easy, resulting in pGem T easy-pRPL200.

The RPL500 promoter (−500~+143) (nucleotides 501 to 1143 of SEQ ID NO:8) was amplified by using primer pairs RPL F500 and RPLR and cloned into pGEM T easy, resulting in pGem T easy-pRPL500.

The RPL1000 promoter (−1000~+143) (nucleotides 1 to 1143 of SEQ ID NO:8) was amplified by using primer pairs RPL F1000 and RPLR and cloned into pGEM T easy, resulting in pGem T easy-pRPL1000.

The RPL TSS promoter (−350~−1) (nucleotides 651 to 1000 of SEQ ID NO:8) was amplified by using primer pairs RPL F and RPL R TSS and cloned into pGEM T easy, resulting in pGem T easy-pRPL TSS.

The nucleotide sequences were confirmed by sequencing.

2) Construction of a Series of eGFP Expression Vectors Containing the RPL Promoter pGem T easy-GFP-RGpA was constructed by inserting the BamHI fragment from pGem T easy-GFP (described in EXAMPLE 4) into the BamHI site of pGem T easyRGpA (described in EXAMPLE 2). Then, the MluI-BamHI fragments of pGem T easy-pRPL promoters were cloned to the MluI-BamHI site of pGem T easy-GFP-RGpA, resulting in pRPL-, pRPL50-, pRPL100-, pRPL200-, pRPL500-, pRPL1000-, and pRPL TSS-GFP-RGpA.

2. Construction of a Series of LENG8 Promoters

1) Construction of a Series of LENG8 Promoters

As described in EXAMPLE 1 (9), the LENG8 promoter was produced by joining 2 fragments (LENG1 and LENG2). To make various lengths of LENG8 promoter, a series of LENG1 fragments were obtained by PCR. Then, the LENG1 fragments were joined to the LENG2 fragment which was described in EXAMPLE 1 (9) to generate final LENG promoters. The genomic DNA of HT1080 was used as a template. The nucleotide sequences of the primer pairs used for PCR are as follows:

```
                                           (SEQ ID NO:64)
LENG F50:   ACGCGTGTGACGTCAGGACGCCGCGGTCAGG
            Mlu I (SEQ ID NO:65)
LENG F100:  ACGCGTTGGCGTTCATTGGCTGTGCAGGGCC
            Mlu I (SEQ ID NO:66)
LENG F200:  ACGCGTTTGTCCCCTCGGGGCCACCGTCCCC
            Mlu I (SEQ ID NO:67)
LENG F1000: ACGCGTTTGTATCAGAGTCCTGGACGGAAAC
            Mlu I (SEQ ID NO:33)
LENG8R1:    GTTTAAACAAAGTAGAAGACGACGGCGCACGCG
            Pme I (SEQ ID NO:68)
LENG R TSS: GTTTAAACCTCTGGTCTTCTTTGGCTTCGACGT
            Pme I
```

Fifty microliters of the PCR reaction solution containing 1 μg of template genomic DNA, 1 μl each of the primers (10 pmol/μl) and 5 μl of dNTPs (10 mM) were subjected to 30 cycles of PCR amplification reaction by Expend High Fidelity PCR system. Each cycle was conducted for 1 minute at 94° C. (denaturation), 1 minute at 55° C. (annealing) and 2 minutes at 72° C. (polymerization).

The L50 fragment (−50~+305) (nucleotides 970 to 1325 of SEQ ID NO:9) was amplified by using primer pairs LENG F50 and LENG8R1 and cloned into pGEM T easy, resulting in pGem T easy-pL50.

The L100 fragment (−100~+305) (nucleotides 920 to 1325 of SEQ ID NO:9) was amplified by using primer pairs LENG F100 and LENG8R1 and cloned into pGEM T easy, resulting in pGem T easy-pL100.

The L200 fragment (−200~+305) (nucleotides 820 to 1325 of SEQ ID NO:9) was amplified by using primer pairs LENG F200 and LENG8R1 and cloned into pGEM T easy, resulting in pGem T easy-pL200.

The L1000 fragment (−1020~+305) (nucleotides 1 to 1325 of SEQ ID NO:9) was amplified by using primer pairs LENG F1000 and LENG8R1 and cloned into pGEM T easy, resulting in pGEM T easy-pL1000.

Then, the MluI-PmeI fragment of pGEM T easy-pL50, -pL100, -pL200, and -pL1000 was cloned into the MluI-PmeI site of pGEM T easy-LENG2 which was described in EXAMPLE 1 (9), to generate pGEM T easy-pLENG50P, -pLENG 100P, -pLENG200P, and -pLENG1000P.

The LENG TSS promoter (−385~−1) (nucleotides 635 to 1019 of SEQ ID NO:9) was amplified by using primer pairs LENG F and LENG R TSS and cloned into pGEM T easy, resulting in pGem T easy-pLENG TSS.

The LENG8 promoter (−385~+305, +1908~+2121) (nucleotides 635 to 1538 of SEQ ID NO:9) was described in EXAMPLE 1 (9).

2) Construction of a Series of eGFP Expression Vectors Containing the LENG Promoter To construct expression vectors containing the eGFP gene, the MluI-EcoRI fragments (EcoRI site made blunt) of pGEM T easy-pLENG promoters were cloned into the MluI-BamHI site (BamHI site made blunt) of pGem T easy-GFP-RGpA, resulting in pLENG-, pLENG50-, pLENG100-, pLENG200-, and pLENG1000-GFP-RGpA. The MluI-PmeI fragment of pGem T easy-pLENG TSS was cloned into the MluI-BamHI site (BamHI site made blunt) of pGem T easy-GFP-RGpA, resulting in pLENG TSS-GFP-RGpA.

3. Analysis of eGFP Expression 293T cells were transfected with the eGFP expression vectors using FuGene6 (Roche, Germany) according to the manufacturer's instructions, and cultured for 48 hours. The level of GFP expression was measured by flow cytometry analysis. Flow cytometry was performed as follows: 48 hours after transfection, 293T cells were harvested, and washed once with PBS containing 0.1% sodium azide. Then the cells were re-suspended in PBS, and analyzed by FACSort with the aid of CellQuest data acquisition and analysis software. The results are given in Table 2.

TABLE 2

Comparison of eGFP expression

Relative mean fluorescence intensity

A. RPL10 promoters

| | |
|---|---|
| RPL-GFP | 100 |
| RPL50-GFP | 20 |
| RPL100-GFP | 40 |
| RPL200-GFP | 70 |
| RPL500-GFP | 150 |
| RPL1000-GFP | 210 |
| RPL TSS-GFP | 20 |

B. LENG8 promoters

| | |
|---|---|
| LENG-GFP | 100 |
| LENG50-GFP | 14 |
| LENG100-GFP | 42 |
| LENG200-GFP | 87 |
| LENG1000-GFP | 170 |
| LENG TSS-GFP | 39 |

The shortest promoter RPL50 or LENG50 could drive GFP expression that was significantly above background, indicating the presence of 50 bp upstream of the transcription start site was sufficient for basal activity. However, the eGFP expression was higher when the longer promoter was used for gene expression for both the RPL10 and LENG8 promoters. The longest RPL10 promoter, RPL1000, could drive higher level of eGFP expression than RPL500 or the others. The longest LENG8 promoter, LENG1000, also showed the highest promoter activity among various LENG promoters. Furthermore, the promoter activity was better when the element between the transcription start site (TSS) and translation start site was included.

EXAMPLE 4

In the present example, the internal promoters were cloned into retroviral vectors, and their effects on viral titer and level of eGFP gene expression were compared.

1. Construction of eGFP Expressing Retroviral Vectors.

1) Construction of Retroviral Vector 1-1) I-D

A retroviral plasmid with U3 deletion was constructed. First, a normal 3' LTR of MLV was amplified using pMT (Hong et al., *J. Gene Med.* 6:724 (2004); U.S. Pat. No. 6,451, 595) as a template. The nucleotide sequences of the primer pairs used for PCR are as follows:

```
                                            (SEQ ID NO:69)
SCV3LB:  GGATCCCTCGAGCGATAAAATAAAAGATTTTATTTAGTCTCC
         BamHI XhoI
```

```
                                            (SEQ ID NO:70)
SCV3LRI: GAATTCGTCGACTGAAAGACCCCCGCTGACGG
         EcoRI SalI
```

The amplified fragment was initially cloned into pGEM T easy, resulting in pGEM T easy-3'LTR.

A deleted form of 3' LTR was amplified using pMT as a template. The nucleotide sequences of the primer used for PCR are as follows:

```
                                            (SEQ ID NO:71)
3'LTR-1: GCTAGCCCCTGTGCCTTATTTGAA
         NheI
```

```
                                            (SEQ ID NO:70)
SCV3LRI: GAATTCGTCGACTGAAAGACCCCCGCTGACGG
         EcoRI SalI
```

The amplified fragment was initially cloned into pGEM T easy, resulting in pGEM T easy-3'dLTR-1. The NheI-SalI fragment was cloned into the NheI-SalI site of pGEM T easy-3'LTR, resulting in pPreSIN2. The BamHI-SalI fragment from pPreSIN2 was cloned into the BamHI-SalI site of pMT, to make I-D.

1-2) I-ND

To facilitate the cloning, new multiple cloning sites (MCS) were introduced into the retroviral plasmid I-D. A 52 bp-length fragment of new MCS was made by polymerase reaction without template. The following primer pairs are used:

```
                                            (SEQ ID NO:72)
NEWMCSF: ACGCGTTTAAACCGCGGAATTCGGATCCACATCGTG
         MluI      SacII    BamHI
```

```
                                            (SEQ ID NO:73)
NEWMCSR: CTCGAGATCTAGGCCTCACGATGTGGATCCGAATTC
         XhoI    StuI  DraIII     EcoRI
```

The amplified fragment containing restriction sites for MluI, PmeI, SacII, EcoRI, BamHI, DraIII, StuI, BglII, and XhoI was initially cloned into pGEM T easy. After the confirmation of the nucleotide sequence, the MluI-XhoI fragment was cloned into the MluI-XhoI site of I-D, resulting in I-ND.

2) Construction of Retroviral Vectors Containing eGFP Gene 2-1) eGFP Gene

To construct retroviral vectors expressing the eGFP gene, the eGFP gene was amplified from pIRUS2-EGFP (CLON- TECH Laboratory, Palo Alto, Calif., USA, Cat. #6029-1) by using the following primer pairs:

```
                                              (SEQ ID NO:74)
eGFP5:    ACGCGTGGATCCATGGTGAGCAAGGGCGAG 3'
          MluI   BamHI (SEQ ID NO:75)
eGFP3:    CTCGAGAGATCTTTACTTGTACAGCTCGTC 3'
          XhoI  BglII
```

The amplified eGFP sequence was cloned into pGEM T easy to generate pGEM T easy-eGFP. The BamHI-BglII fragment was cloned into the BamHI site of retroviral vector pI-D, resulting in pI-D-GFP, and inserted into the BamHI site of retroviral vectors I-ND, producing I-ND-GFP.

2-2) Construction of Retroviral Vectors Containing eGFP Gene pMT-GFP (Kim et al., *Biochem. Biophys. Res. Commun.* 343:1017 (2006)) was constructed by inserting the BamHI-BglII fragment of pGEM T easy-eGFP into the BamHI site of retroviral vector pMT which contains wild-type LTR.

For the retroviral vectors with defective LTR, various internal promoters of EXAMPLE 1 were cloned into a retroviral vector containing the GFP sequence, respectively.

The MluI-BamHI fragment, HCMV IE promoter, from pCN plasmid was cloned into the MluI-BamHI site of pI-D-GFP, resulting in pC-D-GFP. The MluI fragment from pGEM T Easy-MTU3 was inserted into the MluI site of pI-D-GFP, producing pM-D-GFP. The MluI fragment from pGEM T Easy-Enh+UbC was inserted into the MluI site of pI-D-GFP, generating pCU-D-GFP.

The MluI-BamHI fragment, HCMV IE promoter, from pCN plasmid was cloned into the MluI-BamHI site of pI-ND-GFP, resulting in C-ND-GFP. The Klenow fragment treated SalI-SwaI fragment from pAxCAwt (Takara Bio, Otsu, Japan) was cloned into the PmeI site of pI-ND-GFP, resulting in pCA-ND-GFP. The MluI-BamHI fragment from pGEM T easy-EF was cloned into the MluI-BamHI site of pI-ND-GFP, resulting in pE-ND-GFP. The MluI-BamHI fragment from pGEM T easy-BA was cloned into the MluI-BamHI site of pI-ND-GFP, resulting in pB-ND-GFP. The MluI-PmeI fragment from pGEM T easy-GAPDH was cloned into the MluI-PmeI site of pI-ND-GFP, resulting in pG-ND-GFP. The MluI-BamHI fragment from pGEM T easy-RPL was cloned into the MluI-BamHI site of pI-ND-GFP, resulting in pR-ND-GFP. The MluI-EcoRI fragment from pGEM T easy-LENG8 was cloned into the MluI-EcoRI site of pI-ND-GFP, resulting in pLe-ND-GFP. The EcoRI-BamHI fragment from pGEM T easy-SNX was cloned into the EcoRI-BamHI site of pI-ND-GFP, resulting in pS-ND-GFP. The MluI-BamHI fragment from pGEM T easy-CNOT3 was cloned into the MluI-BamHI site of pI-ND-GFP, resulting in pCo-ND-GFP. The MluI-BamHI fragment from pGEM T easy-CPNE1 was cloned into the MluI-BamHI site of pI-ND-GFP, resulting in pCP-ND-GFP. The MluI-BamHI fragment from pGEM T easy-HYPO was cloned into the MluI-BamHI site of pI-ND-GFP, resulting in pHY-ND-GFP. The MluI-EcoRI fragment from pGEM T easy-DKC1 was cloned into the MluI-EcoRI site of pI-ND-GFP, resulting in pD-ND-GFP. The MluI-EcoRI fragment from pGEM T easy-VPS72 was cloned into the MluI-EcoRI site of pI-ND-GFP, resulting in pV-ND-GFP. The MluI-PmeI fragment from pGEM T easy-ITGB4BP was cloned into the MluI-PmeI site of pI-ND-GFP, resulting in pIT-ND-GFP. The MluI-PmeI fragment from pGEM T easy-UQCRQ was cloned into the MluI-PmeI site of pI-ND-GFP, resulting in pU-ND-GFP.

2. Analysis of eGFP Expression 293T cells were transfected with the respective retroviral vector containing eGFP gene, together with amphotropic packaging constructs, pVM-GP and pVM-AE (Yu et al., *Gene Ther.* 10:706 (2003)), and cultured for 48 hours. Cell-free virus was prepared by filtering the culture supernatant through a 0.45 μm filter paper and used to transduce $2 \times 10^5$ HT1080 and K562 cells, respectively. The cells were incubated for 48 hours and harvested for assays. The percentage of GFP positive cells and level of GFP expression (mean fluorescence intensity) were measured by FACS analysis (see Tables 3 and 4).

The FACS analysis was performed as follows: 48 hours after transduction, HT1080 and K562 cells were harvested, and washed once with phosphate-buffered saline (PBS) containing 0.1% sodium azide (FACS buffer). Then the cells were re-suspended in PBS, and analyzed by FACSort (Becton Dickinson, Los Angeles, Calif., USA) with the aid of CellQuest (Becton Dickinson) data acquisition and analysis software.

First, the GFP expression from the retroviral vectors with defective LTR was compared with that from retroviral vector MT-GFP containing wild-type LTR. As given in Table 3, C-D-GFP vector performed as well as MT-GFP. The percentage of GFP positive cells from C-D-GFP vector were higher in HT1080 cells, and more than 80% in K562 cells compared with that from MT-GFP vector. The level of GFP expression driven from C-D-GFP vector were higher in HT1080 cells, and around 70% in K562 cells compared with that driven from MT-GFP vector. From these experiments, we confirmed that the HCMV promoter works well for GFP expression. However, we could not find other promoters which would work as well as the HCMV promoter. The CMV/Ubiquitin hybrid promoter also produced high viral titer and high level of GFP expression, although less than HCMV promoter.

TABLE 3

Comparison of GFP expression

| | HT1080 | | K562 | |
|---|---|---|---|---|
| | Relative % of GFP+ cells | Relative mean fluorescence intensity | Relative % of GFP+ cells | Relative mean fluorescence intensity |
| MT-GFP | 100 | 100 | 100 | 100 |
| C-D-GFP | 110.2 | 243.3 | 81.4 | 67.2 |
| M-D-GFP | 29.6 | 54.4 | 21.7 | 19.9 |
| CU-D-GFP | 68.2 | 59.4 | 46.6 | 56.1 |

As a next step, we tested more retroviral vectors containing various internal promoters other than HCMV promoter. The results are given in Table 4.

TABLE 4

Comparison of GFP expression

| | HT1080 | | K562 | |
|---|---|---|---|---|
| | Relative % of GFP+ cells | Relative mean fluorescence intensity | Relative % of GFP+ cells | Relative mean fluorescence intensity |
| C-ND-GFP | 100 | 100 | 100 | 100 |
| CA-ND-GFP | 7.9 | 37.1 | 3.9 | 94.5 |
| E-ND-GFP | 28.4 | 21.0 | 19.2 | 157.1 |
| B-ND-GFP | 15.3 | 1.3 | 1.5 | 10.4 |

TABLE 4-continued

Comparison of GFP expression

| | HT1080 | | K562 | |
|---|---|---|---|---|
| | Relative % of GFP+ cells | Relative mean fluorescence intensity | Relative % of GFP+ cells | Relative mean fluorescence intensity |
| G-ND-GFP | 84.1 | 9.8 | 68.9 | 51.6 |
| R-ND-GFP | 109.7 | 9.1 | 107.4 | 42.6 |
| L-ND-GFP | 112.2 | 6.1 | 124.4 | 33.3 |
| S-ND-GFP | 83.8 | 2.1 | 57.1 | 12.5 |
| CN-ND-GFP | 52.5 | 1.9 | 31.4 | 11.7 |
| CP-ND-GFP | 48.2 | 1.4 | 40.1 | 12.2 |
| HY-ND-GFP | 19.7 | 6.5 | 14.9 | 44.3 |
| D-ND-GFP | 42.2 | 1.7 | 44.7 | 17.0 |
| V-ND-GFP | 17.5 | 1.2 | 18.0 | 12.4 |
| IT-ND-GFP | 96.0 | 3.0 | 79.5 | 18.1 |
| U-ND-GFP | 89.7 | 2.6 | 82.9 | 17.7 |

As shown in Table 4, the HCMV promoter produced the highest level of gene expression (see the mean fluorescence intensity) and high number of GFP positive cells both in HT1080 and K562 cells. However, the LENG8 and RPL10 promoter gave the highest viral titer (percentage of transduced cells) both in HT1080 and K562 cells. The level of GFP expression driven from these two promoters was relatively low in HT1080 cells, but more than 30% compared with the HCMV promoter in K562 cells. Therefore, the LENG8 and RPL10 promoter can be used for gene expression in a retroviral vector system in some cell types. In addition, the GAPDH, UQCRQ, ITGB4BP, and SNX3 promoters produced relatively high viral titer (more than 80% of CMV promoter).

The CA-ND-GFP and E-ND-GFP vectors produced the highest level of GFP expression in K562 cells, however, the viral titer from these vectors was very low, making the use of these vectors difficult.

EXAMPLE 5

In the present example, the effects of internal promoters on viral titer and level of gp91 gene expression were compared.

1. Construction of gp91 Expressing Retroviral Vectors 1) gp91-phox Gene (NCBI Accession No: NM_000397)

To construct retroviral vectors expressing human gp91-phox, gp91 cDNA was cloned from the total RNA of human peripheral blood lymphocytes by RT-PCR. The nucleotide sequences of primers used in this step are as follows:

```
                                       (SEQ ID NO: 76)
GP91F:    GGATCCATGGGGAACTGGGCTGTGAAT
          BamHI (SEQ ID NO: 77)
GP91R:    GGATCCCTCGAGTTAGAAGTTTTCCTTGTTGAAAA
          BamHI  XhoI
```

The amplified fragment was initially cloned into pGEM T easy to generate pGEM T easy-gp91 and its nucleotide sequence was confirmed.

2) pPromoter-ND

The MluI-BamHI fragment, HCMV IE promoter, from pCN plasmid was cloned into the MluI-BamHI site of pI-ND, resulting in pC-ND. The MluI-PmeI fragment from pGEM T easy-GAPDH was cloned into the MluI-PmeI site of pI-ND, resulting in pG-ND. The MluI-BamHI fragment from pGEM T easy-RPL was cloned into the MluI-BamHI site of pI-ND, resulting in pR-ND. The MluI-EcoRI fragment from pGEM T easy-LENG8 was cloned into the MluI-EcoRI site of pI-ND, resulting in pL-ND. The EcoRI-BamHI fragment from pGEM T easy-SNX was cloned into the EcoRI-BamHI site of pI-ND, resulting in pS-ND. The MluI-PmeI fragment from pGEM T easy-ITGB4BP was cloned into the MluI-PmeI site of pI-ND, resulting in pIT-ND.

3) Construction of gp91 Expressing Retroviral Vectors

The MT-gp91 vector was constructed by inserting the BamHI fragment of pGEM T easy-gp91 into pMT.

The retroviral vectors where gp91-phox expression is driven by an internal promoter were constructed by inserting the BamHI-XhoI fragment from pGEM T easy-gp91 into the BamHI-XhoI site of pC-ND, pG-ND, pR-ND, pL-ND, pS-ND and pIT-ND, resulting in pC-ND-gp91, pG-ND-gp91, pR-ND-gp91, pL-ND-gp91, pS-ND-gp91 and pIT-ND-gp91, respectively.

The construction process of retroviral vectors pR-LND-gp91-phox-n, pR1000-LND-gp91-n and pR1000-LND-gp91-pA-n-rev was described in EXAMPLE 7 (3).

2. Analysis of gp91 Expression 293T cells were transfected with the respective retroviral vector containing the gp91 gene, together with packaging constructs, pVM-GP and pVM-GeR (Kim et al., *Biochem. Biophys. Res. Commun.* 343:1017 (2006)), by the calcium phosphate precipitation method, and cultured for 48 hours. Cell-free virus was prepared by filtering the culture supernatant through a 0.45 µm filter paper, and used for transduction of K562 cells.

For the transduction of K562 cells, $2.5 \times 10^5$ cells were seeded per well in a 6 well plate the day before the transduction. The same volume of viral supernatants was added per well in the presence of 8 µg/ml polybrene, and the plate was centrifuged (Eppendorf centrifuge 5810R) at 2800 rpm for 90 min at 32° C. After transduction, cells were incubated in a 37° C. $CO_2$ incubator for 2 days.

The gp91 protein expression was analyzed by flow cytometry. K562 or PLB-985/gp91$^{-/-}$ cells were harvested 2 days after transduction, and washed with PBS. Then the cells were re-suspended in 100 µl PBS, and stained with 1 µl anti-gp91 antibody (7D5; MBL, Japan) for 30 minutes at 4° C. Cells were then washed twice with PBS, re-suspended in 100 µl PBS, and stained with 1 µl of FITC-conjugated anti-mouse antibody raised from goat (Southern Biotechnology Associates, Inc, Birmingham, Ala., USA) for 30 min at 4° C. Then cells were washed three times with PBS, and suspended in 500 µl of PBS. Flow cytometry was performed by FACSort (BD, San Jose, Calif.) with the aid of the CellQuest (BD) data acquisition and analysis software.

First, the gp91 expression from the retroviral vectors MT-gp91, C-ND-gp91, G-ND-gp91, R-ND-gp91, L-ND-gp91, S-ND-gp91 and IT-ND-gp91 was compared. The results are given in Table 5. From the various U3-deleted retroviral vectors, R-ND-gp91 and S-ND-gp91 produced higher viral titer (more than 70% of MT-gp91 in K562 cells) than others. The level of gp91 expression driven from R-ND-gp91 vector was higher than that driven from S-ND-gp91 vector in K562 cells. The C-ND-gp91 vector did not produce gp91 positive cells, although C-ND-eGFP could produce a high level of eGFP expression (Table 4).

TABLE 5

Comparison of gp91 expression

| | K562 | |
|---|---|---|
| | Relative % of gp91+ cells | Relative mean fluorescence intensity |
| MT-gp91 | 100 | 100 |
| C-ND-gp91 | 2.4 | 1.9 |
| G-ND-gp91 | 14.0 | 3.3 |
| R-ND-gp91 | 75.5 | 18.9 |
| L-ND-gp91 | 35.4 | 5.8 |
| S-ND-gp91 | 79.4 | 9.9 |
| IT-ND-gp91 | 47.4 | 5.5 |

It was observed in EXAMPLE 3 that the longer form of RPL10 promoter could drive higher level of GFP gene expression than the short one. We tested whether it would apply to gp91 expression. We constructed the gp91 expression retroviral vector containing the longest RPL10 promoter, RPL1000 (pR1000-LND-gp91-n), and confirmed the effect on gp91 gene expression. We also constructed the retroviral vector pR1000-LND-gp91-n-rev where the RPL1000 promoter driven gp91 gene expression cassette is inserted in reverse direction, and compared the gp91 gene expression. The results are given in Table 6.

TABLE 6

Comparison of gp91 expression

| | K562 | |
|---|---|---|
| | Relative % of gp91+ cells | Relative mean fluorescence intensity |
| R-LND-gp91-n | 100 | 100 |
| R1000-LND-gp91-n | 95.5 | 145.6 |
| R1000-LND-gp91-n-rev | 58.6 | 193.9 |

The R1000-LND-gp91-n vector could produce comparable amount of viral titer (% of gp91+ cells), and higher level of gp91 gene expression (relative mean fluorescence intensity) compared with R-LND-gp91-n vector. The R1000-LND-gp91-n-rev vector could drive the highest level of gp91 gene expression although the viral titer produced from it was half of R-LND-gp91-n.

EXAMPLE 6

The retroviral vectors of this invention can be used for ex vivo gene delivery.

The CD34+ hematopoietic stem cells are collected from a subject. The source of CD34+ cells can be bone marrow aspirates or mobilized peripheral blood. Collected CD34+ cells are cultured in a Vuelife culture bag in serum-free SCGM media (Cell Gro, Germany) containing 300 ng/ml of human stem cell factor (SCF), 300 ng/ml of human FLT-3L, 100 ng/ml of human thrombopoietin (TPO), and 20 ng/ml of human IL-3 for 2 days at 37° C. in 5% $CO_2$ (pre-stimulation). The transduction is performed using a Vuelife culture bag precoated with the CH296 fragment of human fibronectin (Retronectin, TaKaRa Bio). Pre-stimulated cells are transferred to the retronectin-coated Vuelife culture bag, and the retroviral supernatant is added on 3 occasions for 2 days. Cells are then harvested, washed 3 times with saline, re-suspended in the infusion solution (saline containing 1% human serum albumin), and infused into the subject.

EXAMPLE 7

In the present example, the effects of internal promoters on the viral titer and level of gene expression in packaging cell line PG13 were examined.
1. Construction of eGFP Expressing Retroviral Vectors
  1) Construction of Retroviral Vector
  1-1) pI-LND U3-deleted retroviral vectors can not be mobilized following the first round of retroviral transduction because both of the 5' and 3' LTRs become defective after transduction. Accordingly, a stable producer cell line was established by transfecting the retroviral packaging cells with plasmid DNA, thus allowing stable integration of the vectors in the genome of the retroviral packaging cells. Linearization of vector DNA is important in having all transfectants contain the proper DNA arrangement in their chromosome.

To construct retroviral vectors convenient for linearization, two restriction enzyme sites for linearization were introduced into the retroviral plasmid pI-ND. One of the restriction enzyme sites was introduced by inserting a fragment, L1, in front of the 5' LTR at a distance of about 200 bp, and the other site, L2, at the back of the 3'LTR. L1 fragment was produced without a template by performing a polymerase reaction. L2 fragment was amplified using pUC18 (Promega, Wis., USA) as a template. The nucleotide sequences of the primer are as follows:

```
                                    (SEQ ID NO:78)
L1F:   5' GCTCTTCCGCTCACGTGTGATCAATTTAAATTTCGAA
          SapI     PmlI     BclI   SwaI   BstBI (SEQ ID NO:79)
L1R:   5' AGCGGAAGAGCTTCGAAATTTAAATTGATCACACGTG
          SapI       BstBI  SwaI    BclI    PmlI (SEQ ID NO:80)
L2F:   5' AGGCCTGGTCACCGGCCATTATGGCCACGTGATCATT
          StuI  BstEII  SfiI                BclI
          TAAATTTGAAGCATTTATCAGGGTTA (SEQ ID NO:81)
L2R:   5'TATTCGCGCGTTTCGGTGATGAATATT
          SspI
```

The amplified L1 fragment containing the restriction sites for SapI, PmlI, BclI, SwaI, BstBI and SapI was initially cloned into pGEM T easy (Promega, Wis., USA), resulting in pGem T easy-L1. After the confirmation of the nucleotide sequence, the SapI fragment released from pGem T easy-L1 was inserted into the SapI site of pI-ND, resulting in pI-L1ND. The amplified L2 fragment containing restriction sites for StuI, BstEII, SfiI, PmlI, BclI, SwaI and SspI was initially cloned into pGEM T easy (Promega, Wis., USA), resulting in pGem T easy-L2. After the confirmation of the nucleotide sequence, the StuI-SspI fragment released from pGem T easy-L2 was cloned into the SspI site of pI-L1ND, resulting in pI-LND.

1-2) pI-LND-n

To construct a producer cell line with high viral titer, it is important to select transfectants containing the retroviral vector DNA. The drug-resistance genes are frequently used for this purpose. However, it is not favorable to have the drug-resistant gene inside the vector genome because, if included, this gene is going to be expressed in vivo. Therefore, we prepared the vector construct harboring the drug-resistant gene cassette outside of the retroviral genome.

First, we used the neomycin-resistance gene for the selection of transfectants. For the expression of the neomycin-resistance gene, the human β-actin promoter and polyadenylation sequence were linked to the bacterial Neo coding sequence.

The human β-actin promoter was amplified using genomic DNA from K562. The nucleotide sequences of the primer used for PCR are as follows:

```
                                           (SEQ ID NO:82)
BApF:   5' GTCGACATTAATGCCGGTGAGTGAGCGGCGCGGGGCCAA
           SalI  PshBI (SEQ ID NO:83)
BApR:   5' GGATCCGGTGGCGCGTCGCGCCGCTGGGTTTT
           BamHI
```

The amplified fragment was cloned into pGEM T easy, resulting in pGEM T easy-pBA.

The bacterial Neo coding gene was amplified using pcDNA 3.1 (Invitrogen, Calif., USA). The nucleotide sequences of the primer used for PCR are as follows:

```
                                           (SEQ ID NO:84)
NeoF:   5' AGATCTATGGGATCGGCCATTGAACAA
           BglII (SEQ ID NO:85)
pAR:    5' CATATGTCATAATCAGCCATACCACATTT
           NdeI
```

The amplified fragment was cloned into pGEM T easy, resulting in pGEM T easy-Neo.

The polyadenylation signal sequence was amplified using pTet-On (Clontech, TAKARA bio, Japan). The nucleotide sequences of the primer used for PCR are as follows:

```
                                           (SEQ ID NO:86)
SVpAF:     CTCGAGATGGGATCGGCCATTGAACAA
           XhoI (SEQ ID NO:87)
SVpAR:     CATATGAGTAATCAGCCATACCACATTT
           NdeI
```

The amplified fragment was cloned into pGEM T easy, resulting in pGEM T easy-pA.

After the confirmation of the nucleotide sequence, the XhoI-NdeI fragment released from pGEM T easy-pA was inserted into the XhoI-NdeI site of pGEM T easy-Neo, to make pGEM T easy-NeopA. The BglII-NdeI fragment was cloned into the BamHI-NdeI site of pGEM T easy-pBA, resulting in pGEM T easy-pBA-Neo-pA. The MluI-EcoRI-Klenow-treated fragment was clone into the SspI site of pI-LND, resulting in pI-LND-n.

2) Construction of Retroviral Vectors Containing eGFP Gene 2-1) pI-LND-GFP-n

The BamHI-BglII fragment released from pGem T easy-eGFP (described in EXAMPLE 2) was cloned into the BamHI site of pI-LND-n, resulting in pI-LND-GFP-n.

2-2) Construction of Retroviral Vectors Containing eGFP Gene

Various internal promoters of EXAMPLE 1 were cloned into the retroviral vectors containing GFP sequence, respectively.

The MluI-BamHI fragment, HCMV IE promoter, from pCN plasmid was cloned into the MluI-BamHI site of pI-LND-GFP-n, resulting in pC-LND-GFP-n. The MluI-PmeI fragment from pGEM T easy-GAPDH was cloned into the MluI-PmeI site of pI-LND-GFP-n, resulting in pG-LND-GFP-n. The MluI-BamHI fragment from pGEM T easy-RPL was cloned into the MluI-BamHI site of pI-LND-GFP-n, resulting in pR-LND-GFP-n. The MluI-EcoRI fragment from pGEM T easy-LENG8 was cloned into the MluI-EcoRI site of pI-LND-GFP-n, resulting in pL-LND-GFP-n. The EcoRI-BamHI fragment from pGEM T easy-SNX was cloned into the EcoRI-BamHI site of pI-LND-GFP-n, resulting in pS-LND-GFP-n. The MluI-PmeI fragment from pGEM T easy-ITGB4BP was cloned into the MluI-PmeI site of pI-LND-GFP-n, resulting in pIT-LND-GFP-n. The MluI-PmeI fragment from pGEM T easy-UQCRQ was cloned into the MluI-PmeI site of pI-LND-GFP-n, resulting in pU-LND-GFP-n.

3) Construction of Retroviral Vectors Containing gp91-phox Gene 3-1) pPromoter-LND Various internal promoters of EXAMPLE 1 were cloned into pI-LND.

The MluI-BamHI fragment, HCMV IE promoter, from pCN plasmid was cloned into the MluI-BamHI site of pI-LND, resulting in pC-LND. The MluI-PmeI fragment from pGEM T easy-GAPDH was cloned into the MluI-PmeI site of pI-LND, resulting in pG-LND. The MluI-BamHI fragment from pGEM T easy-RPL was cloned into the MluI-BamHI site of pI-LND, resulting in pR-LND. The MluI-EcoRI fragment from pGEM T easy-LENG8 was cloned into the MluI-EcoRI site of pI-LND, resulting in pL-LND. The EcoRI-BamHI fragment from pGEM T easy-SNX was cloned into the EcoRI-BamHI site of pI-LND, resulting in pS-LND. The MluI-PmeI fragment from pGEM T easy-ITGB4BP was cloned into the MluI-PmeI site of pI-LND, resulting in pIT-LND. The MluI-PmeI fragment from pGEM T easy-UQCRQ was cloned into the MluI-PmeI site of pI-LND, resulting in pU-LND. The MluI-BamHI fragment from pGEM T easy-pR1000 was cloned into the MluI-BamHI site of pI-LND, resulting in pR1000-LND.

3-2) pPromoter-LND-n

The MluI-EcoRI-Klenow-treated fragment from pGEM T easy-pBA-Neo-pA was cloned into the SspI site of pC-LND, pG-LND, pR-LND, pL-LND, pS-LND, pIT-LND, pU-LND, and pR1000-LND, generating pC-LND-n, pG-LND-n, pR-LND-n, pL-LND-n, pS-LND-n, pIT-LND-n, pU-LND-n, and pR1000-LND-n.

3-3) Construction of Retroviral Vectors Containing gp91-phox Gene

The BamHI fragment from pGEM T easy-gp91 was cloned into the BamHI site of pC-LND-n, pG-LND-n, pR-LND-n, pL-LND-n, pS-LND-n, pIT-LND-n, pU-LND-n, and pR1000-LND-n, generating pC-LND-gp91-phox-n, pG-LND-gp91-phox-n, pR-LND-gp91-phox-n, pL-LND-gp91-phox-n, pS-LND-gp91-phox-n, pIT-LND-gp91-phox-n, pU-LND-gp91-phox-n, and pR1000-LND-gp91-phox-n.

The retroviral vectors where the gp91 gene expression cassette is inserted in reverse direction were also constructed. pC-LND-gp91-pA-n-rev was constructed by i) inserting the MluI-BamHI fragment from pC-LND-gp91-n into the BamHI-StuI site of pI-LND-n, generating pC-LND-n-rev, ii) inserting the BamHI fragment of pGemT easy-gp91 cloned to the BamHI site of pC-LND- n-rev, producing pC-LND-gp91-n-rev, then by iii) inserting the EcoRI fragment of pGEM T easy-RGpA into the Pme I site of pC-LND-gp91-n-rev, resulting in pC-LND-gp91-pA-n-rev. pR1000-LND-gp91- pA-n-rev was constructed by i) inserting the MluI-BamHI fragment from pR1000-LND-gp91-n into the BamHI-StuI site of pI-LND-n, generating p R1000-LND-n-rev, ii) inserting the BamHI fragment of pGemT easy-gp91 cloned to the BamHI site of pR1000-LND-n-rev, producing pR1000-LND-gp91-n-rev, then by iii) inserting the EcoRI fragment of pGEM T easy-RGpA into the Pme I site of pR1000-LND-gp91-n-rev, resulting in pR1000-LND-gp91-pA-n-rev.

As a control, pMT-gp91-n was constructed by inserting the MluI-EcoRI fragment into the SapI site of pMT-gp91.

2. Construction of Producer Cell Lines

1) Linearization of Retroviral Vectors

To linearize retroviral vectors containing eGFP or gp91, 10 µg retroviral plasmid was treated with restriction enzyme (SwaI) for 16 hours. DNA fragment containing retroviral vector was eluted from agarose gel, precipitated and resuspended in 30 µl distilled water. After measuring the DNA concentration, it was used for electroporation.

2) Electroporation

PG13 cell line was used for electroporations. $7.5 \times 10^5$ cells were added in a 0.5 ml volume of serum-free DMEM media to the 0.4-cm cuvette (Bio-Rad Laboratories, Hercules, Calif.) and incubated with linearized retroviral plasmid of 10 µl (1 µg/µl) for 5 min preceding electroporation. Electroporations were conducted using Gene Pulser Xcell™ (Bio-Rad) with voltage of 200 V during 20 msec. Following electroporation, the suspensions were immediately plated in DMEM media with 10% premium FBS.

3) Selection

Cells were selected for neomycin resistance using G-418 (final concentration of 1 µg/ml) following electroporation. After 10 days of selection, cells with integrated plasmids were obtained.

3. Analysis of eGFP Expression $5 \times 10^6$ cells of PG13 producer cell line are plated on a 100 mm dish in DMEM media with 10% premium FBS. After 48 h, the supernatants are harvested and filtered through a 0.45 µm filter. These supernatants are used to measure viral titer using real time PCR and to transduce HT1080 and K562 cells, respectively. The cells are incubated for 48 h, and harvested for assays. The percentage of GFP positive cells and the level of GFP expression (mean fluorescence intensity) are measured by FACS analysis.

4. Analysis of gp91 Expression $5 \times 10^6$ cells of PG13 producer cell line were plated on a 100 mm dish in DMEM media with 10% premium FBS. After 48 h, supernatants containing viruses were harvested and filtered through a 0.45 µm filter. These supernatants were used to transduce K562 cells.

For the transduction of K562 cells, $2.5 \times 10^5$ cells were seeded per well in 6 well plates the day before the transduction. The same amount of viral supernatants was added per well in the presence of 8 µg/ml polybrene, and the plate was centrifuged (Eppendorf centrifuge 5810R) at 2800 rpm for 90 min at 32° C. After transduction, cells were incubated in a 37° C. $CO_2$ incubator for 2 days.

For the quantitative analysis of gp91 protein expression, FACS was performed. K562 cells were harvested, and washed with PBS. Then the cells were re-suspended in 100 µl PBS, and stained with 1 µl anti-gp91 antibody (7D5) for 30 minutes at 4° C. Cells were then washed twice with PBS, re-suspended in 100 µl PBS, and stained with 1 µl of PE-conjugated anti-mouse antibody raised from goat (Southern Biotechnology Associates, Inc, Birmingham, Ala., USA) for 30 min at 4° C. Then cells were washed three times with PBS, and suspended in 500 µl of PBS. Flow cytometry was performed by FACSort with the aid of the CellQuest data acquisition and analysis software. The results are given in FIG. 4. The percentage of gp91 positive cells and the mean fluorescence intensity (the value in parenthesis) are indicated in the figure. As presented in FIG. 4, the R1000 promoter could drive a high level of gp91 gene expression. Furthermore, the R1000 promoter could produce a higher viral titer and a higher level of gene expression when the expression cassette was inserted in the reverse direction. In fact, the viral titer produced from the vector containing the R1000 promoter in reverse direction was higher than that from MT-gp91-n which has wild-type MLV LTR (see the percentage of gp91 positive cells).

The level of NADPH oxidase activity is measured by Dihydrorhodamine-123 (DHR) assay after inducing cell differentiation by treating cells with 0.5% DMF (Dimethylforamide, $C_3H_7NO$). The cells are incubated for 6 days in the presence of DMF, and harvested for assays. The harvested cells are washed 2 times with phosphate-buffered saline (PBS). The cells are suspended with PBS and mixed with 1.8 µl DHR (Molecular Probes, USA, 29 mM). After incubating for 5 minutes at 37° C., the cells are stimulated with 10 µl of phorbol myristate acetate (PMA, 1 µg/ml). Then the percentage of active phagocytic cells and their oxidase activity are measured by FACS analysis.

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A retroviral vector comprising
an RPL10 promoter consisting of the nucleotide sequence of SEQ ID NO: 8 or a fragment thereof as an internal promoter; and
a 5' long terminal repeat (LTR) and a 3' LTR,
wherein the 3' LTR lacks an enhancer element of the U3 region thereof, and
wherein the fragment comprises:
(i) the sequence from about −350 to about −1 relative to the transcription start site of the RPL10 promoter, said sequence from about −350 to about −1 being the nucleotides at positions from about 651 to about 1000 of SEQ ID NO: 8;
(ii) the sequence from about −50 to about +143 relative to the transcription start site of the RPL10 promoter, said sequence from about −50 to about +143 being the nucleotides at positions from about 951 to about 1143 of SEQ ID NO: 8;
(iii) the sequence from about −100 to about +143 relative to the transcription start site of the RPL10 promoter, said sequence from about −100 to about +143 being the nucleotides at positions from about 901 to about 1143 of SEQ ID NO: 8;
(iv) the sequence from about −200 to about +143 relative to the transcription start site of the RPL10 promoter, said sequence from about −200 to about +143 being the nucleotides at positions from about 801 to about 1143 of SEQ ID NO: 8;
(v) the sequence from about −350 to about +143 relative to the transcription start site of the RPL10 promoter, said sequence from about −350 to about +143 being the nucleotides at positions from about 651 to about 1143 of SEQ ID NO: 8; or
(vi) the sequence from about −500 to about +143 relative to the transcription start site of the RPL10 promoter, said sequence from about −500 to about +143 being the nucleotides at positions from about 501 to about 1143 of SEQ ID NO: 8.

2. The vector of claim 1, wherein said fragment comprises the sequence from about −350 to about −1 relative to the transcription start site of the RPL10 promoter, said sequence from about −350 to about −1 being the nucleotides at positions from about 651 to about 1000 of SEQ ID NO: 8.

3. The vector of claim 1, wherein said fragment comprises the sequence from about −50 to about +143 relative to the transcription start site of the RPL10 promoter, said sequence from about −50 to about +143 being the nucleotides at positions from about 951 to about 1143 of SEQ ID NO:8.

4. The vector of claim 3, wherein said fragment comprises the sequence from about −100 to about +143 relative to the transcription start site of the RPL10 promoter, said sequence from about −100 to about +143 being the nucleotides at positions from about 901 to about 1143 of SEQ ID NO:8.

5. The vector of claim 4, wherein said fragment comprises the sequence from about −200 to about +143 relative to the transcription start site of the RPL10 promoter, said sequence from about −200 to about +143 being the nucleotides at positions from about 801 to about 1143 of SEQ ID NO:8.

6. The vector of claim 5, wherein said fragment comprises the sequence from about −350 to about +143 relative to the transcription start site of the RPL10 promoter, said sequence from about −350 to about +143 being the nucleotides at positions from about 651 to about 1143 of SEQ ID NO:8.

7. The vector of claim 6, wherein said fragment comprises the sequence from about −500 to about +143 relative to the transcription start site of the RPL10 promoter, said sequence from about −500 to about +143 being the nucleotides at positions from about 501 to about 1143 of SEQ ID NO:8.

8. The vector of claim 1, wherein said vector is a plasmid vector.

9. The vector of claim 1, wherein the 5' LTR lacks an enhancer element of the U3 region thereof.

10. The vector of claim 1, wherein said promoter further comprises one or more splice sites.

11. The vector of claim 1, wherein said vector is an oncoretroviral vector.

12. The vector of claim 11, wherein said oncoretroviral vector is a murine leukemia viral vector.

13. The vector of claim 1, wherein said vector is a lentiviral vector.

14. The vector of claim 1, wherein the vector comprises a polynucleotide of interest operably linked to the heterologous internal promoter.

15. The vector of claim 14, wherein said polynucleotide of interest is an RNA, an anti-sense RNA, or a small interfering RNA, or encodes a ribozyme.

16. The vector of claim 14, wherein said polynucleotide of interest further comprises a polyadenylation sequence, an IRES, an insulator sequence, splicing sequences or some combination thereof.

17. The vector of claim 14, wherein said polynucleotide of interest encodes a polypeptide.

18. The vector of claim 17, wherein said polypeptide is a therapeutic protein or a reporter protein.

19. The vector of claim 18, wherein said polypeptide is eGFP.

20. The vector of claim 18, wherein said polypeptide is gp91.

21. A composition comprising the vector of claim 1 and a suitable carrier.

22. A cell comprising the vector of claim 1.

23. The cell of claim 22, wherein said cell is a mammalian cell.

24. The cell of claim 23, wherein said cell is a human cell.

25. The cell of claim 23, wherein said cell is a producer cell.

26. A kit comprising the vector of claim 1.

27. A method of producing infectious retroviral particles comprising cultivating the producer cell of claim 25 in a suitable medium, collecting the medium, and filtering the medium to obtain a cell-free viral supernatant comprising the infectious retroviral particles.

* * * * *